US008629257B2

(12) United States Patent
Lacy et al.

(10) Patent No.: US 8,629,257 B2
(45) Date of Patent: Jan. 14, 2014

(54) IL-12/P40 BINDING PROTEINS

(75) Inventors: Susan E. Lacy, Shrewsbury, MA (US);
Emma Fung, Shrewsbury, MA (US);
Jonathan P. Belk, Sterling, MA (US);
Richard W. Dixon, Jefferson, MA (US);
Michael Roguska, Ashland, MA (US);
Paul R. Hinton, Sunnyvale, CA (US);
Shankar Kumar, Pleasanton, CA (US)

(73) Assignee: Abbvie Inc., North Chicago, IL (US)

( * ) Notice: Subject to any disclaimer, the term of this patent is extended or adjusted under 35 U.S.C. 154(b) by 201 days.

(21) Appl. No.: 12/763,048

(22) Filed: Apr. 19, 2010

(65) Prior Publication Data

US 2010/0196315 A1  Aug. 5, 2010

Related U.S. Application Data

(62) Division of application No. 11/478,096, filed on Jun. 29, 2006, now Pat. No. 7,700,739.

(60) Provisional application No. 60/695,679, filed on Jun. 30, 2005.

(51) Int. Cl.
*C07H 21/04* (2006.01)

(52) U.S. Cl.
USPC ................. 536/23.53; 530/387.1; 435/326

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. | |
| 4,816,397 A | 3/1989 | Boss et al. | |
| 4,816,567 A | 3/1989 | Cabilly et al. | |
| 4,880,078 A | 11/1989 | Inoue et al. | |
| 4,946,778 A | 8/1990 | Ladner et al. | |
| 4,980,286 A | 12/1990 | Morgan et al. | |
| 5,128,326 A | 7/1992 | Balazs et al. | |
| 5,223,409 A | 6/1993 | Ladner et al. | |
| 5,225,539 A | 7/1993 | Winter | |
| 5,258,498 A | 11/1993 | Huston et al. | |
| 5,290,540 A | 3/1994 | Prince et al. | |
| 5,403,484 A | 4/1995 | Ladner et al. | |
| 5,427,908 A | 6/1995 | Dower et al. | |
| 5,516,637 A | 5/1996 | Huang et al. | |
| 5,530,101 A | 6/1996 | Queen et al. | |
| 5,565,332 A | 10/1996 | Hoogenboom et al. | |
| 5,565,352 A | 10/1996 | Hochstrasser et al. | |
| 5,571,698 A | 11/1996 | Ladner et al. | |
| 5,580,717 A | 12/1996 | Dower et al. | |
| 5,585,089 A | 12/1996 | Queen et al. | |
| 5,624,821 A | 4/1997 | Winter et al. | |
| 5,627,052 A | 5/1997 | Schrader | |
| 5,648,260 A | 7/1997 | Winter et al. | |
| 5,658,727 A | 8/1997 | Barbas et al. | |
| 5,679,377 A | 10/1997 | Bernstein et al. | |
| 5,693,762 A | 12/1997 | Queen et al. | |
| 5,698,426 A | 12/1997 | Huse | |
| 5,714,350 A | 2/1998 | Co et al. | |
| 5,714,352 A | 2/1998 | Jakobovits | |
| 5,723,323 A | 3/1998 | Kauffman et al. | |
| 5,733,743 A | 3/1998 | Johnson et al. | |
| 5,750,753 A | 5/1998 | Kimae et al. | |
| 5,763,192 A | 6/1998 | Kauffman et al. | |
| 5,766,886 A | 6/1998 | Studnicka et al. | |
| 5,780,225 A | 7/1998 | Wigler et al. | |
| 5,807,715 A | 9/1998 | Morrison et al. | |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,855,913 A | 1/1999 | Hanes et al. | |
| 5,874,064 A | 2/1999 | Edwards et al. | |
| 5,912,015 A | 6/1999 | Bernstein et al. | |
| 5,916,597 A | 6/1999 | Lee et al. | |
| 5,916,771 A | 6/1999 | Hori et al. | |
| 5,934,272 A | 8/1999 | Lloyd et al. | |
| 5,939,598 A | 8/1999 | Kucherlapati et al. | |
| 5,969,108 A | 10/1999 | McCafferty et al. | |

(Continued)

FOREIGN PATENT DOCUMENTS

| | | |
|---|---|---|
| EP | 0 239 400 B1 | 8/1994 |
| EP | 1 176 195 A1 | 1/2002 |

(Continued)

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. (2002) 320, 415-428.*
Holm et al. (2007) 44, 1075-1084.*
Chen et al. J. Mol. Bio. (1999) 293, 865-881.*

(Continued)

*Primary Examiner* — Laura B Goddard
*Assistant Examiner* — Meera Natarajan
(74) *Attorney, Agent, or Firm* — Stephen J. Gaudet, Esq.; Yankwich & Associates, P.C.

(57) ABSTRACT

The present invention encompasses IL-12p40 binding proteins, particularly antibodies that bind human interleukin-12 (hIL-12) and/or human IL-23 (hIL-23). Specifically, the invention relates to antibodies that are chimeric, CDR grafted and humanized antibodies. Preferred antibodies have high affinity for hIL-12 and/or hIL-23 and neutralize h IL-12 and/or hIL-23 activity in vitro and in vivo. An antibody of the invention can be a full-length antibody or an antigen-binding portion thereof. Method of making and method of using the antibodies of the invention are also provided. The antibodies, or antibody portions, of the invention are useful for detecting hIL-12 and/or hIL-23 and for inhibiting hIL-12 and/or hIL-23 activity, e.g., in a human subject suffering from a disorder in which hIL-12 and/or hIL-23 activity is detrimental.

33 Claims, No Drawings

(56) References Cited

U.S. PATENT DOCUMENTS

| | | | |
|---|---|---|---|
| 5,976,862 | A | 11/1999 | Kauffman et al. |
| 5,985,309 | A | 11/1999 | Edwards et al. |
| 5,985,320 | A | 11/1999 | Edwards et al. |
| 5,985,615 | A | 11/1999 | Jakobovits et al. |
| 5,989,463 | A | 11/1999 | Tracy et al. |
| 5,998,209 | A | 12/1999 | Jokobovits et al. |
| 6,019,968 | A | 2/2000 | Platz et al. |
| 6,075,181 | A | 6/2000 | Kucherlapati et al. |
| 6,091,001 | A | 7/2000 | Jakobovits et al. |
| 6,114,598 | A | 9/2000 | Kucherlapati et al. |
| 6,130,364 | A | 10/2000 | Jakobovits et al. |
| 6,180,370 | B1 | 1/2001 | Queen et al. |
| 6,204,023 | B1 | 3/2001 | Robinson et al. |
| 6,350,861 | B1 | 2/2002 | Co et al. |
| 6,660,843 | B1 | 12/2003 | Feige et al. |
| 6,699,658 | B1 | 3/2004 | Wittrup et al. |
| 6,914,128 | B1 | 7/2005 | Salfeld et al. |
| 2002/0137134 | A1 | 9/2002 | Gerngross |
| 2003/0186374 | A1 | 10/2003 | Hufton et al. |
| 2004/0018590 | A1 | 1/2004 | Gerngross |
| 2004/0133357 | A1 | 7/2004 | Zhong et al. |
| 2004/0156849 | A1 | 8/2004 | Gurney |
| 2005/0002937 | A1 | 1/2005 | Giles-Komar et al. |
| 2005/0042664 | A1 | 2/2005 | Wu et al. |
| 2006/0104968 | A1 | 5/2006 | Bookbinder et al. |

FOREIGN PATENT DOCUMENTS

| | | | |
|---|---|---|---|
| EP | 1293514 A1 | | 3/2003 |
| EP | 0 592 106 B1 | | 11/2004 |
| EP | 0 519 596 B1 | | 2/2005 |
| WO | WO 90/02809 | | 3/1990 |
| WO | WO 90/05144 | | 5/1990 |
| WO | WO 90/14424 | | 11/1990 |
| WO | WO 90/14430 | | 11/1990 |
| WO | WO 90/14443 | | 11/1990 |
| WO | WO 91/05548 | | 5/1991 |
| WO | WO 91/09967 | | 7/1991 |
| WO | WO 91/10737 | | 7/1991 |
| WO | WO 91/10741 | | 7/1991 |
| WO | WO 91/17271 | A1 | 11/1991 |
| WO | WO 92/01047 | | 1/1992 |
| WO | WO 92/02551 | | 2/1992 |
| WO | WO 92/03461 | | 3/1992 |
| WO | WO 92/09690 | | 6/1992 |
| WO | WO 92/11272 | | 7/1992 |
| WO | WO 92/15679 | | 9/1992 |
| WO | WO 92/18619 | | 10/1992 |
| WO | WO 92/19244 | | 11/1992 |
| WO | WO 92/20791 | | 11/1992 |
| WO | WO 92/22324 | | 12/1992 |
| WO | WO 93/01288 | | 1/1993 |
| WO | WO 93/06213 | | 4/1993 |
| WO | WO 93/11236 | | 6/1993 |
| WO | WO 94/02602 | | 2/1994 |
| WO | WO 94/18219 | | 8/1994 |
| WO | WO 95/15982 | | 6/1995 |
| WO | WO 95/20401 | | 8/1995 |
| WO | WO 95/24918 | | 9/1995 |
| WO | WO 96/20698 | | 7/1996 |
| WO | WO 96/33735 | | 10/1996 |
| WO | WO 96/34096 | | 10/1996 |
| WO | WO 97/15327 | | 5/1997 |
| WO | WO 97/20032 | | 6/1997 |
| WO | WO 97/29131 | | 8/1997 |
| WO | WO 97/32572 | | 9/1997 |
| WO | WO 97/44013 | | 11/1997 |
| WO | WO 98/16654 | | 4/1998 |
| WO | WO 98/24893 | | 7/1998 |
| WO | WO 98/31346 | | 7/1998 |
| WO | WO 98/31700 | | 7/1998 |
| WO | WO 99/54342 | | 10/1998 |
| WO | WO 98/50433 | | 11/1998 |
| WO | WO 99/06834 | | 2/1999 |
| WO | WO 99/15154 | | 4/1999 |
| WO | WO 99/20253 | | 4/1999 |
| WO | WO 99/25044 | | 5/1999 |
| WO | WO 99/37682 | | 7/1999 |
| WO | WO 99/45031 | | 9/1999 |
| WO | WO 99/53049 | | 10/1999 |
| WO | WO 99/66903 | | 12/1999 |
| WO | WO 00/09560 | | 2/2000 |
| WO | WO 00/37504 | | 6/2000 |
| WO | WO 00/56772 | | 9/2000 |
| WO | WO 01/83525 | | 11/2001 |
| WO | WO 02/12500 | A2 | 2/2002 |
| WO | WO 02/072636 | A2 | 9/2002 |
| WO | WO 2002/088307 | A2 | 11/2002 |
| WO | WO 02/097048 | A2 | 12/2002 |
| WO | WO 03/016466 | A2 | 2/2003 |
| WO | WO 03/035835 | A2 | 5/2003 |
| WO | WO 2004/078140 | A2 | 9/2004 |
| WO | WO 2004/101511 | A2 | 11/2004 |
| WO | WO 2004/101750 | A2 | 11/2004 |
| WO | WO 2004/106381 | A1 | 12/2004 |
| WO | WO 2005/100584 | A2 | 10/2005 |
| WO | WO 2006/069036 | A2 | 6/2006 |

OTHER PUBLICATIONS

Wu et al. J. Mol. Biol. (1999) 294, 151-162.*
Ames et al., *J. Immunol. Methods*, 184: 177-186 (1995).
Azzazy et al., *Clin. Biochem.*, 35: 425-445 (2002).
Babcook et al., *Proc. Natl. Acad. Sci. USA*, 93: 7843-7848 (1996).
Barbas et al., *Proc. Natl. Acad. Sci. USA*, 88: 7978-7982 (1991).
Bentley et al., *Cell*, 32: 181-189 (1983).
Berrebi et al., *Am. J. Path.*, 152: 667-672 (1998).
Better et al., *Science*, 240: 1041-1043 (1988).
Bird et al., *Science*, 242: 423-426 (1988).
Brinkmann et al., *J. Immunol. Methods*, 182: 41-50 (1995).
Broberg et al., *J. Interferon Cytokine Res.*, 22: 641-651 (2002).
Brok et al., *J. Immunol.*, 169: 6554-6563 (2002).
Brown et al., *Proc. Natl. Acad. Sci. USA*, 88: 2663-2667 (1991).
Bucht et al., *Clin. Exp. Immunol.*, 103: 357-367 (1996).
Buchwald et al., *Surgery*, 88: 507-516 (1980).
Burton et al., *Adv. Immunol.*, 57: 191-280 (1994).
Carter et al., *Proc. Natl. Acad. Sci. USA*, 89: 4285-4289 (1992).
Casset et al., *Biochem. Biophys. Res. Comm.*, 307: 198-205 (2003).
Chen et al., *J. Mol. Biol.*, 293: 856-881 (1999).
Chothia et al., *J. Mol. Biol.*, 196: 901-917 (1987).
Chothia et al., *Nature*, 342: 877-883 (1989).
Chothia et al., *J. Mol. Biol.*, 227: 799-817 (1992).
Clackson et al., *Nature*, 352: 624-628 (1991).
Cleek et al., *Proceed. Int'l. Symp. Control. Rel. Bioact. Mater.*, 24: 853-854 (1997).
Co et al., *J. Immunol.*, 148: 1149-1154 (1992).
Co et al., *Mol. Immunol.*, 30: 1361-1367 (1993).
Cole et al., *J. Immunol.*, 159: 3613-3621 (1997).
Cooper et al., *J. Immunol.*, 168: 1322-1327 (2002).
Cua et al., *Nature*, 421: 744-748 (2003).
DeLuca et al., *Rheum. Dis. Clin. North Am.*, 21: 759-777 (1995).
Duchmann et al., *Eur. J. Immunol.*, 26: 934-938 (1996).
During et al., *Ann. Neurol.*, 25: 351-356 (1989).
Durocher et al., *Nucl. Acids Res.*, 30(2e9): 1-9 (2002).
Elkins et al., *Infect. Immun.*, 70: 1936-1948 (2002).
Fais et al., *J. Interferon Res.*, 14: 235-238 (1994).
Foote et al., *J. Mol. Biol.*, 224: 487-499 (1992).
Fuchs et al., *Bio/Technology*, 9: 1369-1372 (1991).
Fuss et al., *J. Immunol.*, 157: 1261-1270 (1996).
Garrard et al., *Bio/Technology*, 9: 1373-1377 (1991).
Gavilondo et al., *BioTechniques*, 29: 128-145 (2000).
Giegé et al., Chapter 1, *In Crystallization of Nucleic Acids and Proteins, a Practical Approach*, 2nd ed., (Ducruix and Giegé, eds.)(Oxford University Press, New York, 1999) pp. 1-16.
Gillies et al., *J. Immunol. Methods*, 125: 191-202 (1989).
Goldspiel et al., *Clin. Pharm.*, 12: 488-505 (1993).
Goodson, J.M., Chapter 6, *In Medical Applications of Controlled Release, vol. II, Applications and Evaluation*, (Langer and Wise, eds.)(CRC Press, Inc., Boca Raton, 1984), pp. 115-138.

(56) References Cited

OTHER PUBLICATIONS

Gram et al., *Proc. Natl. Acad. Sci. USA*, 89: 3576-3580 (1992).
Green et al., *J. Exp. Med.*, 188: 483-495 (1998).
Green et al., *Nature Genet.*, 7: 13-21 (1994).
Griffiths et al., *EMBO J.*, 12: 725-734 (1993).
Hamers-Casterman et al., *Nature*, 363: 446-448 (1993).
Hammerling et al., eds., "Monoclonal Antibodies and T-Cell Hybridomas," In Research Monographs in Immunology, vol. 3 (J.L. Turk, General Editor) (Elsevier, New York, 1981), pp. 563-587.
Hawkins et al., *J. Mol. Biol.*, 226: 889-896 (1992).
Hay et al., *Hum. Antibod. Hybridomas*, 3: 81-85 (1992).
Hieter et al., *J. Biol. Chem.*, 257: 1516-1522 (1982).
Higuchi, R., "Using PCR to Engineer DNA," Chapter 6, *In PCR Technology: Principles and Applications for DNA Amplification*, (Erlich, ed.), (Stockton Press, New York, 1989), pp. 61-70.
Holliger et al., *Proc. Natl. Acad. Sci. USA*, 90: 6444-6448 (1993).
Holm et al., *Mol. Immunol.*, 44: 1075-1084 (2007).
Hoogenboom et al. *Nucl. Acids Res.*, 19: 4133-4137 (1991).
Hoogenboom, *Trends Biotechnol.*, 15: 62-70 (1997).
Hoogenboom et al., *Immunol. Today*, 21: 371-378 (2000).
Howard et al., *J. Neurosurg*, 71: 105-112 (1989).
Huse et al., *Science*, 246: 1275-1281 (1989).
Huston et al., *Proc. Natl. Acad. Sci. USA*, 85: 5879-5883 (1988).
Huston et al., *Methods Enzymol.*, 203: 46-88 (1991).
Jefferis, R., *Biotechnol. Prog.*, 21: 11-16 (2005).
Johnsson et al., *Anal. Biochem.*, 198: 268-277 (1991).
Johnsson et al., *J. Mol. Recognit.*, 8: 125-131 (1995).
Joliot et al., *Proc. Natl. Acad. Sci. USA*, 88: 1864-1868 (1991).
Jones et al., *Nature*, 321: 522-525 (1986).
Jönsson et al., *BioTechniques*, 11: 620-627 (1991).
Jönsson et al., *Ann. Biol. Clin.*, 51: 19-26 (1993).
Junghans et al., *Cancer Res.*, 50: 1495-1502 (1990).
Kabat et al., *Ann. NY Acad. Sci.*, 190: 382-391 (1971).
Kaufman et al., *J. Mol. Biol.*, 159: 601-621 (1982).
Kauffman et al., *J. of Investigative Dermatology*, 123(6): 1037-1044 (2004).
Kellermann et al., *Curr. Opin. Biotechnol.*, 13: 593-597 (2002).
Kettleborough et al., *Eur. J. Immunol.*, 24: 952-958 (1994).
Kipriyanov et al., *Mol. Immunol.*, 31: 1047-1058 (1994).
Kipriyanov et al., *Hum. Antibod. Hybridomas*, 6: 93-101 (1995).
Kobayashi et al., *J. Exp. Med.*, 170: 827-845 (1989).
Köhler et al., *Nature*, 256: 495-497 (1975).
Lam et al., *Proceed. Int'l. Symp. Control. Rel. Bioact. Mater.*, 24: 759-760 (1997).
Langer et al.,*J. Macromol. Sci. Rev. Macromol. Chem. Phys.*, C23(1): 61-126 (1983).
Langer, *Science*, 249: 1527-1533 (1990).
Langrish et al., *Immunological Reviews*, 202: 96-105 (2004).
Levitt, *J. Mol. Biol.*, 168: 595-620 (1983).
Levy et al., *Science*, 228: 190-192 (1985).
Ling et al., *J. Immunol.*, 154: 116-127 (1995).
Little et al., *Immunol. Today*, 21: 364-370 (2000).
Lund et al., *J. Immunol.*, 147: 2657-2662 (1991).
MacCallum et al., *J. Mol. Biol.*, 262: 732-745 (1996).
Manheimer-Lory et al., *J. Exp. Med.*, 174: 1639-1652 (1991).
Marchalonis et al., *Adv. Exp. Med. Biol.*, 484: 13-30 (2001).
McCafferty et al., *Nature*, 348: 552-554 (1990).
Mendez et al., *Nature Genet.*, 15: 146-156 (1997).
Mizushima et al., *Nucl. Acids Res.*, 18: 5322 (1990).
Monteleone et al., *Gastroenterology*, 112: 1169-1178 (1997).
Morgan et al., *Ann. Rev. Biochem.*, 62: 191-217 (1993).
Morita et al., *Arth. Rheum.*, 41: 306-314 (1998).
Morrison et al., *Proc. Natl. Acad. Sci. USA*, 81: 6851-6855 (1984).
Morrison et al., *Science*, 229: 1202-1207 (1985).
Mueller et al., *Proc. Natl. Acad. Sci. USA*, 89: 11832-11836 (1992).
Mulligan, *Science*, 260: 926-932 (1993).
Mullinax et al., *BioTechniques*, 12: 864-869 (1992).
Murphy et al., *J. Exp. Med.*, 198: 1951-1957 (2003).
Muyldermans et al., *Protein Eng.*, 7: 1129-1135 (1994).
Muyldermans et al., *Trends Biochem. Sci.*, 26: 230-235 (2001).
Neuberger et al., *Nature*, 312: 604-608 (1984).
Neurath et al., *J. Exp. Med.*, 182: 1281-1290 (1995).
Nguyen et al., *Immunogenetics*, 54: 39-47 (2002).
Ning et al., *Radiotherapy Oncol.*, 39: 179-189 (1996).
Oi et al., *BioTechniques*, 4: 214-221 (1986).
Olee et al., *J. Exp. Med.*, 175: 831-842 (1992).
Oppmann et al., *Immunity*, 13: 715-725 (2000).
Padlan, *Mol. Immunol.*, 28(4/5): 489-498 (1991).
Padlan et al., *FASEB J.*, 9: 133-139 (1995).
Parham et al., *J. Immunol.*, 168: 5699-5708 (2002).
Parronchi et al., *Am. J. Path.*, 150: 823-832 (1997).
Pascalis et al., *J. Immunol.*, 169: 3076-3084 (2002).
Persic et al., *Gene*, 187: 9-18 (1997).
Petrey et al., *Proteins*, 53: 430-435 (2003).
Pirhonen et al., *J. Immunol.*, 169: 5673-5678 (2002).
Podlaski et al., *Arch. Biochem. Biophys.*, 294: 230-237 (1992).
Poljak, *Structure*, 2: 1121-1123 (1994).
Presta et al., *J. Immunol.*, 151: 2623-2632 (1993).
Queen et al., *Proc. Natl. Acad. Sci. USA*, 86: 10029-10033 (1989).
Ravetch et al., *Cell*, 27: 583-591 (1981).
Riechmann et al., *Nature*, 332: 323-327 (1988).
Roberts et al., *Proc. Natl. Acad. Sci. USA*, 94: 12297-12302 (1997).
Roguska et al., *Proc. Natl. Acad. Sci. USA*, 91: 969-973 (1994).
Rouillard et al., *Nucl. Acids Res.*, 32: W176-W180 (2004).
Rudikoff et al., *Proc. Natl. Acad. Sci. USA*, 79: 1979-1983 (1982).
Saudek et al., *N. Eng. J. Med.*, 321: 574-579 (1989).
Sawai et al., *Am. J. Reprod. Immunol.*, 34: 26-34 (1995).
Schroeder et al., *Proc. Natl. Acad. Sci. USA*, 87: 6146-6150 (1990).
Seder et al., *Proc. Natl. Acad. Sci.*, 90: 10188-10192 (1993).
Sefton, *CRC Crit. Rev. Biomed. Eng.*, 14: 201-240 (1987).
Shapiro et al., *Crit. Rev. Immunol.*, 22: 183-200 (2002).
Shields et al., *J. Biol. Chem.*, 277: 26733-26740 (2002).
Shu et al., *Proc. Natl. Acad. Sci. USA*, 90: 7995-7999 (1993).
Sims et al., *J. Immunol.*, 151: 2296-2308 (1993).
Skerra et al., *Science*, 240: 1038-1041 (1988).
Song et al., *PDA J. Pharm. Sci. Technol.*, 50: 372-377 (1996).
Studnicka et al., *Protein Eng.*, 7: 805-814 (1994).
Takeda et al., *Nature*, 314: 452-454 (1985).
Taylor et al., *Nucl. Acids Res.*, 20: 6287-6295 (1992).
Tolstoshev, *Ann. Rev. Pharmacol. Toxicol.*, 32: 573-596 (1993).
Trinchieri et al., *Immunity*, 19: 641-644 (2003).
Trinchieri, *Nat. Rev. Immunol.*, 3: 133-146 (2003).
Umalia et al., *Nature Biotechnol.*, 17: 176-180 (1999).
Urlaub et al., *Proc. Natl. Acad. Sci. USA*, 77: 4216-4220 (1980).
Vajdos et al., *J. Mol. Biol.*, 320: 415-428 (2002).
Verhoeyen et al., *Science*, 239: 1534-1536 (1988).
Vu et al., *Mol. Immunol.*, 34: 1121-1131 (1997).
Wallick et al., *J. Exp. Med.*, 168: 1099-1109 (1988).
Ward et al., *Nature*, 341: 544-546 (1989).
Windhagen et al., *J. Exp. Med.*, 182: 1985-1996 (1995).
Wright et al., *EMBO J.*, 10: 2717-2723 (1991).
Wu et al., *Biotherapy*, 3: 87-95 (1991).
Wu et al., *J. Biol. Chem.*, 262: 4429-4432 (1987).
Wu et al., *J. Mol. Biol.*, 294: 151-162 (1999).
International Preliminary Report on Patentability ("IPRP"), dated Jan. 22, 2009, issued in PCT/US2006/025584.
International Search Report, dated Aug. 13, 2008, issued in PCT/US2006/025584.
Written Opinion, dated Aug. 13, 2008, issued in PCT/US2006/025584.
Kettleborough et al., "Humanization of a mouse monoclonal antibody by CDR-grafting: the importance of framework residues on loop conformation," Protein Eng., 4(7): 773-783 (1991).
Robinson, C., "Gene therapy—proceeding from laboratory to clinic," Trends Biotechnol., 11(5): 155 (1993).
Carter et al., "Production and Characterization of Monoclonal Antibodies to Human Interleukin-12," Hybridoma, vol. 16, No. 4, pp. 363-369 (Aug. 1, 1997).

(56) References Cited

OTHER PUBLICATIONS

Extended Supplementary Search Report (ESSR), issued Feb. 23, 2012, in counterpart European patent application No. 06 785967.8.
Immunology, Fifth Edition (Roitt et al., eds.) (Mosby International Ltd., London, 1998), pp. 73-77, 80, 96, 97, 104, and 105.
Johnson, G., and Wu, T.T., "The Kabat Database and a Bioinformatics Example," In Methods in Molecular Biology, vol. 248: Antibody Engineering. Methods and Protocols, (Benny K.C. Lo, ed.) (Humana Press Inc., Totowa, NJ, 2004), pp. 11-23.
Tsurushita et al., "Design of humanized antibodies: From anti-Tac to Zenapax," Methods: A Companion to Methods in Enzymology (Academic Press Inc., NY), vol. 36, No. 1, pp. 69-83 (May 1, 2005).
Martin, A.C.R., "Protein Sequence and Structure Analysis of Antibody Variable Domains," In Kontermann and Dübel, eds., Antibody Engineering (Springer-Verlag, Berlin, 2001), chapter 31, pp. 422-439.

\* cited by examiner

SEQUENCE LISTING

```
<160> NUMBER OF SEQ ID NOS: 111

<210> SEQ ID NO 1
<211> LENGTH: 326
<212> TYPE: PRT
<213> ORGANISM: Homo sapiens
<220> FEATURE:
<221> NAME/KEY: PEPTIDE
<222> LOCATION: (1)..(326)
<223> OTHER INFORMATION: Sequence of p40 subunit of IL-12 and IL-23

<400> SEQUENCE: 1

Met Cys His Gln Gln Leu Val Ile Ser Trp Phe Ser Leu Val Phe Leu
1               5                   10                  15

Asp Leu Val Ala Ile Trp Glu Leu Lys Lys Asp Val Tyr Val Val Glu
            20                  25                  30

Leu Asp Trp Tyr Pro Asp Ala Pro Gly Glu Met Val Val Leu Thr Cys
        35                  40                  45

Asp Thr Pro Glu Glu Asp Gly Ile Thr Trp Thr Leu Asp Gln Ser Ser
    50                  55                  60

Glu Val Leu Gly Ser Gly Lys Thr Leu Thr Ile Gln Val Lys Glu Phe
65                  70                  75                  80

Gly Asp Ala Gly Gln Tyr Thr Cys His Lys Gly Gly Glu Val Leu Ser
                85                  90                  95

His Ser Leu Leu Leu Leu His Lys Lys Glu Asp Gly Ile Trp Ser Thr
            100                 105                 110

Asp Ile Leu Lys Asp Gln Lys Glu Pro Lys Asn Lys Thr Phe Leu Arg
        115                 120                 125

Cys Glu Ala Lys Asn Tyr Ser Gly Arg Phe Thr Cys Trp Trp Leu Thr
    130                 135                 140

Thr Ile Ser Thr Asp Leu Thr Phe Ser Val Lys Ser Ser Arg Gly Ser
145                 150                 155                 160

Ser Asp Pro Gln Gly Val Thr Cys Gly Ala Ala Thr Leu Ser Ala Glu
                165                 170                 175

Arg Val Arg Gly Asp Asn Lys Glu Tyr Glu Tyr Ser Val Glu Cys Gln
            180                 185                 190

Glu Asp Ser Ala Cys Pro Ala Ala Glu Glu Ser Leu Pro Ile Glu Val
        195                 200                 205

Met Val Asp Ala Val His Lys Leu Lys Tyr Glu Asn Tyr Thr Ser Ser
    210                 215                 220

Phe Phe Ile Arg Asp Ile Ile Lys Pro Asp Pro Pro Lys Asn Leu Gln
225                 230                 235                 240

Leu Lys Pro Leu Lys Asn Ser Arg Gln Val Glu Val Ser Trp Glu Tyr
                245                 250                 255

Pro Asp Thr Trp Ser Thr Pro His Ser Tyr Phe Ser Leu Thr Phe Cys
            260                 265                 270

Val Gln Val Gln Gly Lys Ser Lys Arg Glu Lys Lys Asp Arg Val Phe
        275                 280                 285

Thr Asp Lys Thr Ser Ala Thr Val Ile Cys Arg Lys Asn Ala Ser Ile
    290                 295                 300
```

```
Ser Val Arg Ala Gln Asp Arg Tyr Tyr Ser Ser Ser Trp Ser Glu Trp
305                 310                 315                 320

Ala Ser Val Pro Cys Ser
                325

<210> SEQ ID NO 2
<211> LENGTH: 330
<212> TYPE: PRT
<213> ORGANISM: Artificial
<220> FEATURE:
<223> OTHER INFORMATION: Sequence of human Ig gamma-1 constant region

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 3
<211> LENGTH: 330
<212> TYPE: PRT
<213> ORGANISM: Artificial
<220> FEATURE:
<223> OTHER INFORMATION: Sequence of human mutant Ig gamma-1 constant region

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 106
<212> TYPE: PRT
<213> ORGANISM: Artificial
<220> FEATURE:
<223> OTHER INFORMATION: Sequence of human Ig Kappa constant region

<400> SEQUENCE: 4

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 5
<211> LENGTH: 105
<212> TYPE: PRT
<213> ORGANISM: Artificial
<220> FEATURE:
<223> OTHER INFORMATION: Sequence of human Ig Lambda constant region

<400> SEQUENCE: 5

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 6
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 6

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 7
<211> LENGTH: 14
<212> TYPE: PRT
<213> ORGANISM: Homo sapiens
<220> FEATURE:
<221> NAME/KEY: PEPTIDE

```
<222> LOCATION: (1)..(14)
<223> OTHER INFORMATION: Heavy Chain Acceptor Sequence (Human)

<400> SEQUENCE: 7

Trp Ile Arg Gln Pro Pro Gly Lys Ala Leu Glu Trp Leu Ala
1               5                   10

<210> SEQ ID NO 8
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Heavy Chain Acceptor Sequence (Human)

<400> SEQUENCE: 8

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 9
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Heavy Chain Acceptor Sequence (Human)

<400> SEQUENCE: 9

Trp Gly Gln Gly Thr Thr Val Thr Val Ser Ser
1               5                   10

<210> SEQ ID NO 10
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 10

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 11
<211> LENGTH: 32
<212> TYPE: PRT
<213> ORGANISM: Homo sapiens
<220> FEATURE:
<221> NAME/KEY: PEPTIDE
<222> LOCATION: (1)..(32)

<400> SEQUENCE: 11

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 12
<211> LENGTH: 30
<212> TYPE: PRT
```

```
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 13
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Heavy Chain Acceptor Sequence (Human)

<400> SEQUENCE: 13

Trp Val Arg Gln Ala Pro Gly Lys Gly Leu Glu Trp Val Gly
1               5                   10

<210> SEQ ID NO 14
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Heavy Chain Acceptor Sequence (Human)

<400> SEQUENCE: 14

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 15
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 16
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Heavy Chain Acceptor Sequence (Human)

<400> SEQUENCE: 16

Trp Val Arg Gln Ala Pro Gly Lys Gly Leu Glu Trp Val Ser
1               5                   10
```

```
<210> SEQ ID NO 17
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Heavy Chain Acceptor Sequence (Human)

<400> SEQUENCE: 17

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 18
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 19
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Heavy Chain Acceptor Sequence (Human)

<400> SEQUENCE: 19

Trp Val Arg Gln Ala Pro Gly Gln Gly Leu Glu Trp Met Gly
1               5                   10

<210> SEQ ID NO 20
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Heavy Chain Acceptor Sequence (Human)

<400> SEQUENCE: 20

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 21
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 21
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 22
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Heavy Chain Acceptor Sequence (Human)

<400> SEQUENCE: 22

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 23
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Light Chain Acceptor Sequence (Human)

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 24
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Light Chain Acceptor Sequence (Human)

<400> SEQUENCE: 24

Trp Tyr Gln Gln Lys Pro Gly Gln Pro Pro Lys Leu Leu Ile Tyr
1               5                   10                  15

<210> SEQ ID NO 25
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Light Chain Acceptor Sequence (Human)

<400> SEQUENCE: 25

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 26
<211> LENGTH: 11
<212> TYPE: PRT
```

```
<213> ORGANISM: Homo sapiens
<220> FEATURE:
<221> NAME/KEY: PEPTIDE
<222> LOCATION: (1)..(11)
<223> OTHER INFORMATION: Light Chain Acceptor Sequence (Human)

<400> SEQUENCE: 26

Phe Gly Gly Gly Thr Lys Val Glu Ile Lys Arg
1               5                   10

<210> SEQ ID NO 27
<211> LENGTH: 23
<212> TYPE: PRT
<213> ORGANISM: Homo sapiens
<220> FEATURE:
<221> NAME/KEY: PEPTIDE
<222> LOCATION: (12)..(23)
<223> OTHER INFORMATION: Light Chain Acceptor Sequence (Human)

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 28
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Light Chain Acceptor Sequence (Human)

<400> SEQUENCE: 28

Trp Tyr Gln Gln Lys Pro Gly Gln Ala Pro Arg Leu Leu Ile Tyr
1               5                   10                  15

<210> SEQ ID NO 29
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Light Chain Acceptor Sequence (Human)

<400> SEQUENCE: 29

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 30
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Light Chain Acceptor Sequence (Human)

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys
            20
```

```
<210> SEQ ID NO 31
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Light Chain Acceptor Sequence (Human)

<400> SEQUENCE: 31

Trp Tyr Gln Gln Lys Pro Glu Lys Ala Pro Lys Ser Leu Ile Tyr
1               5                   10                  15

<210> SEQ ID NO 32
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Light Chain Acceptor Sequence (Human)

<400> SEQUENCE: 32

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 33
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Light Chain Acceptor Sequence (Human)

<400> SEQUENCE: 33

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 34
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Light Chain Acceptor Sequence (Human)

<400> SEQUENCE: 34

Trp Tyr Gln Gln Lys Pro Gly Lys Ala Pro Lys Leu Leu Ile Tyr
1               5                   10                  15

<210> SEQ ID NO 35
<211> LENGTH: 119
<212> TYPE: PRT
<213> ORGANISM: Mouse
<220> FEATURE:
<221> NAME/KEY: PEPTIDE
<222> LOCATION: (1)..(119)
<223> OTHER INFORMATION: Amino Acid Sequence of VH 1D4 region

<400> SEQUENCE: 35

Gln Val Thr Leu Lys Glu Ser Gly Pro Gly Ile Leu Gln Pro Ser Gln
1               5                   10                  15
```

Thr Leu Ser Leu Thr Cys Ser Phe Ser Gly Phe Ser Leu Arg Lys Ser
            20                  25                  30

Val Met Gly Val Ser Trp Ile Arg Gln Pro Ser Gly Lys Gly Leu Glu
        35                  40                  45

Trp Leu Ala His Ile Tyr Trp Asp Asp Lys Tyr Tyr Asn Pro Ser
50                  55                  60

Leu Lys Ser Arg Leu Thr Ile Ser Lys Asp Pro Ser Arg Asn Gln Val
65                  70                  75                  80

Phe Leu Lys Ile Thr Ser Val Asp Thr Ala Asp Ala Ala Thr Tyr Tyr
                    85                  90                  95

Cys Thr Arg Arg Gly Ile Arg Ser Ala Met Asp Tyr Trp Gly Gln Gly
                100                 105                 110

Thr Ser Val Thr Val Ser Ser
        115

<210> SEQ ID NO 36
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 1D4 region

<400> SEQUENCE: 36

Ser Val Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Ile Ile Ser Thr Val Arg Ala
65                  70                  75                  80

Glu Asp Leu Ala Val Tyr Phe Cys Gln Gln Asp Tyr Asn Ser Pro Trp
                85                  90                  95

Thr Phe Gly Gly Gly Thr Lys Leu Glu Ile Lys Arg
            100                 105

<210> SEQ ID NO 37
<211> LENGTH: 120
<212> TYPE: PRT
<213> ORGANISM: Mouse
<220> FEATURE:
<221> NAME/KEY: PEPTIDE
<222> LOCATION: (1)..(120)
<223> OTHER INFORMATION: Amino Acid Sequence of VH 1A6 region

<400> SEQUENCE: 37

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Trp Trp Asp Gly Asp Asn Tyr Tyr Asn Pro Ser
50                  55                  60

Leu Lys Ser Gln Leu Thr Ile Ser Lys Asp Thr Ser Arg Asn Gln Val

```
                65                  70                  75                  80
Phe Leu Arg Ile Ala Thr Val Asp Thr Ala Asp Thr Ala Thr Tyr Tyr
                    85                  90                  95

Cys Ala Arg Arg Thr Arg Val Asn Tyr Ala Met Asp Tyr Trp Gly Gln
                100                 105                 110

Gly Thr Ser Val Thr Val Ser Ser
                115                 120

<210> SEQ ID NO 38
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 1A6 region

<400> SEQUENCE: 38

Ser Val Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Phe Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Trp
                85                  90                  95

Thr Phe Gly Gly Gly Thr Lys Leu Glu Ile Lys Arg
                100                 105

<210> SEQ ID NO 39
<211> LENGTH: 117
<212> TYPE: PRT
<213> ORGANISM: Mouse
<220> FEATURE:
<221> NAME/KEY: PEPTIDE
<222> LOCATION: (11)..(117)
<223> OTHER INFORMATION: Amino Acid Sequence of VH 1D8 region

<400> SEQUENCE: 39

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Asp Ile Leu Pro Gly Ser Gly Ser Thr Asn Tyr Asn Glu Lys Phe
    50                  55                  60

Lys Asp Lys Ala Thr Phe Thr Ala Asp Thr Ser Phe Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Arg Arg Phe Arg Gly Leu Asp Tyr Trp Gly Gln Gly Thr Thr
                100                 105                 110

Leu Thr Val Ser Ser
            115
```

<210> SEQ ID NO 40
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 1D8 region

<400> SEQUENCE: 40

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Ala Trp Tyr Gln Gln Lys Ser Gly Gln Ser Pro Lys Leu Leu Ile
            35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Thr Val Gln Pro
65                  70                  75                  80

Glu Asp Leu Ala Val Tyr Phe Cys Gln Gln Asp Tyr Thr Ser Pro Phe
                85                  90                  95

Thr Phe Gly Ser Gly Thr Lys Leu Glu Ile Lys Arg
            100                 105

<210> SEQ ID NO 41
<211> LENGTH: 117
<212> TYPE: PRT
<213> ORGANISM: Mouse
<220> FEATURE:
<221> NAME/KEY: PEPTIDE
<222> LOCATION: (1)..(117)
<223> OTHER INFORMATION: Amino Acid Sequence of VH 3G7 region

<400> SEQUENCE: 41

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Asn Asp Tyr
                20                  25                  30

Trp Ile Glu Trp Val Lys Gln Arg Pro Gly His Gly Leu Glu Trp Ile
            35                  40                  45

Gly Gly Phe Ser His Gly Ser Gly Ser Thr Asn Tyr Asn Glu Lys Phe
50                  55                  60

Lys Gly Lys Ala Thr Phe Thr Ala Asp Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Arg Phe Arg Gly Met Asp Tyr Trp Gly Gln Gly Thr Ser
            100                 105                 110

Val Thr Val Ser Ser
            115

<210> SEQ ID NO 42
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 3G7 region

<400> SEQUENCE: 42

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Thr Thr Val Gln Ala
65              70                  75                  80

Glu Asp Leu Ala Val Tyr Phe Cys Gln Gln Asp Tyr Ser Ser Pro Trp
                85                  90                  95

Ser Phe Gly Gly Gly Thr Lys Leu Glu Ile Lys Arg
            100                 105
```

<210> SEQ ID NO 43
<211> LENGTH: 117
<212> TYPE: PRT
<213> ORGANISM: Mouse
<220> FEATURE:
<221> NAME/KEY: PEPTIDE
<222> LOCATION: (1)..(117)
<223> OTHER INFORMATION: Amino Acid Sequence of VH 5E8 region

<400> SEQUENCE: 43

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asp Tyr
            20                  25                  30

Ser Met His Trp Val Lys Gln Ala Pro Gly Lys Gly Leu Lys Trp Met
        35                  40                  45

Asp Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65              70                  75                  80

Leu Gln Ile Asn Asn Leu Lys Asn Glu Asp Thr Ala Thr Tyr Phe Cys
                85                  90                  95

Ser Arg Arg Arg Tyr Arg Ala Phe Asp Tyr Trp Gly Gln Gly Thr Thr
            100                 105                 110

Leu Thr Val Ser Ser
        115
```

<210> SEQ ID NO 44
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 5E8 region

<400> SEQUENCE: 44

```
Ser Ile Val Met Thr Gln Ser Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Leu Gly Gln Ser Pro Lys Leu Leu Ile
        35                  40                  45

Tyr Tyr Ala Ser Asn Arg Tyr Thr Gly Val Pro Asp Arg Phe Thr Gly
```

```
                50                  55                   60
Ser Gly Tyr Gly Thr Asp Phe Thr Phe Thr Ile Asn Thr Val Gln Ala
 65                  70                   75                  80

Glu Asp Leu Ala Val Tyr Phe Cys Gln Gln Asp Tyr Thr Ser Pro Tyr
                     85                   90                  95

Thr Phe Gly Gly Gly Thr Lys Leu Glu Ile Gln Arg
                100                  105
```

<210> SEQ ID NO 45
<211> LENGTH: 112
<212> TYPE: PRT
<213> ORGANISM: Mouse
<220> FEATURE:
<221> NAME/KEY: PEPTIDE
<222> LOCATION: (1)..(112)
<223> OTHER INFORMATION: Amino Acid Sequence of VH 8E1 region

<400> SEQUENCE: 45

```
Glu Val Lys Leu Val Glu Ser Gly Gly Gly Leu Val Gln Pro Gly Gly
 1               5                   10                  15

Ser Arg Lys Leu Ser Cys Ala Ala Ser Gly Phe Thr Phe Ser Asp Tyr
                20                  25                  30

Gly Met Val Trp Val Arg Gln Ala Pro Gly Lys Gly Leu Glu Trp Val
            35                  40                  45

Ala Ser Ile Ser Ser Gly Ser Ser Asn Ile Tyr Tyr Ala Asp Thr Val
 50                  55                  60

Lys Gly Arg Phe Thr Ile Ser Arg Asp Asp Pro Asn Asn Thr Leu Phe
 65                  70                  75                  80

Leu Gln Met Arg Ser Leu Arg Ser Glu Asp Thr Ala Met Tyr Tyr Cys
                85                  90                  95

Ala Arg Asn Pro Tyr Trp Gly Gln Gly Thr Thr Leu Thr Val Ser Ser
                100                 105                 110
```

<210> SEQ ID NO 46
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 8E1 region

<400> SEQUENCE: 46

```
Asp Ile Val Met Thr Gln Ser Gln Lys Phe Met Ser Thr Ser Val Gly
 1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Gly Leu Ile
            35                  40                  45

Tyr Ser Ala Ser His Arg Tyr Ser Gly Val Pro Asp Arg Phe Ala Gly
                50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Leu Lys Arg
                100                 105
```

<210> SEQ ID NO 47
<211> LENGTH: 117

```
<212> TYPE: PRT
<213> ORGANISM: Mouse
<220> FEATURE:
<221> NAME/KEY: PEPTIDE
<222> LOCATION: (1)..(117)
<223> OTHER INFORMATION: Amino Acid Sequence of VH 1H6 region

<400> SEQUENCE: 47
```

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Tyr Ile Ser Ser Gly Ser Ser Thr Ile His Tyr Ala Asp Thr Met
    50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
                85                  90                  95

Ala Arg Arg His Tyr Tyr Ala Met Asp Tyr Trp Gly Gln Gly Thr Ser
            100                 105                 110

Val Thr Val Ser Ser
        115

```
<210> SEQ ID NO 48
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 1H6 region

<400> SEQUENCE: 48
```

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Thr Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Phe
                85                  90                  95

Thr Phe Gly Ser Gly Thr Lys Leu Glu Ile Lys Arg
            100                 105

```
<210> SEQ ID NO 49
<211> LENGTH: 122
<212> TYPE: PRT
<213> ORGANISM: Mouse
<220> FEATURE:
<221> NAME/KEY: PEPTIDE
<222> LOCATION: (1)..(122)
<223> OTHER INFORMATION: Amino Acid Sequence of VH 3A11 region

<400> SEQUENCE: 49
```

Glu Val Gln Leu Gln Gln Ser Gly Ala Asp Leu Glu Lys Pro Gly Ala
1               5                   10                  15

```
Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly His Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Trp Gly Gln Phe Gly Leu Leu Trp Asn Ala Met Asp Tyr Trp
            100                 105                 110

Gly Gln Gly Thr Ser Val Thr Val Ser Ser
            115                 120

<210> SEQ ID NO 50
<211> LENGTH: 112
<212> TYPE: PRT
<213> ORGANISM: Mouse
<220> FEATURE:
<221> NAME/KEY: PEPTIDE
<222> LOCATION: (1)..(112)
<223> OTHER INFORMATION: Amino Acid Sequence of VL 3A11 region

<400> SEQUENCE: 50

Asp Ile Val Leu Thr Gln Ser Pro Gly Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asp Ile His
65                  70                  75                  80

Pro Met Glu Glu Asp Asp Thr Ala Met Tyr Phe Cys Gln Gln Ser Lys
                85                  90                  95

Glu Val Pro Pro Thr Phe Gly Gly Gly Thr Lys Leu Glu Ile Lys Arg
            100                 105                 110

<210> SEQ ID NO 51
<211> LENGTH: 120
<212> TYPE: PRT
<213> ORGANISM: Mouse
<220> FEATURE:
<221> NAME/KEY: PEPTIDE
<222> LOCATION: (1)..(120)
<223> OTHER INFORMATION: Amino Acid Sequence of VH 4B4 region

<400> SEQUENCE: 51

Gln Val Thr Leu Lys Glu Ser Gly Pro Gly Ile Leu Lys Pro Ser Gln
1               5                   10                  15

Thr Leu Ser Leu Thr Cys Ser Leu Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Trp Trp Asp Gly Asp Ser Tyr Ser Asn Pro Ser
    50                  55                  60

Leu Arg Ser Arg Leu Thr Ile Ser Arg Asp Thr Ser Arg Asn Gln Val
```

-continued

```
                65                  70                  75                  80
Phe Leu Arg Ile Ala Thr Val Asp Thr Ala Asp Thr Ala Thr Tyr Tyr
                        85                  90                  95

Cys Ala Arg Arg Thr Arg Val Asn Tyr Ala Met Asp Tyr Trp Gly Gln
                        100                 105                 110

Gly Thr Ser Val Thr Val Ser Ser
                        115                 120

<210> SEQ ID NO 52
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 4B4 region

<400> SEQUENCE: 52

Ser Val Val Met Thr Gln Thr Pro Lys Phe Leu Leu Val Ser Ala Gly
1               5                   10                  15

Asp Arg Val Thr Met Thr Cys Lys Ala Ser Gln Ser Val Ser Asn Asp
                20                  25                  30

Val Ala Trp Phe Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Asn Ser Pro Trp
                85                  90                  95

Thr Phe Gly Gly Gly Thr Lys Leu Glu Ile Lys Arg
                100                 105

<210> SEQ ID NO 53
<211> LENGTH: 118
<212> TYPE: PRT
<213> ORGANISM: Mouse
<220> FEATURE:
<221> NAME/KEY: PEPTIDE
<222> LOCATION: (1)..(118)
<223> OTHER INFORMATION: Amino Acid Sequence of VH 7G3 region

<400> SEQUENCE: 53

Glu Val Gln Leu Gln Gln Ser Gly Ala Glu Phe Val Arg Ser Gly Ala
1               5                   10                  15

Ser Val Lys Leu Ser Cys Thr Ala Ser Gly Leu Asn Ile Lys Asp Tyr
                20                  25                  30

Tyr Ile His Trp Val Lys Gln Arg Pro Glu Gln Val Leu Asp Trp Ile
            35                  40                  45

Gly Trp Ile Asp Pro Glu Asn Gly Tyr Ser Glu Tyr Ala Pro Arg Phe
    50                  55                  60

Gln Asp Lys Ala Thr Met Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Asn Pro Gly Glu Leu Ala Arg Tyr Phe Asp Tyr Trp Gly Gln Gly Thr
                100                 105                 110

Thr Leu Thr Val Ser Ser
            115
```

```
<210> SEQ ID NO 54
<211> LENGTH: 108
<212> TYPE: PRT
<213> ORGANISM: Mouse
<220> FEATURE:
<221> NAME/KEY: PEPTIDE
<222> LOCATION: (1)..(108)
<223> OTHER INFORMATION: Amino Acid Sequence of VL 7G3 region

<400> SEQUENCE: 54

Asp Ile Val Leu Ser Gln Ser Pro Ala Thr Leu Ser Val Thr Pro Gly
1               5                   10                  15

Asp Ser Val Ser Leu Ser Cys Arg Ala Ser Gln Ser Ile Ser Lys Asn
            20                  25                  30

Leu His Trp Tyr Gln Gln Lys Ser His Glu Ser Pro Arg Leu Leu Ile
        35                  40                  45

Lys Tyr Thr Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Ile Ser Trp Pro Leu
                85                  90                  95

Thr Phe Gly Ala Gly Thr Lys Leu Glu Leu Lys Arg
            100                 105

<210> SEQ ID NO 55
<211> LENGTH: 7
<212> TYPE: PRT
<213> ORGANISM: Artificial
<220> FEATURE:
<223> OTHER INFORMATION: Mouse IgG Consensus IL-12p40 CDR affinity
      ligand amino acid sequence
<220> FEATURE:
<221> NAME/KEY: PEPTIDE
<222> LOCATION: (1)..(1)
<223> OTHER INFORMATION: Xaa= Asp, Lys, Thr, Ser
<220> FEATURE:
<221> NAME/KEY: PEPTIDE
<222> LOCATION: (2)..(2)
<223> OTHER INFORMATION: Xaa= Tyr, Ser, Thr
<220> FEATURE:
<221> NAME/KEY: PEPTIDE
<222> LOCATION: (3)..(3)
<223> OTHER INFORMATION: Xaa= Tyr, Val, Gly, Trp, Ser, Phe
<220> FEATURE:
<221> NAME/KEY: PEPTIDE
<222> LOCATION: (4)..(4)
<223> OTHER INFORMATION: Xaa= Ile, Met
<220> FEATURE:
<221> NAME/KEY: PEPTIDE
<222> LOCATION: (5)..(5)
<223> OTHER INFORMATION: Xaa= His, Gly, Glu, Val
<220> FEATURE:
<221> NAME/KEY: PEPTIDE
<222> LOCATION: (6)..(6)
<223> OTHER INFORMATION: Xaa= Val or Not Present
<220> FEATURE:
<221> NAME/KEY: PEPTIDE
<222> LOCATION: (7)..(7)
<223> OTHER INFORMATION: Xaa= Ser or Not Present

<400> SEQUENCE: 55

Xaa Xaa Xaa Xaa Xaa Xaa Xaa
1               5

<210> SEQ ID NO 56
<211> LENGTH: 20
<212> TYPE: PRT
<213> ORGANISM: Artificial
```

```
<220> FEATURE:
<223> OTHER INFORMATION: Mouse IgG Consensus Il-12p40 CDR affinity
      ligand amino acid sequence
<220> FEATURE:
<221> NAME/KEY: PEPTIDE
<222> LOCATION: (1)..(1)
<223> OTHER INFORMATION: Xaa = His, Asp, Gly, Trp, Ser, Tyr, Arg
<220> FEATURE:
<221> NAME/KEY: PEPTIDE
<222> LOCATION: (2)..(2)
<223> OTHER INFORMATION: Xaa = Ile, Phe
<220> FEATURE:
<221> NAME/KEY: PEPTIDE
<222> LOCATION: (3)..(3)
<223> OTHER INFORMATION: Xaa = Tyr, Trp, Leu, Ser, Asn, Asp, Gly
<220> FEATURE:
<221> NAME/KEY: PEPTIDE
<222> LOCATION: (4)..(4)
<223> OTHER INFORMATION: Xaa = Trp, Pro, His, Thr, Ser
<220> FEATURE:
<221> NAME/KEY: PEPTIDE
<222> LOCATION: (5)..(5)
<223> OTHER INFORMATION: Xaa = Asp, Gly, Glu, Ala, Ile
<220> FEATURE:
<221> NAME/KEY: PEPTIDE
<222> LOCATION: (6)..(6)
<223> OTHER INFORMATION: Xaa = Asp, Gly, Ser, Thr, Asn
<220> FEATURE:
<221> NAME/KEY: PEPTIDE
<222> LOCATION: (7)..(7)
<223> OTHER INFORMATION: Xaa = Asp, Gly, Ser, Pro
<220> FEATURE:
<221> NAME/KEY: PEPTIDE
<222> LOCATION: (8)..(8)
<223> OTHER INFORMATION: Xaa = Lys, Asn, Ser, Glu, Thr, His
<220> FEATURE:
<221> NAME/KEY: PEPTIDE
<222> LOCATION: (9)..(9)
<223> OTHER INFORMATION: Xaa = Tyr, Thr, Pro, Ile, Asn
<220> FEATURE:
<221> NAME/KEY: PEPTIDE
<222> LOCATION: (10)..(10)
<223> OTHER INFORMATION: Xaa = Tyr,  Asn, Thr, His, Lys, Ser, Gly
<220> FEATURE:
<221> NAME/KEY: PEPTIDE
<222> LOCATION: (11)..(11)
<223> OTHER INFORMATION: Xaa = Asn, Tyr
<220> FEATURE:
<221> NAME/KEY: PEPTIDE
<222> LOCATION: (12)..(12)
<223> OTHER INFORMATION: Xaa = Pro, Asn, Ala, Asp, Ser
<220> FEATURE:
<221> NAME/KEY: PEPTIDE
<222> LOCATION: (13)..(13)
<223> OTHER INFORMATION: Xaa = Ser, Glu, Asp, Pro
<220> FEATURE:
<221> NAME/KEY: PEPTIDE
<222> LOCATION: (14)..(14)
<223> OTHER INFORMATION: Xaa = Leu, Lys, Asp, Thr, Tyr
<220> FEATURE:
<221> NAME/KEY: PEPTIDE
<222> LOCATION: (15)..(15)
<223> OTHER INFORMATION: Xaa = Lys, Phe, Val, Met, Arg, Ala
<220> FEATURE:
<221> NAME/KEY: PEPTIDE
<222> LOCATION: (16)..(16)
<223> OTHER INFORMATION: Xaa = Ser, Lys, Gln, Pro, or Not Present
<220> FEATURE:
<221> NAME/KEY: PEPTIDE
<222> LOCATION: (17)..(17)
<223> OTHER INFORMATION: Xaa = Asp, Gly, Arg, or Not Present
<220> FEATURE:
<221> NAME/KEY: PEPTIDE
<222> LOCATION: (18)..(18)
<223> OTHER INFORMATION: Xaa = Phe, or Not Present
<220> FEATURE:
<221> NAME/KEY: PEPTIDE
<222> LOCATION: (19)..(19)
<223> OTHER INFORMATION: Xaa = Gln, or Not Present
<220> FEATURE:
```

-continued

```
<221> NAME/KEY: PEPTIDE
<222> LOCATION: (20)..(20)
<223> OTHER INFORMATION: Xaa = Asp, or Not Present

<400> SEQUENCE: 56

Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 57
<211> LENGTH: 13
<212> TYPE: PRT
<213> ORGANISM: Artificial
<220> FEATURE:
<223> OTHER INFORMATION: Mouse IgG Consensus Il-12p40 CDR affinity
      ligand amino acid sequence
<220> FEATURE:
<221> NAME/KEY: PEPTIDE
<222> LOCATION: (1)..(1)
<223> OTHER INFORMATION: Xaa= Arg, Asn, Trp
<220> FEATURE:
<221> NAME/KEY: PEPTIDE
<222> LOCATION: (2)..(2)
<223> OTHER INFORMATION: Xaa= Gly, Thr, Arg, Pro, His
<220> FEATURE:
<221> NAME/KEY: PEPTIDE
<222> LOCATION: (3)..(3)
<223> OTHER INFORMATION: Xaa= Ile, Arg, Phe, Tyr, Gln
<220> FEATURE:
<221> NAME/KEY: PEPTIDE
<222> LOCATION: (4)..(4)
<223> OTHER INFORMATION: Xaa= Arg, Val,Tyr, Phe, Ala
<220> FEATURE:
<221> NAME/KEY: PEPTIDE
<222> LOCATION: (5)..(5)
<223> OTHER INFORMATION: Xaa= Ser, Asn, Gly, Ala, Arg
<220> FEATURE:
<221> NAME/KEY: PEPTIDE
<222> LOCATION: (6)..(6)
<223> OTHER INFORMATION: Xaa= Ala, Tyr, Leu, Phe, Met
<220> FEATURE:
<221> NAME/KEY: PEPTIDE
<222> LOCATION: (7)..(7)
<223> OTHER INFORMATION: Xaa= Met, Ala, Asp, Leu, Phe
<220> FEATURE:
<221> NAME/KEY: PEPTIDE
<222> LOCATION: (8)..(8)
<223> OTHER INFORMATION: Xaa= Asp, Met, Tyr, Trp
<220> FEATURE:
<221> NAME/KEY: PEPTIDE
<222> LOCATION: (9)..(9)
<223> OTHER INFORMATION: Xaa= Tyr, Asp, Asn
<220> FEATURE:
<221> NAME/KEY: PEPTIDE
<222> LOCATION: (10)..(10)
<223> OTHER INFORMATION: Xaa= Tyr, Ala, or Not Present
<220> FEATURE:
<221> NAME/KEY: PEPTIDE
<222> LOCATION: (11)..(11)
<223> OTHER INFORMATION: Xaa= Met, or  Not Present
<220> FEATURE:
<221> NAME/KEY: PEPTIDE
<222> LOCATION: (12)..(12)
<223> OTHER INFORMATION: Xaa= Asp, or  Not Present
<220> FEATURE:
<221> NAME/KEY: PEPTIDE
<222> LOCATION: (13)..(13)
<223> OTHER INFORMATION: Xaa= Tyr, or  Not Present

<400> SEQUENCE: 57

Xaa Xaa Xaa Xaa Xaa Xaa Xaa Xaa Xaa Xaa Xaa Xaa Xaa
1               5                   10

<210> SEQ ID NO 58
```

```
<211> LENGTH: 15
<212> TYPE: PRT
<213> ORGANISM: Artificial
<220> FEATURE:
<223> OTHER INFORMATION: Mouse IgG Consensus Il-12p40 CDR affinity
      ligand amino acid sequence
<220> FEATURE:
<221> NAME/KEY: PEPTIDE
<222> LOCATION: (1)..(1)
<223> OTHER INFORMATION: Xaa = Lys or Arg
<220> FEATURE:
<221> NAME/KEY: PEPTIDE
<222> LOCATION: (2)..(2)
<223> OTHER INFORMATION: Xaa = Ala
<220> FEATURE:
<221> NAME/KEY: PEPTIDE
<222> LOCATION: (3)..(3)
<223> OTHER INFORMATION: Xaa = Ser
<220> FEATURE:
<221> NAME/KEY: PEPTIDE
<222> LOCATION: (4)..(4)
<223> OTHER INFORMATION: Xaa = Gln, Glu
<220> FEATURE:
<221> NAME/KEY: PEPTIDE
<222> LOCATION: (5)..(5)
<223> OTHER INFORMATION: Xaa = Ser, Asn
<220> FEATURE:
<221> NAME/KEY: PEPTIDE
<222> LOCATION: (6)..(6)
<223> OTHER INFORMATION: Xaa = Val, Ile
<220> FEATURE:
<221> NAME/KEY: PEPTIDE
<222> LOCATION: (7)..(7)
<223> OTHER INFORMATION: Xaa = Ser, Gly, Asp
<220> FEATURE:
<221> NAME/KEY: PEPTIDE
<222> LOCATION: (8)..(8)
<223> OTHER INFORMATION: Xaa = Asn, Thr, Lys
<220> FEATURE:
<221> NAME/KEY: PEPTIDE
<222> LOCATION: (9)..(9)
<223> OTHER INFORMATION: Xaa = Asp, Asn, Tyr
<220> FEATURE:
<221> NAME/KEY: PEPTIDE
<222> LOCATION: (10)..(10)
<223> OTHER INFORMATION: Xaa = Val, Gly, Leu
<220> FEATURE:
<221> NAME/KEY: PEPTIDE
<222> LOCATION: (11)..(11)
<223> OTHER INFORMATION: Xaa = Ala, Ile, His
<220> FEATURE:
<221> NAME/KEY: PEPTIDE
<222> LOCATION: (12)..(12)
<223> OTHER INFORMATION: Xaa = Ser, or Not Present
<220> FEATURE:
<221> NAME/KEY: PEPTIDE
<222> LOCATION: (13)..(13)
<223> OTHER INFORMATION: Xaa = Phe, or Not Present
<220> FEATURE:
<221> NAME/KEY: PEPTIDE
<222> LOCATION: (14)..(14)
<223> OTHER INFORMATION: Xaa = Met, or Not Present
<220> FEATURE:
<221> NAME/KEY: PEPTIDE
<222> LOCATION: (15)..(15)
<223> OTHER INFORMATION: Xaa = Asn, or Not Present

<400> SEQUENCE: 58

Xaa Xaa Xaa Xaa Xaa Xaa Xaa Xaa Xaa Xaa Xaa Xaa Xaa Xaa Xaa
1               5                   10                  15

<210> SEQ ID NO 59
<211> LENGTH: 8
<212> TYPE: PRT
<213> ORGANISM: Artificial
<220> FEATURE:
<223> OTHER INFORMATION: Mouse IgG Consensus Il-12p40 CDR affinity
      ligand amino acid sequence
```

```
<220> FEATURE:
<221> NAME/KEY: PEPTIDE
<222> LOCATION: (1)..(1)
<223> OTHER INFORMATION: Xaa = Tyr, Ser
<220> FEATURE:
<221> NAME/KEY: PEPTIDE
<222> LOCATION: (2)..(2)
<223> OTHER INFORMATION: Xaa = Ala, Thr
<220> FEATURE:
<221> NAME/KEY: PEPTIDE
<222> LOCATION: (3)..(3)
<223> OTHER INFORMATION: Xaa = Ser, Ala
<220> FEATURE:
<221> NAME/KEY: PEPTIDE
<222> LOCATION: (4)..(4)
<223> OTHER INFORMATION: Xaa = Asn, His, Ser,Gln
<220> FEATURE:
<221> NAME/KEY: PEPTIDE
<222> LOCATION: (5)..(5)
<223> OTHER INFORMATION: Xaa = Arg, Asn, Ser
<220> FEATURE:
<221> NAME/KEY: PEPTIDE
<222> LOCATION: (6)..(6)
<223> OTHER INFORMATION: Xaa = Tyr, Gln, Ile
<220> FEATURE:
<221> NAME/KEY: PEPTIDE
<222> LOCATION: (7)..(7)
<223> OTHER INFORMATION: Xaa = Thr, Ser, Gly
<220> FEATURE:
<221> NAME/KEY: PEPTIDE
<222> LOCATION: (8)..(8)
<223> OTHER INFORMATION: Xaa = Ser, or Not Present

<400> SEQUENCE: 59

Xaa Xaa Xaa Xaa Xaa Xaa Xaa Xaa
1               5

<210> SEQ ID NO 60
<211> LENGTH: 9
<212> TYPE: PRT
<213> ORGANISM: Artificial
<220> FEATURE:
<223> OTHER INFORMATION: Mouse IgG Consensus Il-12p40 CDR affinity
      ligand amino acid sequence
<220> FEATURE:
<221> NAME/KEY: PEPTIDE
<222> LOCATION: (1)..(1)
<223> OTHER INFORMATION: Xaa = Gln
<220> FEATURE:
<221> NAME/KEY: PEPTIDE
<222> LOCATION: (2)..(2)
<223> OTHER INFORMATION: Xaa = Gln
<220> FEATURE:
<221> NAME/KEY: PEPTIDE
<222> LOCATION: (3)..(3)
<223> OTHER INFORMATION: Xaa = Asp, Tyr, Ser
<220> FEATURE:
<221> NAME/KEY: PEPTIDE
<222> LOCATION: (4)..(4)
<223> OTHER INFORMATION: Xaa = Tyr, Asn, Lys, Ile
<220> FEATURE:
<221> NAME/KEY: PEPTIDE
<222> LOCATION: (5)..(5)
<223> OTHER INFORMATION: Xaa = Asn, Thr, Ser, Glu
<220> FEATURE:
<221> NAME/KEY: PEPTIDE
<222> LOCATION: (6)..(6)
<223> OTHER INFORMATION: Xaa = Ser, Tyr, Val, Trp
<220> FEATURE:
<221> NAME/KEY: PEPTIDE
<222> LOCATION: (7)..(7)
<223> OTHER INFORMATION: Xaa = Pro
<220> FEATURE:
<221> NAME/KEY: PEPTIDE
<222> LOCATION: (8)..(8)
<223> OTHER INFORMATION: Xaa = Trp, Phe, Tyr, Leu, Pro
<220> FEATURE:
<221> NAME/KEY: PEPTIDE
```

```
<222> LOCATION: (9)..(9)
<223> OTHER INFORMATION: Xaa = Thr, Ser

<400> SEQUENCE: 60

Xaa Xaa Xaa Xaa Xaa Xaa Xaa Xaa Xaa
1               5

<210> SEQ ID NO 61
<211> LENGTH: 119
<212> TYPE: PRT
<213> ORGANISM: Artificial
<220> FEATURE:
<223> OTHER INFORMATION: Amino Acid Sequence of VH 1D4.1 region

<400> SEQUENCE: 61

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly Ile Arg Ser Ala Met Asp Tyr Trp Gly Gln Gly
            100                 105                 110

Thr Thr Val Thr Val Ser Ser
        115

<210> SEQ ID NO 62
<211> LENGTH: 108
<212> TYPE: PRT
<213> ORGANISM: Artificial
<220> FEATURE:
<223> OTHER INFORMATION: Amino Acid Sequence of VL 1D4.1 region

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 63
<211> LENGTH: 119
<212> TYPE: PRT
<213> ORGANISM: Artificial
<220> FEATURE:
<223> OTHER INFORMATION: Amino Acid Sequence of VH 1D4.2 region
```

```
<400> SEQUENCE: 63

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Lys Tyr Tyr Asn Pro Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Arg Gly Ile Arg Ser Ala Met Asp Tyr Trp Gly Gln Gly
            100                 105                 110

Thr Thr Val Thr Val Ser Ser
            115

<210> SEQ ID NO 64
<211> LENGTH: 108
<212> TYPE: PRT
<213> ORGANISM: Artificial
<220> FEATURE:
<223> OTHER INFORMATION: Amino Acid Sequence of VL 1D4.2 region

<400> SEQUENCE: 64

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 65
<211> LENGTH: 119
<212> TYPE: PRT
<213> ORGANISM: Artificial
<220> FEATURE:
<223> OTHER INFORMATION: Amino Acid Sequence of VH 1D4.3 region

<400> SEQUENCE: 65

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Lys Tyr Tyr Asn Pro Ser
    50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gly Ile Arg Ser Ala Met Asp Tyr Trp Gly Gln Gly
            100                 105                 110

Thr Thr Val Thr Val Ser Ser
            115

<210> SEQ ID NO 66
<211> LENGTH: 108
<212> TYPE: PRT
<213> ORGANISM: Artificial
<220> FEATURE:
<223> OTHER INFORMATION: Amino Acid Sequence of VL 1D4.3 region

<400> SEQUENCE: 66

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Ser Val Ser Asn Asp
             20                  25                  30

Val Ala Trp Tyr Gln Gln Lys Pro Gly Gln Ala Pro Arg Leu Leu Ile
         35                  40                  45

Tyr Tyr Ala Ser Asn Arg Tyr Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Asp Tyr Asn Ser Pro Trp
                 85                  90                  95

Thr Phe Gly Gly Gly Thr Lys Val Glu Ile Lys Arg
            100                 105

<210> SEQ ID NO 67
<211> LENGTH: 120
<212> TYPE: PRT
<213> ORGANISM: Artificial
<220> FEATURE:
<223> OTHER INFORMATION: Amino Acid Sequence of VH 1A6.1 region

<400> SEQUENCE: 67

Glu Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Ala Leu Glu
         35                  40                  45

Trp Leu Ala His Ile Trp Trp Asp Gly Asp Asn Tyr Tyr Asn Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Thr Arg Val Asn Tyr Ala Met Asp Tyr Trp Gly Gln
            100                 105                 110

Gly Thr Thr Val Thr Val Ser Ser
            115                 120

<210> SEQ ID NO 68
<211> LENGTH: 108
```

```
<212> TYPE: PRT
<213> ORGANISM: Artificial
<220> FEATURE:
<223> OTHER INFORMATION: Amino Acid Sequence of VL 1A6.1 region

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 69
<211> LENGTH: 120
<212> TYPE: PRT
<213> ORGANISM: Artificial
<220> FEATURE:
<223> OTHER INFORMATION: Amino Acid Sequence of VH 1A6.2 region

<400> SEQUENCE: 69

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Trp Trp Asp Gly Asp Asn Tyr Tyr Asn Pro Ser
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Arg Thr Arg Val Ser Tyr Ala Met Asp Tyr Trp Gly Gln
            100                 105                 110

Gly Thr Thr Val Thr Val Ser Ser
        115                 120

<210> SEQ ID NO 70
<211> LENGTH: 108
<212> TYPE: PRT
<213> ORGANISM: Artificial
<220> FEATURE:
<223> OTHER INFORMATION: Amino Acid Sequence of VL 1A6.2 region

<400> SEQUENCE: 70

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45
```

```
Tyr Tyr Ala Ser Asn Arg Tyr Thr Gly Ile Pro Ala Arg Phe Ser Gly
        50                  55                  60

Ser Gly Ser Gly Thr Glu Phe Thr Leu Thr Ile Ser Ser Leu Gln Ser
 65              70                  75                      80

Glu Asp Phe Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105
```

<210> SEQ ID NO 71
<211> LENGTH: 112
<212> TYPE: PRT
<213> ORGANISM: Artificial
<220> FEATURE:
<223> OTHER INFORMATION: Amino Acid Sequence of VH 8E1.1 region

<400> SEQUENCE: 71

```
Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Gly Met Val Trp Val Arg Gln Ala Pro Gly Lys Gly Leu Glu Trp Val
         35                  40                  45

Gly Ser Ile Ser Ser Gly Ser Ser Asn Ile Tyr Tyr Ala Asp Thr Val
     50                  55                  60

Lys Gly Arg Phe Thr Ile Ser Arg Asp Asp Ser Lys Asn Ser Leu Tyr
 65                  70                  75                  80

Leu Gln Met Asn Ser Leu Lys Thr Glu Asp Thr Ala Val Tyr Tyr Cys
                 85                  90                  95

Ala Arg Asn Pro Tyr Trp Gly Gln Gly Thr Thr Val Thr Val Ser Ser
            100                 105                 110
```

<210> SEQ ID NO 72
<211> LENGTH: 108
<212> TYPE: PRT
<213> ORGANISM: Artificial
<220> FEATURE:
<223> OTHER INFORMATION: Amino Acid Sequence of VL 8E1.1 region

<400> SEQUENCE: 72

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Thr Asn
             20                  25                  30

Val Ala Trp Tyr Gln Gln Lys Pro Glu Lys Ala Pro Lys Ser Leu Ile
         35                  40                  45

Tyr Ser Ala Ser His Arg Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Arg
            100                 105
```

<210> SEQ ID NO 73
<211> LENGTH: 112
<212> TYPE: PRT
<213> ORGANISM: Artificial

```
<220> FEATURE:
<223> OTHER INFORMATION: Amino Acid Sequence of VH 8E1.2 region

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ser Ser Ile Ser Ser Gly Ser Ser Asn Ile Tyr Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Pro Tyr Trp Gly Gln Gly Thr Thr Val Thr Val Ser Ser
            100                 105                 110

<210> SEQ ID NO 74
<211> LENGTH: 108
<212> TYPE: PRT
<213> ORGANISM: Artificial
<220> FEATURE:
<223> OTHER INFORMATION: Amino Acid Sequence of VL 8E1.2 region

<400> SEQUENCE: 74

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Leu Leu Ile
        35                  40                  45

Tyr Ser Ala Ser His Arg Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 75
<211> LENGTH: 117
<212> TYPE: PRT
<213> ORGANISM: Artificial
<220> FEATURE:
<223> OTHER INFORMATION: Amino Acid Sequence of VH 3G7.1 region

<400> SEQUENCE: 75

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Trp Ile Glu Trp Val Arg Gln Ala Pro Gly Gln Gly Leu Glu Trp Met
        35                  40                  45

Gly Gly Phe Ser His Gly Ser Gly Ser Thr Asn Tyr Asn Glu Lys Phe
50                  55                  60

Lys Gly Arg Val Thr Ile Thr Ala Asp Lys Ser Thr Ser Thr Ala Tyr
```

```
                    65                  70                  75                  80
Met Glu Leu Ser Ser Leu Arg Ser Glu Asp Thr Ala Val Tyr Tyr Cys
                        85                  90                  95

Ala Arg Arg Arg Phe Arg Gly Met Asp Tyr Trp Gly Gln Gly Thr Thr
                100                 105                 110

Val Thr Val Ser Ser
            115

<210> SEQ ID NO 76
<211> LENGTH: 108
<212> TYPE: PRT
<213> ORGANISM: Artificial
<220> FEATURE:
<223> OTHER INFORMATION: Amino Acid Sequence of VL 3G7.1 region

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Trp
                85                  90                  95

Ser Phe Gly Gly Gly Thr Lys Val Glu Ile Lys Arg
            100                 105

<210> SEQ ID NO 77
<211> LENGTH: 117
<212> TYPE: PRT
<213> ORGANISM: Artificial
<220> FEATURE:
<223> OTHER INFORMATION: Amino Acid Sequence of VH 3G7.2 region

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Ile Glu Trp Val Arg Gln Ala Pro Gly Gln Gly Leu Glu Trp Met
            35                  40                  45

Gly Gly Phe Ser His Gly Ser Gly Ser Thr Asn Tyr Asn Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Arg Phe Arg Gly Met Asp Tyr Trp Gly Gln Gly Thr Thr
                100                 105                 110

Val Thr Val Ser Ser
            115

<210> SEQ ID NO 78
<211> LENGTH: 108
<212> TYPE: PRT
```

```
<213> ORGANISM: Artificial
<220> FEATURE:
<223> OTHER INFORMATION: Amino Acid Sequence of VL 3G7.2 region

<400> SEQUENCE: 78

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Ser Ser Pro Trp
                85                  90                  95

Ser Phe Gly Gly Gly Thr Lys Val Glu Ile Lys Arg
            100                 105

<210> SEQ ID NO 79
<211> LENGTH: 108
<212> TYPE: PRT
<213> ORGANISM: Artificial
<220> FEATURE:
<223> OTHER INFORMATION: Amino Acid Sequence of VL 1A6.9 region

<400> SEQUENCE: 79

Ser Val Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Phe Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 80
<211> LENGTH: 119
<212> TYPE: PRT
<213> ORGANISM: Artificial
<220> FEATURE:
<223> OTHER INFORMATION: Amino Acid Sequence of VH 1D4.6 region

<400> SEQUENCE: 80

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Lys Tyr Tyr Asn Pro Ser
50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Thr Arg Arg Gly Ile Arg Ser Ala Met Asp Tyr Trp Gly Gln Gly
                100                 105                 110

Thr Thr Val Thr Val Ser Ser
                115

<210> SEQ ID NO 81
<211> LENGTH: 108
<212> TYPE: PRT
<213> ORGANISM: Artificial
<220> FEATURE:
<223> OTHER INFORMATION: Amino Acid Sequence of VL 1D4.6 region

<400> SEQUENCE: 81

Asp Val Val Met Thr Gln Ser Pro Asp Ser Leu Ala Val Ser Leu Gly
  1               5                  10                  15

Glu Arg Ala Thr Ile Asn Cys Lys Ala Ser Gln Ser Val Ser Asn Asp
                 20                  25                  30

Val Ala Trp Tyr Gln Gln Lys Pro Gly Gln Pro Lys Leu Leu Ile
             35                  40                  45

Tyr Tyr Ala Ser Asn Arg Tyr Thr Gly Val Pro Asp Arg Phe Ser Gly
 50                  55                  60

Ser Gly Tyr Gly Thr Asp Phe Thr Leu Thr Ile Ser Ser Leu Gln Ala
 65                  70                  75                  80

Glu Asp Val Ala Val Tyr Tyr Cys Gln Gln Asp Tyr Asn Ser Pro Trp
                 85                  90                  95

Thr Phe Gly Gly Gly Thr Lys Val Glu Ile Lys Arg
                100                 105

<210> SEQ ID NO 82
<211> LENGTH: 119
<212> TYPE: PRT
<213> ORGANISM: Artificial
<220> FEATURE:
<223> OTHER INFORMATION: Amino Acid Sequence of VH 1D4.7 region

<400> SEQUENCE: 82

Glu Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Arg Lys Ser
                 20                  25                  30

Val Met Gly Val Ser Trp Ile Arg Gln Pro Pro Gly Lys Ala Leu Glu
             35                  40                  45

Trp Leu Ala His Ile Tyr Trp Asp Asp Lys Tyr Tyr Asn Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Thr Arg Arg Gly Ile Arg Ser Ala Met Asp Tyr Trp Gly Gln Gly
                100                 105                 110

Thr Thr Val Thr Val Ser Ser
                115

<210> SEQ ID NO 83
<211> LENGTH: 108
```

```
<212> TYPE: PRT
<213> ORGANISM: Artificial
<220> FEATURE:
<223> OTHER INFORMATION: Amino Acid Sequence of VL 1D4.7 region

<400> SEQUENCE: 83

Asp Val Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Ala Ser Asn Arg Tyr Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 84
<211> LENGTH: 119
<212> TYPE: PRT
<213> ORGANISM: Artificial
<220> FEATURE:
<223> OTHER INFORMATION: Amino Acid Sequence of VH 1D4.8 region

<400> SEQUENCE: 84

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Arg Lys Ser
            20                  25                  30

Val Met Gly Val Ser Trp Ile Arg Gln Pro Pro Gly Lys Ala Leu Glu
        35                  40                  45

Trp Leu Ala His Ile Tyr Trp Asp Asp Asp Lys Tyr Tyr Asn Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr Arg Arg Gly Ile Arg Ser Ala Met Asp Tyr Trp Gly Gln Gly
            100                 105                 110

Thr Thr Val Thr Val Ser Ser
        115

<210> SEQ ID NO 85
<211> LENGTH: 108
<212> TYPE: PRT
<213> ORGANISM: Artificial
<220> FEATURE:
<223> OTHER INFORMATION: Amino Acid Sequence of VL 1D4.8 region

<400> SEQUENCE: 85

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45
```

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 86
<211> LENGTH: 119
<212> TYPE: PRT
<213> ORGANISM: Artificial
<220> FEATURE:
<223> OTHER INFORMATION: Amino Acid Sequence of VH 1D4.9 region

<400> SEQUENCE: 86

Glu Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Arg Lys Ser
                20                  25                  30

Val Met Gly Val Ser Trp Ile Arg Gln Pro Pro Gly Lys Ala Leu Glu
            35                  40                  45

Trp Leu Ala His Ile Tyr Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Thr Arg Arg Gly Ile Arg Ser Ala Met Asp Tyr Trp Gly Gln Gly
            100                 105                 110

Thr Thr Val Thr Val Ser Ser
        115

<210> SEQ ID NO 87
<211> LENGTH: 108
<212> TYPE: PRT
<213> ORGANISM: Artificial
<220> FEATURE:
<223> OTHER INFORMATION: Amino Acid Sequence of VL 1D4.9 region

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 88

-continued

```
<211> LENGTH: 112
<212> TYPE: PRT
<213> ORGANISM: Artificial
<220> FEATURE:
<223> OTHER INFORMATION: Amino Acid Sequence of VH 8E1.3 region

<400> SEQUENCE: 88

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Ser Ile Ser Ser Gly Ser Ser Asn Ile Tyr Tyr Ala Asp Thr Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Asn Pro Tyr Trp Gly Gln Gly Thr Thr Val Thr Val Ser Ser
            100                 105                 110

<210> SEQ ID NO 89
<211> LENGTH: 108
<212> TYPE: PRT
<213> ORGANISM: Artificial
<220> FEATURE:
<223> OTHER INFORMATION: Amino Acid Sequence of VL 8E1.3 region

<400> SEQUENCE: 89

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Glu Lys Ala Pro Lys Ser Leu Ile
        35                  40                  45

Tyr Ser Ala Ser His Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 90
<211> LENGTH: 117
<212> TYPE: PRT
<213> ORGANISM: Artificial
<220> FEATURE:
<223> OTHER INFORMATION: Amino Acid Sequence of VH 3G7.3 region

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Thr Gly Tyr Thr Phe Asn Asp Tyr
            20                  25                  30

Trp Ile Glu Trp Val Arg Gln Ala Pro Gly Gln Gly Leu Glu Trp Met
        35                  40                  45

Gly Gly Phe Ser His Gly Ser Gly Ser Thr Asn Tyr Asn Glu Lys Phe
```

```
                50                  55                  60
Lys Gly Arg Val Thr Met Thr Ala Asp Ser Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Arg Phe Arg Gly Met Asp Tyr Trp Gly Gln Gly Thr Thr
                100                 105                 110

Val Thr Val Ser Ser
            115

<210> SEQ ID NO 91
<211> LENGTH: 108
<212> TYPE: PRT
<213> ORGANISM: Artificial
<220> FEATURE:
<223> OTHER INFORMATION: Amino Acid Sequence of VL 3G7.3 region

<400> SEQUENCE: 91

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Ser Val Ser Asn Asp
                20                  25                  30

Val Ala Trp Tyr Gln Gln Lys Pro Gly Gln Ala Pro Arg Leu Leu Ile
            35                  40                  45

Tyr Tyr Ala Ser Asn Arg Tyr Thr Gly Val Pro Asp Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Asp Tyr Ser Ser Pro Trp
                 85                  90                  95

Ser Phe Gly Gly Gly Thr Lys Val Glu Ile Lys Arg
                100                 105

<210> SEQ ID NO 92
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 92

Gln Val Thr Leu Arg Glu Ser Gly Pro Ala Leu Val Lys Pro Thr Gln
 1               5                  10                  15

Thr Leu Thr Leu Thr Cys Thr Leu Tyr Gly Phe Ser Leu Ser
                20                  25                  30

<210> SEQ ID NO 93
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Heavy Chain Acceptor Sequence (Human)

<400> SEQUENCE: 93

Trp Gly Gln Gly Thr Leu Val Thr Val Ser Ser
 1               5                  10

<210> SEQ ID NO 94
```

```
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Heavy Chain Acceptor Sequence (Human)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 95
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Light Chain Acceptor Sequence (Human)

<400> SEQUENCE: 95

Trp Gly Gln Gly Thr Leu Val Thr Val Ser Ser
1               5                   10

<210> SEQ ID NO 96
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Light Chain Acceptor Sequence (Human)

<400> SEQUENCE: 96

Gly Val Pro Ser Arg Ile Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 97
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Light Chain Acceptor Sequence (Human)

<400> SEQUENCE: 97

Trp Phe Gln Gln Lys Pro Gly Lys Ala Pro Lys Ser Leu Ile Tyr
1               5                   10                  15

<210> SEQ ID NO 98
<211> LENGTH: 120
<212> TYPE: PRT
<213> ORGANISM: Artificial
<220> FEATURE:
<223> OTHER INFORMATION: Amino Acid Sequence of VH 1A6.10 region

<400> SEQUENCE: 98

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30
```

```
Gly Met Gly Val Ser Trp Ile Arg Gln Pro Pro Gly Lys Gly Leu Glu
            35                  40                  45

Trp Leu Ala His Ile Trp Trp Asp Gly Asp Asn Tyr Tyr Asn Pro Ser
 50                  55                  60

Leu Lys Ser Gln Leu Thr Ile Ser Lys Asp Thr Ser Lys Asn Gln Val
 65                  70                  75                  80

Val Leu Lys Leu Thr Ser Val Asp Pro Val Asp Thr Ala Thr Tyr Tyr
                85                  90                  95

Cys Ala Arg Arg Thr Arg Val Asn Tyr Ala Met Asp Tyr Trp Gly Gln
                100                 105                 110

Gly Thr Leu Val Thr Val Ser Ser
            115                 120

<210> SEQ ID NO 99
<211> LENGTH: 108
<212> TYPE: PRT
<213> ORGANISM: Artificial
<220> FEATURE:
<223> OTHER INFORMATION: Amino Acid Sequence of VL 1A6.10 region

<400> SEQUENCE: 99

Asp Ile Gln Met Thr Gln Ser Pro Ser Ser Leu Ser Ala Ser Val Gly
 1               5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Lys Ala Pro Lys Leu Leu Ile
            35                  40                  45

Tyr Tyr Ala Ser Asn Arg Tyr Thr Gly Val Pro Asp Arg Phe Ser Gly
 50                  55                  60

Ser Gly Tyr Gly Thr Asp Phe Thr Phe Thr Ile Ser Ser Leu Gln Pro
 65                  70                  75                  80

Glu Asp Ile Ala Thr Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 100
<211> LENGTH: 120
<212> TYPE: PRT
<213> ORGANISM: Artificial
<220> FEATURE:
<223> OTHER INFORMATION: Amino Acid Sequence of VH 1A6.11 region

<400> SEQUENCE: 100

Glu Val Thr Leu Arg Glu Ser Gly Pro Gly Leu Val Lys Pro Thr Gln
 1               5                   10                  15

Thr Leu Thr Leu Thr Cys Thr Leu Tyr Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Trp Trp Asp Gly Asp Asn Tyr Tyr Asn Pro Ser
 50                  55                  60

Leu Lys Ser Gln Leu Thr Ile Ser Lys Asp Thr Ser Lys Asn Gln Val
 65                  70                  75                  80

Val Leu Lys Leu Thr Ser Val Asp Pro Val Asp Thr Ala Thr Tyr Tyr
                85                  90                  95

Cys Ala Arg Arg Thr Arg Val Asn Tyr Ala Met Asp Tyr Trp Gly Gln
                100                 105                 110
```

```
Gly Thr Leu Val Thr Val Ser Ser
        115                 120

<210> SEQ ID NO 101
<211> LENGTH: 108
<212> TYPE: PRT
<213> ORGANISM: Artificial
<220> FEATURE:
<223> OTHER INFORMATION: Amino Acid Sequence of VL 1A6.11 region

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
50                  55                  60

Ser Gly Tyr Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Asn Ser Pro Trp
                85                  90                  95

Thr Phe Gly Gly Gly Thr Lys Val Glu Ile Lys Arg
            100                 105

<210> SEQ ID NO 102
<211> LENGTH: 120
<212> TYPE: PRT
<213> ORGANISM: Artificial
<220> FEATURE:
<223> OTHER INFORMATION: Amino Acid Sequence of VH 1A6.12 region

<400> SEQUENCE: 102

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Trp Trp Asp Gly Asp Asn Tyr Tyr Asn Pro Ser
50                  55                  60

Leu Lys Ser Gln Leu Thr Ile Ser Lys Asp Thr Ser Lys Asn Gln Val
65                  70                  75                  80

Val Leu Lys Leu Thr Ser Val Asp Pro Val Asp Thr Ala Thr Tyr Tyr
                85                  90                  95

Cys Ala Arg Arg Thr Arg Val Asn Tyr Ala Met Asp Tyr Trp Gly Gln
            100                 105                 110

Gly Thr Leu Val Thr Val Ser Ser
        115                 120

<210> SEQ ID NO 103
<211> LENGTH: 108
<212> TYPE: PRT
<213> ORGANISM: Artificial
<220> FEATURE:
<223> OTHER INFORMATION: Amino Acid Sequence of VL 1A6.12 region

<400> SEQUENCE: 103

Asp Ile Gln Met Thr Gln Ser Pro Ser Ser Leu Ser Ala Ser Val Gly
1               5                   10                  15
```

Asp Arg Val Thr Ile Thr Cys Lys Ala Ser Gln Ser Val Ser Asn Asp
             20                  25                  30

Val Ala Trp Phe Gln Gln Lys Pro Gly Lys Ala Pro Lys Leu Leu Ile
         35                  40                  45

Tyr Tyr Ala Ser Asn Arg Tyr Thr Gly Val Pro Asp Arg Phe Ser Gly
 50                  55                  60

Ser Gly Tyr Gly Thr Asp Phe Thr Phe Thr Ile Ser Ser Leu Gln Pro
65                  70                  75                  80

Glu Asp Ile Ala Thr Tyr Tyr Cys Gln Gln Asp Tyr Asn Ser Pro Trp
             85                  90                  95

Thr Phe Gly Gly Gly Thr Lys Val Glu Ile Lys Arg
            100                 105

<210> SEQ ID NO 104
<211> LENGTH: 112
<212> TYPE: PRT
<213> ORGANISM: Artificial
<220> FEATURE:
<223> OTHER INFORMATION: Amino Acid Sequence of VH 8E1.4 region

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
             20                  25                  30

Gly Met Val Trp Val Arg Gln Ala Pro Gly Lys Gly Leu Glu Trp Val
         35                  40                  45

Ala Ser Ile Ser Ser Gly Ser Ser Asn Ile Tyr Tyr Ala Asp Thr Val
 50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
             85                  90                  95

Ala Arg Asn Pro Tyr Trp Gly Gln Gly Thr Leu Val Thr Val Ser Ser
            100                 105                 110

<210> SEQ ID NO 105
<211> LENGTH: 108
<212> TYPE: PRT
<213> ORGANISM: Artificial
<220> FEATURE:
<223> OTHER INFORMATION: Amino Acid Sequence of VL 8E1.4 region

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
             20                  25                  30

Val Ala Trp Tyr Gln Gln Lys Pro Gly Lys Ala Pro Lys Gly Leu Ile
         35                  40                  45

Tyr Ser Ala Ser His Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
             85                  90                  95

Thr Phe Gly Gly Gly Thr Lys Val Glu Ile Lys Arg
            100                 105

```
<210> SEQ ID NO 106
<211> LENGTH: 112
<212> TYPE: PRT
<213> ORGANISM: Artificial
<220> FEATURE:
<223> OTHER INFORMATION: Amino Acid Sequence of VH 8E1.5 region

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
        35                  40                  45

Ala Ser Ile Ser Ser Gly Ser Ser Asn Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Pro Tyr Trp Gly Gln Gly Thr Leu Val Thr Val Ser Ser
            100                 105                 110

<210> SEQ ID NO 107
<211> LENGTH: 108
<212> TYPE: PRT
<213> ORGANISM: Artificial
<220> FEATURE:
<223> OTHER INFORMATION: Amino Acid Sequence of VL 8E1.5 region

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Gly Leu Ile
        35                  40                  45

Tyr Ser Ala Ser His Arg Tyr Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 108
<211> LENGTH: 112
<212> TYPE: PRT
<213> ORGANISM: Artificial
<220> FEATURE:
<223> OTHER INFORMATION: Amino Acid Sequence of VH 8E1.6 region

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Val Trp Val Arg Gln Ala Pro Gly Lys Gly Leu Glu Trp Val
```

```
                    35                  40                  45
Ala Ser Ile Ser Ser Gly Ser Ser Asn Ile Tyr Tyr Ala Asp Thr Val
 50                  55                  60

Lys Gly Arg Phe Thr Ile Ser Arg Asp Asp Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Pro Tyr Trp Gly Gln Gly Thr Leu Val Thr Val Ser Ser
            100                 105                 110

<210> SEQ ID NO 109
<211> LENGTH: 108
<212> TYPE: PRT
<213> ORGANISM: Artificial
<220> FEATURE:
<223> OTHER INFORMATION: Amino Acid Sequence of VL 8E1.6 region

<400> SEQUENCE: 109

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Val Gly Thr Asn
                 20                  25                  30

Val Ala Trp Tyr Gln Gln Lys Pro Gly Lys Ala Pro Lys Gly Leu Ile
             35                  40                  45

Tyr Ser Ala Ser His Arg Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Arg
            100                 105

<210> SEQ ID NO 110
<211> LENGTH: 19
<212> TYPE: PRT
<213> ORGANISM: Artificial
<220> FEATURE:
<223> OTHER INFORMATION: Heavy Chain Signal Sequence (Human)

<400> SEQUENCE: 110

Met Glu Phe Gly Leu Ser Trp Leu Phe Leu Val Ala Ile Leu Lys Gly
  1               5                  10                  15

Val Gln Cys

<210> SEQ ID NO 111
<211> LENGTH: 22
<212> TYPE: PRT
<213> ORGANISM: Artificial
<220> FEATURE:
<223> OTHER INFORMATION: Light Chain Signal Sequence (Human)

<400> SEQUENCE: 111

Met Asp Met Arg Val Pro Ala Gln Leu Leu Gly Leu Leu Leu Leu Trp
  1               5                  10                  15

Phe Pro Gly Ser Arg Cys
                 20
```

IL-12/P40 BINDING PROTEINS

CROSS-REFERENCE TO RELATED APPLICATION

This application is a division of U.S. Ser. No. 11/478,096 filed Jun. 29, 2006, (now U.S. Pat. No. 7,700,739), which claims priority to U.S. provisional application No. 60/695,679 filed Jun. 30, 2005.

This application is related to U.S. application Ser. No. 09/534,717 filed on Mar. 24, 2000 (issued as U.S. Pat. No. 6,914,128) entitled "Human antibodies that bind human IL-12 and methods for producing." The entire contents of this patent application, and patents issued therefrom, are hereby incorporated herein by reference.

REFERENCE TO JOINT RESEARCH AGREEMENT

Contents of this application are under a joint research agreement entered into by and between Protein Design Labs, Inc. and Abbott Laboratories on Dec. 14, 2005, and directed to recombinantly engineered antibodies.

FIELD OF THE INVENTION

The present invention relates to IL-12p40 binding proteins, and specifically to their uses in the prevention and/or treatment of acute and chronic inflammatory diseases.

BACKGROUND OF THE INVENTION

Human interleukin-12 (IL-12) is a cytokine with a unique structure and pleiotropic effects (Kobayashi, et al. (1989) *J Exp Med* 170:827-845; Seder, et al. (1993) *Proc. Natl. Acad. Sci. USA* 90:10188-10192, Ling, et al. (1995) *J. Immunol.* 154:116-127; Podlaski, et al. (1992) *Arch. Biochem. Biophys.* 294:230-237). IL-12 plays a critical role in the pathology associated with several diseases involving immune and inflammatory responses. A review of IL-12, its biological activities, and its role in disease can be found in Trinchieri, G. (2003) *Nat. Rev. Immun.* 3:133-146. Structurally, IL-12 is a heterodimeric protein (referred to as the "p70 protein") comprising a 35 kDa subunit (p35) and a 40 kDa subunit (p40) which are linked together by a disulfide bridge. The heterodimeric protein is produced primarily by antigen-presenting cells such as monocytes, macrophages and dendritic cells. These cell types also secrete an excess of the p40 subunit relative to p70 subunit. The p40 and p35 subunits are genetically unrelated and neither has been reported to possess biological activity, although the p40 homodimer may function as an IL-12 antagonist.

Functionally, IL-12 plays a central role in regulating the balance between antigen-specific T helper type 1 (Th1) and type 2 (Th2) lymphocytes. The Th1 and Th2 cells govern the initiation and progression of autoimmune disorders, and IL-12 is critical in the regulation of Th1-lymphocyte differentiation and maturation. Cytokines released by the Th1 cells are inflammatory and include interferon gamma (IFN-γ), IL-2, and lymphotoxin (LT). Th2 cells secrete IL-4, IL-5, IL-6, IL-10 and IL-13 to facilitate humoral immunity, allergic reactions, and immunosuppression. Consistent with the preponderance of Th1 responses in autoimmune diseases and the proinflammatory activities of IFN-γ, IL-12 may play a major role in the pathology associated with many autoimmune and inflammatory diseases such as rheumatoid arthritis (RA), multiple sclerosis (MS), psoriasis (PS) and Crohn's disease (CD).

Human patients with MS have demonstrated an increase in IL-12 expression as documented by p40 mRNA levels in acute MS plaques (Windhagen et al., (1995) *J Exp. Med.* 182:1985-1996). In addition, ex vivo stimulation of antigen-presenting cells with CD40L expressing T cells from MS patients resulted in increased IL-12 production compared with control T cells, consistent with the observation that CD40/CD40L interactions are potent inducers of IL-12. Elevated levels of IL-12 p70 have been detected in the synovia of RA patients compared with healthy controls (Morita et al. (1998) *Arth. and Rheumat.* 41:306-314). Cytokine messenger ribonucleic acid (mRNA) expression profile in the RA synovia identified predominantly Th1 cytokines (Bucht et al. (1996) *Clin. Exp. Immunol.* 103:347-367). IL-12 also appears to play a critical role in the pathology associated with Crohn's disease. Increased expression of INF-γ and IL-12 has been observed in the intestinal mucosa of patients with this disease (Fais et al. (1994) *J. Interferon Res.* 14:235-238; Parronchi et al. (1997) *Am. J. Path.* 150:823-832; Monteleone et al. (1997) *Gastroent.* 112:1169-1178, and Berrebi et al. (1998) *Am. J. Path.* 152:667-672). The cytokine secretion profile of T cells from the lamina propria of CD patients is characteristic of a predominantly Th1 response, including greatly elevated IFN-γ levels (Fuss, et al. (1996) J Immunol 157:1261-1270). Moreover, colon tissue sections from CD patients show an abundance of IL-12 expressing macrophages and IFN-γ expressing T cells (Parronchi et al (1997) *Am. J. Path.* 150: 823-832).

IL-23 is also a heterodimeric cytokine and belongs to a family of five such heterodimeric cytokines including IL-12 and IL-27 (Trinchieri et al., (2003) *Immunity* 19:641-644). IL-23 shares the identical p40 subunit as IL-12, but it is associated with a p19 subunit via a disulphide-linkage. The p19 subunit is structurally related to IL-6, granulocyte-colony stimulating factor (G-CSF), and the p35 subunit of IL-12. IL-23 is produced by similar cell types as IL-12, and its receptor is expressed on T cells, NK cells, and phagocytic and dendritic hematopoietic cells. IL-23 mediates signaling by binding to a heterodimeric receptor, comprised of IL-23R and IL-12beta1. The IL-12beta1 subunit is shared by the IL-12 receptor, which is composed of IL-12beta1 and IL-12beta2. IL-23 does share overlapping functions with IL-12 (by inducing IFN-γ production, Th1 cell differentiation and activating the antigen-presenting functions of dendritic cells) however it selectively induces proliferation of memory T cells (Oppmann et al. (2000) *Immunity* 13:715-725, Parham, et al. (2002) *J. Immunol.* 168:5699-5708).

The role of IL-23 in autoimmune inflammation has been dissected in part through studies with p19 knockout mice (Murphy et al., *J. Exp. Med.* 198:1951-1957; Cua et al. (2003) *Nature* 421:744-748). Studies have demonstrated that IL-23 modulates immune response to infection (see, e.g., Pirhonen, et al. (2002) *J. Immunol.* 169:5673-5678; Broberg, et al. (2002) *J. Interferon Cytokine Res.* 22:641-651; Elkins, et al. (2002) *Infection Immunity* 70:1936-1948; Cooper, et al. (2002) *J. Immunol.* 168:1322-1327). IL-23 is thought to play a role in immune-mediated inflammatory diseases (Langrish et. al. (2004) *Immunological Reviews* 202: 96-105).

Due to the role of human IL-12 in a variety of human disorders, therapeutic strategies have been designed to inhibit or counteract IL-12 activity. In particular, antibodies that bind to, and neutralize, IL-12 have been sought as a means to inhibit IL-12 activity. Some of the earliest antibodies were murine monoclonal antibodies (mAbs), secreted by hybridomas prepared from lymphocytes of mice immunized with IL-12 (see e.g., Strober et al., PCT Publication No. WO 97/15327; Gately et al., WO 99/37682 A2; Neurath et al., *J Exp. Med* 182:1281-1290 (1995); Duchmann et al., *J Immunol.* 26:934-938 (1996)). These murine IL-12 antibodies are limited for their use in vivo due to problems associated with administration of mouse antibodies to humans, such as short serum half life, an inability to trigger certain human effector functions and elicitation of an unwanted immune response against the mouse antibody in a human (the "human anti-mouse antibody" (HAMA) reaction).

One approach to overcome the problem problems associated with use of fully murine antibodies in humans is to generate fully human antibodies such as those disclosed in Salfeld et al., PCT publication No. WO 00/56772 A1. Other approaches to overcome the problems associated with use of fully murine antibodies in humans have involved genetically engineering the antibodies to be more "human-like." For example, chimeric antibodies, in which the variable regions of the antibody chains are murine-derived and the constant regions of the antibody chains are human-derived, have been prepared (Junghans, et al. (1990) *Cancer Res.* 50:1495-1502; Brown et al. (1991) *Proc. Natl. Acad. Sci. USA* 88:2663-2667; Kettleborough et al. (1991) *Prot. Engineer.* 4:773-783). Such chimeric antibodies to IL-12 are also disclosed in Peritt et al. PCT publication No. WO 2002/097048 A2. However, because these chimeric antibodies still retain murine variable chain sequences, they still may elicit an unwanted immune reaction, the human anti-chimeric antibody (HACA) reaction especially when administered for prolonged periods.

There is a need in the art for improved antibodies capable of binding the p40 subunit of IL-12 (IL-12p40). Preferably the antibodies bind IL-12 and/or IL-23. Preferably the antibodies are capable of neutralizing IL-12 and/or IL-23. The present invention provides a novel family of binding proteins, CDR grafted antibodies, humanized antibodies, and fragments thereof, capable binding IL-12p40, binding with high affinity, and binding and neutralizing IL-12 and/or IL-23.

SUMMARY OF THE INVENTION

This invention pertains to IL-12p40 binding proteins, particularly antibodies capable of binding the p40 subunit of human IL-12 and the p40 subunit of human IL-23. Further, the invention provides methods of making and using IL-12p40 binding proteins.

One aspect of this invention pertains to a binding protein comprising an antigen binding domain capable of binding a p40 subunit of IL-12. In one embodiment the antigen binding domain comprises at least one CDR comprising an amino acid sequence selected from the group consisting of:

CDR-H1. $X_1$-$X_2$-$X_3$-$X_4$-$X_5$-$X_6$-$X_7$ (SEQ ID NO: 55), wherein;
  $X_1$ is D, K, T, or S;
  $X_2$ is Y, S, or T;
  $X_3$ is Y, V, G, W, S, or F;
  $X_4$ is I, or M;
  $X_5$ is H, G, E, or V;
  $X_6$ is V, or is not present; and
  $X_7$ is S, or is not present;
CDR-H2. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ $X_{18}$-$X_{19}$-$X_{20}$ (SEQ ID NO: 56), wherein;
  $X_1$ is H, D, G, W, S, Y or R;
  $X_2$ is I, or F;
  $X_3$ is Y, W, L, S, N, D or G;
  $X_4$ is W, P, H, T, or S;
  $X_5$ is D, G, E, A, or I;
  $X_6$ is D, G, S, T, or N;
  $X_7$ is D, G, S, or P;
  $X_8$ is K, N, S, E, T, or H;
  $X_9$ is Y, T, P, I, or N;
  $X_{10}$ is Y, N, T, H, K, S, or G;
  $X_{11}$ is N, or Y;
  $X_{12}$ is P, N, A, D, or S;
  $X_{13}$ is S, E, D, or P;
  $X_{14}$ is L, K, D, T, or Y;
  $X_{15}$ is K, F, V, M, R, or A;
  $X_{16}$ is S, K, Q, P, or is not present;
  $X_{17}$ is D, G, R, or is not present;
  $X_{18}$ is F, or is not present;
  $X_{19}$ is Q, or is not present; and
  $X_{20}$ is D, or is not present;
CDR-H3. $X_1$-$X_2$-$X_3$-$X_4$-$X_5$-$X_6$-$X_7$-$X_8$-$X_9$-$X_{10}$-$X_{11}$-$X_{12}$-$X_{13}$ (SEQ ID NO: 57), wherein;
  $X_1$ is R, N, or W;
  $X_2$ is G, T, R, P, or H;
  $X_3$ is I, R, F, Y, or Q;
  $X_4$ is R, V, Y, F, or A;
  $X_5$ is S, N, G, A, or R;
  $X_6$ is A, Y, L, F, or M;
  $X_7$ is M, A, D, L, or F;
  $X_8$ is D, M, Y, or W;
  $X_9$ is Y, D, or N;
  $X_{10}$ is Y, A, or is not present;
  $X_{11}$ is M, or is not present;
  $X_{12}$ is D, or is not present; and
  $X_{13}$ is Y, or is not present;
CDR-L1. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO: 58), wherein;
  $X_1$ is K, or R;
  $X_2$ is A;
  $X_3$ is S;
  $X_4$ is Q, or E;
  $X_5$ is S, or N;
  $X_6$ is V, or I;
  $X_7$ is S, G, or D;
  $X_8$ is N, T, or K;
  $X_9$ is D, N, or Y;
  $X_{10}$ is V, G, or L;
  $X_{11}$ is A, I, or H;
  $X_{12}$ is S, or is not present;
  $X_{13}$ is F, or is not present;
  $X_{14}$ is M, or is not present; and
  $X_{15}$ is N, or is not present;
CDR-L2. $X_1$-$X_2$-$X_3$-$X_4$-$X_5$-$X_6$-$X_7$-$X_8$ (SEQ ID NO: 59), wherein;
  $X_1$ is Y, or S;
  $X_2$ is A, or T;
  $X_3$ is S, or A;
  $X_4$ is N, H, S, or Q;
  $X_5$ is R, N, or S;
  $X_6$ is Y, Q, or I;
  $X_7$ is T, S, or G; and
  $X_8$ is S, or is not present; and
CDR-L3. $X_1$-$X_2$-$X_3$-$X_4$-$X_5$-$X_6$-$X_7$-$X_8$-$X_9$ (SEQ ID NO: 60), wherein;
  $X_1$ is Q;
  $X_2$ is Q;
  $X_3$ is D, Y, or S;
  $X_4$ is Y, N, K, or I;
  $X_5$ is N, T, S, or E;
  $X_6$ is S, Y, V, or W;
  $X_7$ is P;

$X_8$ is W, F, Y, L, or P; and $X_9$ is T, or S.

Preferably, the antigen binding domain comprises at least one CDR comprising an amino acid sequence selected from the group consisting of residues 31-37 of SEQ ID NO.:35; residues 52-67 of SEQ ID NO.:35; residues 100-108 of SEQ ID NO.:35; residues 24-34 of SEQ ID NO.:36; residues 50-56 of SEQ ID NO.:36; residues 89-97 of SEQ ID NO.:36; residues 31-37 of SEQ ID NO.:37; residues 52-67 of SEQ ID NO.:37; residues. 100-109 of SEQ ID NO.:37; residues 24-34 of SEQ ID NO.:38; residues 50-56 of SEQ ID NO.:38; residues 89-97 of SEQ ID NO.:38; residues 31-35 of SEQ ID NO.:39; residues 50-66 of SEQ ID NO.:39; residues 99-106 of SEQ ID NO.:39; residues 24-34 of SEQ ID NO.:40; residues 50-56 of SEQ ID NO.:40; residues 89-97 of SEQ ID NO.:40; residues 31-35 of SEQ ID NO.:41; residues 50-66 of SEQ ID NO.:41; residues 99-106 of SEQ ID NO.:41; residues 24-34 of SEQ ID NO.:42; residues 50-56 of SEQ ID NO.:42; residues 89-97 of SEQ ID NO.:42; residues 31-35 of SEQ ID NO.:43; residues 50-66 of SEQ ID NO.:43; residues 99-106 of SEQ ID NO.:43; residues 24-34 of SEQ ID NO.:44; residues 50-56 of SEQ ID NO.:44; residues 89-97 of SEQ ID NO.:44; residues 31-35 of SEQ ID NO.:45; residues 50-66 of SEQ ID NO.:45; residues 99-101 of SEQ ID NO.:45; residues 24-34 of SEQ ID NO.:46; residues 50-56 of SEQ ID NO.:46; residues 89-97 of SEQ ID NO.:46; residues 31-35 of SEQ ID NO.:47; residues 50-66 of SEQ ID NO.:47; residues 99-106 of SEQ ID NO.:47; residues 24-34 of SEQ ID NO.:48; residues 50-56 of SEQ ID NO.:48; residues 89-97 of SEQ ID NO.:48; residues 31-35 of SEQ ID NO.:49; residues 50-66 of SEQ ID NO.:49; residues 99-111 of SEQ ID NO.:49; residues 24-38 of SEQ ID NO.:50; residues 53-60 of SEQ ID NO.:50; residues 93-101 of SEQ ID NO.:50; residues 31-37 of SEQ ID NO.:51; residues 52-67 of SEQ ID NO.:51; residues 100-109 of SEQ ID NO.:51; residues 24-34 of SEQ ID NO.:52; residues 50-56 of SEQ ID NO.:52; residues 89-97 of SEQ ID NO.:52; residues 31-35 of SEQ ID NO.:53; residues 47-66 of SEQ ID NO.:53; residues 99-107 of SEQ ID NO.:53; residues 24-34 of SEQ ID NO.:54; residues 50-56 of SEQ ID NO.:54; and residues 89-97 of SEQ ID NO.:54. In a preferred embodiment, the binding protein comprises at least 3 CDRs selected from the group consisting of the sequences disclosed above. More preferably the 3 CDRs selected are from sets of variable domain CDRs selected from the group consisting of:

| VH 1D4 CDR Set | |
|---|---|
| VH 1D4 CDR-H1 | Residues 31-37 of SEQ ID NO.: 35 |
| VH 1D4 CDR-H2 | Residues 52-67 of SEQ ID NO.: 35 |
| VH 1D4 CDR-H3 | Residues 100-108 of SEQ ID NO.: 35 |
| VL 1D4 CDR Set | |
| VL 1D4 CDR-L1 | Residues 24-34 of SEQ ID NO.: 36 |
| VL 1D4 CDR-L2 | Residues 50-56 of SEQ ID NO.: 36 |
| VL 1D4 CDR-L3 | Residues 89-97 of SEQ ID NO.: 36 |
| VH 1A6 CDR Set | |
| VH 1A6 CDR-H1 | Residues 31-37 of SEQ ID NO.: 37 |
| VH 1A6 CDR-H2 | Residues 52-67 of SEQ ID NO.: 37 |
| VH 1A6 CDR-H3 | Residues 100-109 of SEQ ID NO.: 37 |
| VL 1A6 CDR Set | |
| VL 1A6 CDR-L1 | Residues 24-34 of SEQ ID NO.: 38 |
| VL 1A6 CDR-L2 | Residues 50-56 of SEQ ID NO.: 38 |
| VL 1A6 CDR-L3 | Residues 89-97 of SEQ ID NO.: 38 |
| VH 1D8 CDR Set | |
| VH 1D8 CDR-H1 | Residues 31-35 of SEQ ID NO.: 39 |
| VH 1D8 CDR-H2 | Residues 50-66 of SEQ ID NO.: 39 |
| VH 1D8 CDR-H3 | Residues 99-106 of SEQ ID NO.: 39 |
| VL 1D8 CDR Set | |
| VL 1D8 CDR-L1 | Residues 24-34 of SEQ ID NO.: 40 |
| VL 1D8 CDR-L2 | Residues 50-56 of SEQ ID NO.: 40 |
| VL 1D8 CDR-L3 | Residues 89-97 of SEQ ID NO.: 40 |
| VH 3G7 CDR Set | |
| VH 3G7 CDR-H1 | Residues 31-35 of SEQ ID NO.: 41 |
| VH 3G7 CDR-H2 | Residues 50-66 of SEQ ID NO.: 41 |
| VH 3G7 CDR-H3 | Residues 99-106 of SEQ ID NO.: 41 |
| VL 3G7 CDR Set | |
| VL 3G7 CDR-L1 | Residues 24-34 of SEQ ID NO.: 42 |
| VL 3G7 CDR-L2 | Residues 50-56 of SEQ ID NO.: 42 |
| VL 3G7 CDR-L3 | Residues 89-97 of SEQ ID NO.: 42 |
| VH 5E8 CDR Set | |
| VH 5E8 CDR-H1 | Residues 31-35 of SEQ ID NO.: 43 |
| VH 5E8 CDR-H2 | Residues 50-66 of SEQ ID NO.: 43 |
| VH 5E8 CDR-H3 | Residues 99-106 of SEQ ID NO.: 43 |
| VL 5E8 CDR Set | |
| VL 5E8 CDR-L1 | Residues 24-34 of SEQ ID NO.: 44 |
| VL 5E8 CDR-L2 | Residues 50-56 of SEQ ID NO.: 44 |
| VL 5E8 CDR-L3 | Residues 89-97 of SEQ ID NO.: 44 |
| VH 8E1 CDR Set | |
| VH 8E1 CDR-H1 | Residues 31-35 of SEQ ID NO.: 45 |
| VH 8E1 CDR-H2 | Residues 50-66 of SEQ ID NO.: 45 |
| VH 8E1 CDR-H3 | Residues 99-101 of SEQ ID NO.: 45 |
| VL 8E1 CDR Set | |
| VL 8E1 CDR-L1 | Residues 24-34 of SEQ ID NO.: 46 |
| VL 8E1 CDR-L2 | Residues 50-56 of SEQ ID NO.: 46 |
| VL 8E1 CDR-L3 | Residues 89-97 of SEQ ID NO.: 46 |
| VH 1H6 CDR Set | |
| VH 1H6 CDR-H1 | Residues 31-35 of SEQ ID NO.: 47 |
| VH 1H6 CDR-H2 | Residues 50-66 of SEQ ID NO.: 47 |
| VH 1H6 CDR-H3 | Residues 99-106 of SEQ ID NO.: 47 |
| VL 1H6 CDR Set | |
| VL 1H6 CDR-L1 | Residues 24-34 of SEQ ID NO.: 48 |
| VL 1H6 CDR-L2 | Residues 50-56 of SEQ ID NO.: 48 |
| VL 1H6 CDR-L3 | Residues 89-97 of SEQ ID NO.: 48 |
| VH 3A11 CDR Set | |
| VH 3A11 CDR-H1 | Residues 31-35 of SEQ ID NO.: 49 |
| VH 3A11 CDR-H2 | Residues 50-66 of SEQ ID NO.: 49 |
| VH 3A11 CDR-H3 | Residues 99-111 of SEQ ID NO.: 49 |
| VL 3A11 CDR Set | |
| VL 3A11 CDR-L1 | Residues 24-38 of SEQ ID NO.: 50 |
| VL 3A11 CDR-L2 | Residues 54-60 of SEQ ID NO.: 50 |
| VL 3A11 CDR-L3 | Residues 93-101 of SEQ ID NO.: 50 |
| VH 4B4 CDR Set | |
| VH 4B4 CDR-H1 | Residues 31-37 of SEQ ID NO.: 51 |
| VH 4B4 CDR-H2 | Residues 52-67 of SEQ ID NO.: 51 |
| VH 4B4 CDR-H3 | Residues 100-109 of SEQ ID NO.: 51 |
| VL 4B4 CDR Set | |
| VL 4B4 CDR-L1 | Residues 24-34 of SEQ ID NO.: 52 |
| VL 4B4 CDR-L2 | Residues 50-56 of SEQ ID NO.: 52 |
| VL 4B4 CDR-L3 | Residues 89-97 of SEQ ID NO.: 52 |
| VH 7G3 CDR Set | |
| VH 7G3 CDR-H1 | Residues 31-35 of SEQ ID NO.: 53 |
| VH 7G3 CDR-H2 | Residues 50-66 of SEQ ID NO.: 53 |
| VH 7G3 CDR-H3 | Residues 99-107 of SEQ ID NO.: 53 |

| And VL 7G3 CDR Set | |
|---|---|
| VL 7G3 CDR-L1 | Residues 24-34 of SEQ ID NO.: 54 |
| VL 7G3 CDR-L2 | Residues 50-56 of SEQ ID NO.: 54 |
| VL 7G3 CDR-L3 | Residues 89-97 of SEQ ID NO.: 54 |

In one embodiment the binding protein of the invention comprises at least two variable domain CDR sets. More preferably, the two variable domain CDR sets are selected from a group consisting of: VH 1D4 CDR Set & VL 1D4 CDR Set; VH 1A6 CDR Set & VL 1A6 CDR Set; VH 1D8 CDR Set & VL 1D8 CDR Set; VH 3G7 CDR Set & VL 3G7 CDR Set; VH 5E8 CDR Set & VL 5E8 CDR Set; VH 8E1 CDR Set & VL 8E1 CDR Set; VH 1H6 CDR Set & VL 1H6 CDR Set; VH 3A11 CDR Set & VL 3A11 CDR Set; VH 4B4 CDR Set & VL 4B4 CDR Set; and VH 7G3 CDR Set & VL 7G3 CDR Set.

In another embodiment the binding protein disclosed above further comprises a human acceptor framework. Preferably the human acceptor framework comprises a amino acid sequence selected from the group consisting of SEQ ID NO.:6; SEQ ID NO.:7; SEQ ID NO.:8; SEQ ID NO.:9; SEQ ID NO.:10; SEQ ID NO.:11; SEQ ID NO.:12; SEQ ID NO.:13; SEQ ID NO.:14; SEQ ID NO.:15; SEQ ID NO.:16; SEQ ID NO.:17; SEQ ID NO.:18; SEQ ID NO.:19; SEQ ID NO.:20; SEQ ID NO.:21; SEQ ID NO.:22; SEQ ID NO.:23; SEQ ID NO.:24; SEQ ID NO.:25; SEQ ID NO.:26; SEQ ID NO.:27; SEQ ID NO.:28; SEQ ID NO.:29; SEQ ID NO.:30; SEQ ID NO.:31; SEQ ID NO.:32; SEQ ID NO.:33; SEQ ID NO.:34, SEQ ID NO.:92, SEQ ID NO.:93, SEQ ID NO.:94, SEQ ID NO.:95, SEQ ID NO.:96, AND SEQ ID NO.:97.

In a preferred embodiment the binding protein is a CDR grafted antibody or antigen binding portion thereof capable of binding the p40 subunit of IL-12 or IL-23. Preferably the CDR grafted antibody or antigen binding portion thereof comprise one or more CDRs disclosed above. More preferably the CDR grafted antibody or antigen binding portion thereof comprises at least one variable domain having an amino acid sequence selected from the group consisting of SEQ ID NO.:61; SEQ ID NO.:62; SEQ ID NO.:63; SEQ ID NO.:64; SEQ ID NO.:65; SEQ ID NO.:66; SEQ ID NO.:67; SEQ ID NO.:68; SEQ ID NO.:69; SEQ ID NO.:70; SEQ ID NO.:71; SEQ ID NO.:72; SEQ ID NO.:73; SEQ ID NO.:74; SEQ ID NO.:75; SEQ ID NO.:76; SEQ ID NO.:77; and SEQ ID NO.:78. Most preferably the CDR grafted antibody or antigen binding portion thereof comprises two variable domains selected from the group disclosed above. Preferably the CDR grafted antibody or antigen binding portion thereof comprises a human acceptor framework. More preferably the human acceptor framework is any one of the human acceptor frameworks disclosed above.

In a preferred embodiment the binding protein is a humanized antibody or antigen binding portion thereof capable of binding the p40 subunit of IL-12 or IL-23. Preferably the humanized antibody or antigen binding portion thereof comprise one or more CDRs disclosed above incorporated into a human antibody variable domain of a human acceptor framework. Preferably the human antibody variable domain is a consensus human variable domain. More preferably the human acceptor framework comprises at least one Framework Region amino acid substitution at a key residue, wherein the key residue is selected from the group consisting of a residue adjacent to a CDR; a glycosylation site residue; a rare residue; a residue capable of interacting with a p40 subunit of human IL-12; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. Preferably the key residue is selected from the group consisting of 3H, 5H, 10H, 11H, 12H, 13H, 15H, 16H, 18H, 19H, 23H, 24H, 25H, 30H, 41H, 44H, 46H, 49H, 66H, 68H, 71H, 73H, 74H, 75H, 76H, 77H, 78H, 79H, 81H, 82H, 82AH, 82BH, 82CH, 83H, 84H, 85H, 86H, 87H, 89H, 93H, 98H, 108H, 109H, 1L, 2L, 3L, 7L, 8L, 9L, 10L, 11L, 12L, 13L, 15L, 17L, 19L, 20L, 21L, 22L, 36L, 41L, 42L, 43L, 45L, 46L, 58L, 60L, 62L, 63L, 67L, 70L, 73L, 74L, 77L, 78L, 79L, 80L, 83L, 85L, 87L, 104L, and 106L. Preferably the human acceptor framework human acceptor framework comprises at least one Framework Region amino acid substitution, wherein the amino acid sequence of the framework is at least 65% identical to the sequence of said human acceptor framework and comprises at least 70 amino acid residues identical to said human acceptor framework.

In a preferred embodiment the binding protein is a humanized antibody or antigen binding portion thereof capable of binding the p40 subunit of IL-12 or IL-23. Preferably the humanized antibody, or antigen binding portion, thereof comprises one or more CDRs disclosed above. More preferably the humanized antibody, or antigen binding portion, thereof comprises three or more CDRs disclosed above. Most preferably the humanized antibody, or antigen binding portion, thereof comprises six CDRs disclosed above.

In another embodiment of the claimed invention, the humanized antibody or antigen binding portion thereof comprises at least one variable domain having an amino acid sequence selected from the group consisting of SEQ ID NO.: 79, SEQ ID NO.:80, SEQ ID NO.:81, SEQ ID NO.:82, SEQ ID NO.:83, SEQ ID NO.:84, SEQ ID NO.:85, SEQ ID NO.: 86, SEQ ID NO.:87, SEQ ID NO.:88, SEQ ID NO.:89, SEQ ID NO.:90, SEQ ID NO.:91, SEQ ID NO.:98, SEQ ID NO.: 99, SEQ ID NO.:100, SEQ ID NO.:101, SEQ ID NO.:102, AND SEQ ID NO.:103, SEQ ID NO.:104, SEQ ID NO.:105, SEQ ID NO.:106, SEQ ID NO.:107, SEQ ID NO.:108, and SEQ ID NO.:109. More preferably the humanized antibody or antigen binding portion thereof comprises two variable domains selected from the group disclosed above. Most preferably humanized antibody, or antigen binding portion thereof comprises two variable domains, wherein said two variable domains have amino acid sequences selected from the group consisting of SEQ ID NO.:67 & SEQ ID NO.:79, SEQ ID NO.:80 & SEQ ID NO.:81, SEQ ID NO.:82 & SEQ ID NO.:83, SEQ ID NO.:84 & SEQ ID NO.:85, SEQ ID NO.:86 & SEQ ID NO.:87, SEQ ID NO.:88 & SEQ ID NO.:89, SEQ ID NO.:90 & SEQ ID NO.:91, SEQ ID NO.:98 & SEQ ID NO.:99, SEQ ID NO.:100 & SEQ ID NO.:101, SEQ ID NO.:102 & SEQ ID NO.:103, SEQ ID NO.:104 & SEQ ID NO.:105, SEQ ID NO.:106 & SEQ ID NO.:107, and SEQ ID NO.:108 & SEQ ID NO.:109.

In a preferred embodiment the binding protein disclosed above comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. More preferably, the binding protein comprises SEQ ID NO.:2; SEQ ID NO.:3; SEQ ID NO.:4; and SEQ ID NO.:5.

The binding protein of the invention is capable of binding a target selected from the group consisting of IL-12 and IL-23. Preferably the binding protein is capable of modulating a biological function of a target selected from the group consisting of IL-12 and IL-23. More preferably the binding protein is capable of neutralizing a target selected from the group consisting of IL-12 and IL-23.

In one embodiment, the binding protein of the invention has an on rate constant (Kon) to IL-12 or IL-23 of at least about $10^2 M^{-1}s^{-1}$; at least about $10^3 M^{-1}s^{-1}$; at least about $10^4 M^{-1}s^{-1}$; at least about $10^5 M^{-1}s^{-1}$; or at least about $10^6 M^{-1}s^{-1}$, as measured by surface plasmon resonance. Preferably, the binding protein of the invention has an on rate constant (Kon) to IL-12 or IL-23 between $10^2 M^{-1}s^{-1}$ to $10^3 M^{-1}s^{-1}$; between $10^3 M^{-1}s^{-1}$ to $10^4 M^{-1}s^{-1}$; between $10^4 M^{-1}s^{-1}$ to $10^5 M^{-1}s^{-1}$; or between $10^5 M^{-1}s^{-1}$ to $10^6 M^{-1}s^{-1}$, as measured by surface plasmon resonance.

In another embodiment, the binding protein of the invention has an off rate constant (Koff) to IL-12 or IL-23 of at most about $10^{-3}s^{-1}$; at most about $10^{-4}s^{-1}$; at most about $10^{-5}s^{-1}$; or at most about $10^{-6}s^{-1}$, as measured by surface plasmon resonance. Preferably, the binding protein of the invention has an off rate constant (Koff) to IL-12 or IL-23 of $10^{-3}s^{-1}$ to $10^{-4}s^{-1}$; of $10^{-4}s^{-1}$ to $10^{-5}s^{-1}$; or of $10^{-5}s^{-1}$ to $10^{-6}s^{-1}$, as measured by surface plasmon resonance.

In another embodiment, the binding protein of the invention has a dissociation constant ($K_D$) to IL-12 or IL-23 of at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$M. Preferably, the binding protein of the invention has a dissociation constant ($K_D$) to IL-12 or IL-23 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ to M $10^{-13}$M. One embodiment of the invention provides an antibody construct comprising any one of the binding proteins disclosed above and a linker polypeptide or an immunoglobulin. In a preferred embodiment the antibody construct is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody. In a preferred embodiment the antibody construct comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. More preferably, the antibody construct comprises SEQ ID NO.:2; SEQ ID NO.:3; SEQ ID NO.:4; and SEQ ID NO.:5. In another embodiment the invention provides an antibody conjugate comprising an the antibody construct disclosed above and an agent an agent selected from the group consisting of; an immunoadhesion molecule, an imaging agent, a therapeutic agent, and a cytotoxic agent. In a preferred embodiment the imaging agent selected from the group consisting of a radiolabel, an enzyme, a fluorescent label, a luminescent label, a bioluminescent label, a magnetic label, and biotin. More preferably the imaging agent is a radiolabel selected from the group consisting of: $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In a preferred embodiment the therapeutic or cytotoxic agent is selected from the group consisting of an anti-metabolite, an alkylating agent, an antibiotic, a growth factor, a cytokine, an anti-angiogenic agent, an anti-mitotic agent, an anthracycline, toxin, and an apoptotic agent.

In another embodiment the antibody construct is glycosylated. Preferably the glycosylation is a human glycosylation pattern.

In another embodiment binding protein, antibody construct or antibody conjugate disclosed above exists as a crystal. Preferably the crystal is a carrier-free pharmaceutical controlled release crystal. In a preferred embodiment the crystallized binding protein, crystallized antibody construct or crystallized antibody conjugate has a greater half life in vivo than its soluble counterpart. In another preferred embodiment the crystallized binding protein, crystallized antibody construct or crystallized antibody conjugate retains biological activity after crystallization.

One aspect of the invention pertains to an isolated nucleic acid encoding any one of the binding protein, antibody construct or antibody conjugate disclosed above. A further embodiment provides a vector comprising the isolated nucleic acid disclosed above wherein said vector is selected from the group consisting of pcDNA; pTT (Durocher et al., *Nucleic Acids Research* 2002, Vol 30, No. 2); pTT3 (pTT with additional multiple cloning site; pEFBOS (Mizushima, S, and Nagata, S., (1990) *Nucleic Acids Research* Vol 18, No. 17, p. 5322); pBV; pJV; and pBJ.

In another aspect a host cell is transformed with the vector disclosed above. Preferably the host cell is a prokaryotic cell. More preferably the host cell is *E. Coli*. In a related embodiment the host cell is an eukaryotic cell. Preferably the eukaryotic cell is selected from the group consisting of protist cell, animal cell, plant cell and fungal cell. More preferably the host cell is a mammalian cell including, but not limited to, CHO and COS; or a fungal cell such as *Saccharomyces cerevisiae*; or an insect cell such as Sf9.

Another aspect of the invention provides a method of producing a binding protein that binds the p40 subunit of IL-12, comprising culturing any one of the host cells disclosed above in a culture medium under conditions sufficient to produce a binding protein that binds the p40 subunit of IL-12. Another embodiment provides a binding protein produced according to the method disclosed above.

One embodiment provides a composition for the release of a binding protein wherein the composition comprises a formulation which in turn comprises a crystallized binding protein, crystallized antibody construct or crystallized antibody conjugate as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, antibody construct or antibody conjugate as disclosed above and a pharmaceutically acceptable carrier. In a further embodiment the pharmaceutical composition comprises at least one additional therapeutic agent for treating a disorder in which IL-12 and/or IL-23 activity is detrimental. Preferably the additional agent is selected from the group consisting of: Therapeutic agent, imaging agent, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for inhibiting human IL-12 and/or human IL-23 activity comprising contacting human IL-12 and/or human IL-23 with a binding protein disclosed above such that human IL-12 and/or human IL-23 activity is inhibited. In a related aspect the invention provides a method for inhibiting human IL-12 and/or human IL-23 activity in a human subject suffering from a disorder in which IL-12 and/or IL-23 activity is detrimental, comprising administering to the human subject a binding protein disclosed above such that human IL-12 and/or human IL-23 activity in the human subject is inhibited and treatment is achieved. Preferably the disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, *chlamydia, yersinia* and *salmonella* associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoproteinemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic arteriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant Lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkins lymphoma, occlusion of the abdominal aorta and its branches, occlusive arterial disorders, OKT3® therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemaphagocytic syndrome, Wernicke-Korsakoff syndrome, Wilson's disease, xenograft rejection of any organ or tissue.

In another aspect the invention provides a method of treating a patient suffering from a disorder in which human IL-12 and/or human IL-23 is detrimental comprising the step of administering any one of the binding proteins disclosed above before, concurrent, or after the administration of a second agent, as discussed above. In a preferred embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFαconverting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, antiinflammatory cytokines, IL-4, IL-10, IL-11, IL-13 and TGFβ.

In a preferred embodiment the pharmaceutical compositions disclosed above are administered to the subject by at least one mode selected from parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one IL-12 anti-idiotype antibody to at least one IL-12 binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

DETAILED DESCRIPTION OF THE INVENTION

This invention pertains to IL-12p40 binding proteins, particularly anti-IL-12p40 antibodies, or antigen-binding portions thereof, that bind IL-12p40. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human IL-12p40, human IL-12 and human IL-23; to inhibit human IL-12 and/or human IL-23 activity, either in vitro or in vivo; and to regulate gene expression are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "human IL-12" (abbreviated herein as hIL-12, or IL-12), as used herein, includes a human cytokine that is secreted primarily by antigen presenting cells such as monocytes macrophages and dendritic cells. The term includes a heterodimeric protein comprising a 35 kD subunit (p35) and a 40 kD subunit (p40) which are both linked together with a disulfide bridge. The heterodimeric protein is referred to as a "p70 protein". The structure of human IL-12 is described further in, for example, Kobayashi, et al. (1989) *J. Exp Med.* 170:827-845; Seder, et al. (1993) *Proc. Natl. Acad. Sci. USA* 90:10188-10192; Ling, et al. (1995) *J. Immunol.* 154:116-127; Podlaski, et al. (1992) *Arch. Biochem. Biophys.* 294:230-237. The term human IL-12 is intended to include recombinant human IL-12 (rh IL-12), which can be prepared by standard recombinant expression methods.

The term "human IL-23" (abbreviated herein as hIL-23, or IL-23), as used herein, includes a heterodimeric human cytokine belonging to a family of five such heterodimeric cytokines including IL-12 and IL-27 (Trinchieri et al., (2003) Immunity 19:641-644). The term includes a heterodimeric protein comprising a 19 kD subunit (p19) and a 40 kD subunit (p40) which are both linked together with a disulfide bridge. The term human IL-23 is intended to include recombinant human IL-23 (rh IL-23), which can be prepared by standard recombinant expression methods.

The term "IL-12p40", identical to "IL-23p40", and also referred to simply as "p40", as used herein, includes the 40 kD subunit of the human cytokine IL-12 (p40) and the 40 kD subunit of the human cytokine IL-23. Table 1 shows the amino acid sequence of IL-12p40, SEQ ID No. 1, which is known in the art.

TABLE 1

Sequence of p40 subunit of IL-12 and IL-23

| Protein | Sequence Identifier | Sequence<br>123456789012345678901234567890012 |
|---|---|---|
| p40 subunit of IL-12 and IL-23 | SEQ ID NO.: | 1 MCHQQLVISWFSLVFLDLVAIWELKKDVYVVE<br>LDWYPDAPGEMVVLTCDTPEEDGITWTLDQSS<br>EVLGSGKTLTIQVKEFGDAGQYTCHKGGEVLS<br>HSLLLLHKKEDGIWSTDILKDQKEPKNKTFLR<br>CEAKNYSGRFTCWWLTTISTDLTFSVKSSRGS<br>SDPQGVTCGAATLSAERVRGDNKEYEYSVECQ<br>EDSACPAAEESLPIEVMVDAVHKLKYENYTSS<br>FFIRDIIKPDPPKNLQLKPLKNSRQVEVSWEY<br>PDTWSTPHSYFSLTFCVQVQGKSKREKKDRVF<br>TDKTSATVICRKNASISVRAQDRYYSSSWSEW<br>ASVPCS |

"Biological activity" as used herein, refers to all inherent biological properties of the cytokine. Biological properties of IL-12 include but are not limited to binding IL-12 receptor; induction of interferon-gamma (IFN-γ) secretion and regulation of balance between antigen-specific T helper type 1 (Th1) and type 2 (Th2) lymphocytes. Biological properties of IL-23 include but are not limited to binding IL-23 receptor, inducing IFN-γ production, Th1 cell differentiation and activating the antigen-presenting functions of dendritic cells, and selectively inducing proliferation of memory T cells.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., hIL-12). It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., (1994) *Structure* 2:1121-1123). An immunoglobulin constant domain refers to a heavy or light chain constant domain. Human IgG heavy chain and light chain constant domain amino acid sequences are known in the art and represented in Table 2.

TABLE 2

Sequence of human IgG heavy chain constant domain and light chain constant domain

| Protein | Sequence Identifier | Sequence 123456789012345678901234567890012 |
|---|---|---|
| Ig gamma-1 constant region | SEQ ID NO.: 2 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO.: 3 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO.: 4 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | SEQ ID NO.: 5 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may, however, have cross-reactivity to other antigens, such as IL-12 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *Trends Biotechnol.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, *J. Mol. Biol.* 196:901-917 (1987) and Chothia et al., *Nature* 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. (*FASEB J.* 9:133-139 (1995)) and MacCallum (*J Mol Biol* 262(5):732-745 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

HEAVY CHAIN ACCEPTOR SEQUENCES

| SEQ ID No. | Protein region | Sequence 123456789012345678901234567890123456789012 |
|---|---|---|
| 6 | VH2-70/JH6 FR1 | EVTLRESGPALVKPTQTLTLTCTFSGFSLS |
| 7 | VH2-70/JH6 FR2 | WIRQPPGKALEWLA |
| 8 | VH2-70/JH6 FR3 | RLTISKDTSKNQVVLTMTNMDPVDTATYYCAR |
| 9 | VH2-70/JH6 FR4 | WGQGTTVTVSS |
| 10 | VH2-26/JH6 FR1 | EVTLKESGPVLVKPTETLTLTCTVSGFSLS |
| 7 | VH2-26/JH6 FR2 | WTRQPPGKALEWLA |
| 11 | VH2-26/JH6 FR3 | RLTISKDTSKSQVVLTMTNMDPVDTATYYCAR |
| 9 | VH2-26/JH6 FR4 | WGQGTTVTVSS |
| 12 | VH3-72/JH6 FR1 | EVQLVESGGGLVQPGGSLRLSCAASGFTFS |
| 13 | VH3-72/JH6 FR2 | WVRQAPGKGLEWVG |
| 14 | VH3-72/JH6 FR3 | RFTISRDDSKNSLYLQMNSLKTEDTAVYYCAR |
| 9 | VH3-72/JH6 FR4 | WGQGTTVTVSS |
| 15 | VH3-21/JH6 FR1 | EVQLVESGGGLVKPGGSLRLSCAASGFTFS |
| 16 | VH3-21/JH6 FR2 | WVRQAPGKGLEWVS |
| 17 | VH3-21/JH6 FR3 | RFTISRDNAKNSLYLQMNSLRAEDTAVYYCAR |
| 9 | VH3-21/JH6 FR4 | WGQGTTVTVSS |
| 18 | VH1-69/JH6 FR1 | EVQLVQSGAEVKKPGSSVKVSCKASGGTFS |
| 19 | VH1-69/JH6 FR2 | WVRQAPGQGLEWMG |
| 20 | VH1-69/JH6 FR3 | RVTITADKSTSTAYMELSSLRSEDTAVYYCAR |
| 9 | VH1-69/JH6 FR4 | WGQGTTVTVSS |
| 21 | VH1-18/JH6 FR1 | EVQLVQSGAEVKKPGASVKVSCKASGYTFT |
| 19 | VH1-18/JH6 FR2 | WVRQAPGQGLEWMG |
| 22 | VH1-18/JH6 FR3 | RVTMTTDTSTSTAYMELRSLRSDDTAVYYCAR |
| 9 | VH1-18/JH6 FR4 | WGQGTTVTVSS |

TABLE 4

LIGHT CHAIN ACCEPTOR SEQUENCES

| SEQ ID No. | Protein region | Sequence 123456789012345678901234567890123456789012 |
|---|---|---|
| 23 | B3/JK4 FR1 | DIVMTQSPDSLAVSLGERATINC |
| 24 | B3/JK4 FR2 | WYQQKPGQPPKLLIY |
| 25 | B3/JK4 FR3 | GVPDRFSGSGSGTDFTLTISSLQAEDVAVYYC |
| 26 | B3/JK4 FR4 | FGGGTKVEIKR |
| 27 | L2/JK4 FR1 | EIVMTQSPATLSVSPGERATLSC |
| 28 | L2/JK4 FR2 | WYQQKPGQAPRLLIY |
| 29 | L2/JK4 FR3 | GIPARFSGSGSGTEFTLTISSLQSEDFAVYYC |
| 26 | L2/JK4 FR4 | FGGGTKVEIKR |
| 30 | L15/JK4 FR1 | DIQMTQSPSSLSASVGDRVTITC |
| 31 | L15/JK4 FR2 | WYQQKPEKAPKSLIY |
| 32 | L15/JK4 FR3 | GVPSRFSGSGSGTDFTLTISSLQPEDFATYYC |
| 26 | L15/JK4 FR4 | FGGGTKVEIKR |
| 33 | L5/JK4 FR1 | DIQMTQSPSSVSASVGDRVTITC |
| 34 | L5/JK4 FR2 | WYQQKPGKAPKLLIY |
| 32 | L5/JK4 FR3 | GVPSRFSGSGSGTDFTLTISSLQPEDFATYYC |
| 26 | L5/JK4 FR4 | FGGGTKVEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

As used herein, the term "neutralizing" refers to neutralization of biological activity of a cytokine when a binding protein specifically binds the cytokine. Preferably a neutralizing binding protein is a neutralizing antibody whose binding to hIL-12 and/or hIL-23 results in inhibition of a biological activity of hIL-12 and/or hIL-23. Preferably the neutralizing binding protein binds hIL-12 and/or hIL-23 and reduces a biologically activity of IL-12 and/or hIL-23 by at least about 20%, 40%, 60%, 80%, 85% or more. Inhibition of a biological activity of hIL-12 and/or hIL-23 by a neutralizing binding protein can be assessed by measuring one or more indicators of hIL-12 and/or hIL-23 biological activity well known in the art. For example inhibition of human phytohemagglutinin blast proliferation in a PHA blast Interferon-gamma Induction Assay (see Example 1.1.C) or inhibition of receptor binding in a human IL-12 receptor binding assay, (also see Salfeld et al., PCT publication No. WO 00/56772 A1).

The term "activity" includes activities such as the binding specificity/affinity of an antibody for an antigen, for example, an anti-hIL-12 antibody that binds to an IL-12 antigen and/or the neutralizing potency of an antibody, for example, an anti-hIL-12 antibody whose binding to hIL-12 inhibits the biological activity of hIL-12, e.g., inhibition of PHA blast proliferation or inhibition of receptor binding in a human IL-12 receptor binding assay, or PHA blast Interferon-gamma Induction Assay (see Example 1.1.C).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *BioTechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giegé et al., Chapter 1, *In Crystallization of Nucleic Acids and Proteins, a Practical Approach,* 2nd ed., (Ducruix and Giegé, eds.)(Oxford University Press, New York, 1999) pp. 1-16.

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae.*

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refers to a change or an alteration in the activity of a molecule of interest (e.g., the biological activity of hIL-12). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hIL-12). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-12 polypeptides or polypeptides, nucleic acids, carbohydrates, or any other molecules that bind to hIL-12.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of hIL-12 and/or hIL-23. Antagonists and inhibitors of hIL-12 and/or hIL-23 may include, but are not limited to, proteins, nucleic acids, carbohydrates, or any other molecules, which bind to hIL-12 and/or hIL-23.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Antibodies that Bind Human IL-12p40.

One aspect of the present invention provides isolated murine monoclonal antibodies, or antigen-binding portions thereof, that bind to IL-12p40 with high affinity, a slow off rate and high neutralizing capacity. A second aspect of the invention provides chimeric antibodies that bind IL-12p40. A third aspect of the invention provides CDR grafted antibodies, or antigen-binding portions thereof, that bind IL-12p40. A fourth aspect of the invention provides humanized antibodies, or antigen-binding portions thereof, that bind IL-12p40. Preferably, the antibodies, or portions thereof, are isolated antibodies. Preferably, the antibodies of the invention are neutralizing human anti-IL-12 and/or human anti-IL-23 antibodies.

A. Method of Making anti IL-12p40 Antibodies

Antibodies of the present invention may be made by any of a number of techniques known in the art.

1. Anti-IL-12 p40 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1.2). Briefly, mice can be immunized with an IL-12 antigen. In a preferred embodiment, the IL-12 antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with an IL-12 antigen, antibodies and/or antibody-producing cells may be obtained from the animal. An anti-IL-12 antibody-containing serum is obtained from the animal by bleeding or sacrificing the animal. The serum may be used as it is obtained from the animal, an immunoglobulin fraction may be obtained from the serum, or the anti-IL-12 antibodies may be purified from the serum. Serum or immunoglobulins obtained in this manner are polyclonal, thus having a heterogeneous array of properties.

Once an immune response is detected, e.g., antibodies specific for the antigen IL-12 are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding IL-12. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IL-12, or a portion thereof, or a cell expressing IL-12. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-IL-12p40 antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IL-12 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-IL-12p40 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcook, J. S. et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the antigen IL-12, a subunit of IL-12, or a fragment thereof, is coupled to sheep red blood cells using a linker, such as biotin, and used to identify single cells that secrete antibodies with specificity for IL-12. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-12. The amplified immunoglobulin sequences further can be manipulated in vitro, such as by in vitro affinity maturation methods such as those described in PCT Publication WO 97/29131 and PCT Publication WO 00/56772.

3. Anti-IL-12p40 Monoclonal Antibodies Using Transgenic Animals

In another embodiment of the instant invention, antibodies are produced by immunizing a non-human animal comprising some, or all, of the human immunoglobulin locus with an IL-12 antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771; 5,939,598; 5,985,615; 5,998,209; 6,075,181; 6,091,001; 6,114,598 and 6,130,364. See also WO 91/10741, published Jul. 25, 1991; WO 94/02602, published Feb. 3, 1994; WO 96/34096 and WO 96/33735, both published Oct. 31, 1996; WO 98/16654, published Apr. 23, 1998; WO 98/24893, published Jun. 11, 1998; WO 98/50433, published Nov. 12, 1998; WO 99/45031, published Sep. 10, 1999; WO 99/53049, published Oct. 21, 1999; WO 00/09560, published Feb. 24, 2000; and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

4. Anti-IL-12 Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1369-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *Proc. Natl. Acad. Sci. USA* 89:3576-3580; Garrard et al. (1991) *Bio/Technology* 9:1373-1377; Hoogenboom et al. (1991) *Nuc Acid Res* 19:4133-4137; and Barbas et al. (1991) *Proc. Natl. Acad. Sci. USA* 88:7978-7982; U.S. patent application publication 2003/0186374, and PCT Publication No. WO 97/29131, the contents of each of which are incorporated herein by reference.

The recombinant antibody library may be from a subject immunized with IL-12 or IL-23, or a portion of IL-12 or IL-23. Alternatively, the recombinant antibody library may be from a naïve subject, i.e., one who has not been immunized with IL-12 or IL-23, such as a human antibody library from a human subject who has not been immunized with human IL-12 or IL-23. Antibodies of the invention are selected by screening the recombinant antibody library with the peptide comprising human IL-12p40 to thereby select those antibodies that recognize IL-12p40. Methods for conducting such screening and selection are well known in the art, such as described in the references in the preceding paragraph. To select antibodies of the invention having particular binding affinities for hIL-12, such as those that dissociate from human IL-12 with a particular $k_{off}$ rate constant, the art-known method of surface plasmon resonance can be used to select antibodies having the desired $k_{off}$ rate constant. To select antibodies of the invention having a particular neutralizing activity for hIL-12, such as those with a particular an $IC_{50}$, standard methods known in the art for assessing the inhibition of hIL-12 activity may be used.

In one aspect, the invention pertains to an isolated antibody, or an antigen-binding portion thereof, that binds human IL-12 and/or human IL-23. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134 (WO 92/01047); PCT publications WO 90/02809; WO 91/10737; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *Am. J. Reprod. Immunol.* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *Proc. Natl. Acad. Sci. USA* 90:7995-7999 (1993); and Skerra et al., *Science* 240:1038-1041 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

B. Production of Recombinant IL-12p40 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti IL-12p40 Antibodies

Table 5 is a list of amino acid sequences of VH and VL regions of preferred anti-hIL-12p40 antibodies of the invention.

TABLE 5

List of Amino Acid Sequences of VH and VL regions

| SEQ ID No. | Protein region | | Sequence 123456789012345678901234567890 |
|---|---|---|---|
| 35 | VH 1D4 | | QVTLKESGPGILQPSQTLSLTCSFSGFSLR KSVMGVSWIRQPSGKGLEWLAHIYWDDDKY YNPSLKSRLTISKDPSRNQVFLKITSVDTA DAATYYCTRRGIRSAMDYWGQGTSVTVSS |
| | VH 1D4 CDR-H1 | Residues 31-37 of SEQ ID NO.: 35 | KSVMGVS |
| | VH 1D4 CDR-H2 | Residues 52-67 of SEQ ID NO.: 35 | HIYWDDDKYYNPSLKS |
| | VH 1D4 CDR-H3 | Residues 100-108 of SEQ ID NO.: 35 | RGIRSAMDY |
| 36 | VL 1D4 | | SVVMTQTPKFLLVSAGDRVTITCKASQSVS NDVAWYQQKPGQSPKLLIYYASNRYTGVPD RFTGSGYGTDFTFIISTVRAEDLAVYFCQQ DYNSPWTFGGGTKLEIKR |
| | VL1 D4 CDR-L1 | Residues 24-34 of SEQ ID NO.: 36 | KASQSVSNDVA |
| | VL1 D4 CDR-L2 | Residues 50-56 of SEQ ID NO.: 36 | YASNRYT |

TABLE 5-continued

List of Amino Acid Sequences of VH and VL regions

| SEQ ID No. | Protein region | | Sequence 12345678901234567890123456 7890 |
|---|---|---|---|
| | VL1 D4 CDR-L3 | Residues 89-97 of SEQ ID NO.: 36 | QQDYNSPWT |
| 37 | VH 1A6 | | QVTLKESGPGILKPSQTLSLTCSFSGFSLSTSGMGVSWIRQPSGKGLEWLAHIWWDGDNY YNPSLKSQLTISKDTSRNVFLRIATVDTA DTATYYCARRTRVNYAMDYWGQGTSVTVSS |
| | VH 1A6 CDR-H1 | Resindues 31-37 of SEQ ID NO.: 37 | TSGMGVS |
| | VH 1A6 CDR-H2 | Residues 52-67 of SEQ ID NO.: 37 | HIWWDGDNYYNPSLKS |
| | VH 1A6 CDR-H3 | Residues 100-109 of SEQ ID NO.: 37 | RTRVNYAMDY |
| 38 | VL 1A6 | | SVVMTQTPKFLLVSAGDRVTITCKASQSVS NDVAWFQQKPGQSPKLLIYYASNRYTGVPD RFTGSGYGTDFTFTISTVQAEDLAVYFCQQ DYNSPWTFGGGTKLEIKR |
| | VL 1A6 CDR-L1 | Residues 24-34 of SEQ ID NO.: 38 | KASQSVSNDVA |
| | VL 1A6 CDR-L2 | Residues 50-56 of SEQ ID NO.: 38 | YASNRYT |
| | VL 1A6 CDR-L3 | Residues 89-97 of SEQ ID NO.: 38 | QQDYNSPWT |
| 39 | VH 1D8 | | QVQLQQSGAELMKPGASVKISCKATGYTFSSYWIEWVKQRPGHGLEWIGDILPGSGSTNY NEKFKDKATFTADTSFNTAYMQLSSLTSED SAVYYCATRRFRGLDYWGQGTTLTVSS |
| | VH 1D8 CDR-H1 | Residues 31-35 of SEQ ID NO.: 39 | SYWIE |
| | VH 1D8 CDR-H2 | Residues 50-66 of SEQ ID NO.: 39 | DILPGSGSTNYNEKFKD |
| | VH 1D8 CDR-H3 | Residues 99-106 of SEQ ID NO.: 39 | RRFRGLDY |
| 40 | VL 1D8 | | SIVMTQTPKFLLVSAGDRVTITCKASQSVS NDVAWYQQKSGQSPKLLIYYASNRYTGVPD RFTGSGYGTDFTFTISTVQPEDLAVYFCQQ DYTSPFTFGSGTKLEIKR |
| | VL 1D8 CDR-L1 | Residues 24-34 of SEQ ID NO.: 40 | KASQSVSNDVA |
| | VL1D8 CDR-L2 | Residues 50-56 of SEQ ID NO.: 40 | YASNRYT |
| | VL1D8 CDR-L3 | Residues 89-97 of SEQ ID NO.: 40 | QQDYTSPFT |
| 41 | VH 3G7 | | QVQLQQSGAELMKPGASVKISCKATGYTFNDYWIEWVKQRPGHGLEWIGGFSHGSGSTNY NEKFKGKATFTADSSSNTAYMQLSSLTSED SAVYYCARRRFRGMDYWGQGTSVTVSS |
| | VH 3G7 CDR-H1 | Residues 31-35 of SEQ ID NO.: 41 | DYWIE |
| | VH 3G7 CDR-H2 | Residues 50-66 of SEQ ID NO.: 41 | GFSHGSGSTNYNEKFKG |
| | VH 3G7 CDR-H3 | Residues 99-106 of SEQ ID NO.: 41 | RRFRGMDY |

TABLE 5-continued

List of Amino Acid Sequences of VH and VL regions

| SEQ ID No. | Protein region | | Sequence 123456789012345678901234567890 |
|---|---|---|---|
| 42 | VL 3G7 | | SIVMTQTPKFLLVSAGDRVTITCKASQSVSNDVAWYQQKPGQSPKLLIYYASNRYTGVPD RFTGSGYGTDFTFTITTVQAEDLAVYFCQQDYSSPWSFGGGTKLEIKR |
| | VL 3G7 CDR-L1 | Residues 24-34 of SEQ ID NO.: 42 | KASQSVSNDVA |
| | VL 3G7 CDR-L2 | Residues 50-56 of SEQ ID NO.: 42 | YASNRYT |
| | VL 3G7 CDR-L3 | Residues 89-97 of SEQ ID NO.: 42 | QQDYSSPWS |
| 43 | VH 5E8 | | QIQLVQSGPELKKPGETVKISCKASGYSFT DYSMHWVKQAPGKGLKWMDWINTETGEPTYADDFKGRFAFSLETSASTAYLQINNLKNED TATYFCSRRRYRAFDYWGQGTTLTVSS |
| | VH 5E8 CDR-H1 | Residues 31-35 of SEQ ID NO.: 43 | DYSMH |
| | VH 5E8 CDR-H2 | Residues 50-66 of SEQ ID NO.: 43 | WINTETGEPTYADDFKG |
| | VH 5E8 CDR-H3 | Residues 99-106 of SEQ ID NO.: 43 | RRYRAFDY |
| 44 | VL 5E8 | | SIVMTQSPKFLLVSAGDRVTITCKASQSVSNDVAWYQQKLGQSPKLLIYYASNRYTGVPD RFTGSGYGTDFTFTINTVQAEDLAVYFCQQDYTSPYTFGGGTKLEIQR |
| | VL 5E8 CDR-L1 | Residues 24-34 of SEQ ID NO.: 44 | KASQSVSNDVA |
| | VL 5E8 CDR-L2 | Residues 50-56 of SEQ ID NO.: 44 | YASNRYT |
| | VL 5E8 CDR-L3 | Residues 89-97 of SEQ ID NO.: 44 | QQDYTSPYT |
| 45 | VH 8E1 | | EVKLVESGGGLVQPGGSRKLSCAASGFTFS DYGMVWVRQAPGKGLEWVASISSGSSNIYYADTVKGRFTISRDDPNNTLFLQMRSLRSED TAMYYCARNPYWGQGTTLTVSS |
| | VH 8E1 CDR-H1 | Residues 31-35 of SEQ ID NO.: 45 | DYGMV |
| | VH 8E1 CDR-H2 | Residues 50-66 of SEQ ID NO.: 45 | SISSGSSNIYYADTVKG |
| | VH 8E1 CDR-H3 | Residues 99-101 of SEQ ID NO.: 45 | NPY |
| 46 | VL 8E1 | | DIVMTQSQKFMSTSVGDRVSVTCKASQNVGTNVAWYQQKPGQSPKGLIYSASHRYSGVPD RFAGSGSGTDFTLTISNVQSEDLAEYFCQQYNSYPLTFGGGTKLELKR |
| | VL 8E1 CDR-L1 | Residues 24-34 of SEQ ID NO.: 46 | KASQNVGTNVA |
| | VL 8E1 CDR-L2 | Residues 50-56 of SEQ ID NO.: 46 | SASHRYS |
| | VL 8E1 CDR-L3 | Residues 89-97 of SEQ ID NO.: 46 | QQYNSYPLT |

TABLE 5-continued

List of Amino Acid Sequences of VH and VL regions

| SEQ ID No. | Protein region | | Sequence 12345678901234567890123456789 0 |
|---|---|---|---|
| 47 | VH 1H6 | | EVKLVESGGGLVQPGGSRKLSCAASGFTFS DYGMVWVRQAPGKGLEWVAYISSGSSTIHY ADTMKGRFTISRDNPKNTLFLQMSSLRSED TAMYYCARRHYYAMDYWGQGTSVTVSS |
| | VH 1H6 CDR-H1 | Residues 31-35 of SEQ ID NO.: 47 | DYGMV |
| | VH 1H6 CDR-H2 | Residues 50-66 of SEQ ID NO.: 47 | YISSGSSTIHYADTMKG |
| | VH 1H6 CDR-H3 | Residues 99-106 of SEQ ID NO.: 47 | RHYYAMDY |
| 48 | VL1 H6 | | SFVMTQTPKFLLVSAGDRVTITCKASQSVS NDVAWYQQKPGQSPKLLIYYASNRYTGVPD RFTGTGYGTDFTFTISTVQAEDLAVYFCQQ DYTSPFTFGSGTKLEIKR |
| | VL 1H6 CDR-L1 | Residues 24-34 of SEQ ID NO.: 48 | KASQSVSNDVA |
| | VL 1H6 CDR-L2 | Residues 50-56 of SEQ ID NO.: 48 | YASNRYT |
| | VL 1H6 CDR-L3 | Residues 89-97 of SEQ ID NO.: 48 | QQDYTSPFT |
| 49 | VH 3A11 | | EVQLQQSGADLEKPGASVKLSCTASGFNIK DTFMHWVKQRPEQGLEWIGRIDPANGHTKY DPKFQGKATITADTSSNTAYLQLSSLTSED TAVYYCARWGQFGLLWNAMDYWGQGTSVTV SS |
| | VH 3A11 CDR-H1 | Residues 31-35 of SEQ ID NO.: 49 | DTFMH |
| | VH 3A11 CDR-H2 | Residues 50-66 of SEQ ID NO.: 49 | RIDPANGHTKYDPKFQG |
| | VH 3A11 CDR-H3 | Residues 99-111 of SEQ ID NO.: 49 | WGQFGLLWNAMDY |
| 50 | VL 3A11 | | DIVLTQSPGSLAVSLGQRATISCRASESVD NYGISFMNWFQQKPGQPPKLLIYYAASNQGS GVPARFSGSGSGTDFSLDIHPMEEDDTAMY FCQQSKEVPPTFGGGTKLEIKR |
| | VL 3A11 CDR-L1 | Residues 24-38 of SEQ ID NO.: 50 | RASESVDNYGISFMN |
| | VL 3A11 CDR-L2 | Residues 54-60 of SEQ ID NO.: 50 | YAASNQGS |
| | VL 3A11 CDR-L3 | Residues 93-101 of SEQ ID NO.: 50 | QQSKEVPPT |
| 51 | VH 4B4 | | QVTLKESGPGILKPSQTLSLTCSLSGFSLS TSGMGVSWIRQPSGKGLEWLAHIWWDGDSY SNPSLRSRLTISRDTSRNQVFLRIATVDTA DTATYYCARRTRVNYAMDYWGQGTSVTVSS |
| | VH 4B4 CDR-H1 | Residues 31-37 of SEQ ID NO.: 51 | TSGMGVS |
| | VH 4B4 CDR-H2 | Residues 52-67 of SEQ ID NO.: 51 | HIWWDGDSYSNPSLRS |
| | VH 4B4 CDR-H3 | Residues 100-109 of SEQ ID NO.: 51 | RTRVNYAMDY |

TABLE 5-continued

List of Amino Acid Sequences of VH and VL regions

| SEQ ID No. | Protein region | | Sequence 12345678901234567890123456 7890 |
|---|---|---|---|
| 52 | VL 4B4 | | SVVMTQTPKFLLVSAGDRVTMTCKASQSVS NDVAWFQQKPGQSPKLLIYYASNRYTGVPD RFTGSGYGTDFTFTISTVQAEDLAVYFCQQ DYNSPWTFGGGTKLEIKR |
| | VL 4B4 CDR-L1 | Residues 24-34 of SEQ ID NO.: 52 | KASQSVSNDVA |
| | VL 4B4 CDR-L2 | Residues 50-56 of SEQ ID NO.: 52 | YASNRYT |
| | VL 4B4 CDR-L3 | Residues 89-97 of SEQ ID NO.: 52 | QQDYNSPWT |
| 53 | VH 7G3 | | EVQLQQSGAEFVRSGASVKLSCTASGLNIK DYYIHWVKQRPEQVLDWIGWIDPENGYSEY APRFQDKATMTADTSSNTAYLHLSSLTSED TAVYYCNPGELARYFDYWGQGTTLTVSS |
| | VH 7G3 CDR-H1 | Residues 31-35 of SEQ ID NO.: 53 | DYYIH |
| | VH 7G3 CDR-H2 | Residues 50-66 of SEQ ID NO.: 53 | WIGWIDPENGYSEYAPRFQD |
| | VH 7G3 CDR-H3 | Residues 99-107 of SEQ ID NO.: 53 | GELARYFDY |
| 54 | VL 7G3 | | DIVLSQSPATLSVTPGDSVSLSCRASQSIS KNLHWYQQKSHESPRLLIKYTSQSISGIPS RFSGSGSGTDFTLSINSVETEDFGMYFCQQ SISWPLTFGAGTKLELKR |
| | VL 7G3 CDR-L1 | Residues 24-34 of SEQ ID NO.: 54 | RASQSISKNLH |
| | VL 7G3 CDR-L2 | Residues 50-56 of SEQ ID NO.: 54 | YTSQSIS |
| | VL 7G3 CDR-L3 | Residues 89-97 of SEQ ID NO.: 54 | QQSISWPLT |

The foregoing isolated anti-IL-12p40 antibody CDR sequences establish a novel family of IL-12p40 binding proteins, isolated in accordance with this invention, and comprising polypeptides that include the CDR sequences listed in Table 6 below. To generate and to select CDR's of the invention having preferred IL-12p40 binding and/or neutralizing activity with respect to hIL-12 and or hIL-23, standard methods known in the art for generating binding proteins of the present invention and assessing the IL-12 and or IL-23 binding and/or neutralizing characteristics of those binding protein may be used, including but not limited to those specifically described herein.

TABLE 6

Consensus IL-12p40 CDR affinity ligands
(alternative residues are listed below each amino acid position; - indicates residue may be absent).

| CDR region | Sequence Identifier | Consensus Sequence |
|---|---|---|
| CDR-H1 | SEQ ID NO.: 55 | $X_1$ $X_2$ $X_3$ $X_4$ $X_5$ $X_6$ $X_7$<br>D Y Y I H - -<br>K S V M G V S<br>T T G   E<br>S   W   V<br>    S<br>    F |
| CDR-H2 | SEQ ID NO.: 56 | $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$ $X_{18}$ $X_{19}$ $X_{20}$<br>H I Y W D D D K Y Y N P S L K - - - - -<br>D F W P G G G N T N Y N E K F S D F Q D<br>G     L H E S S S P T   A D D V K G |

TABLE 6-continued

Consensus IL-12p40 CDR affinity ligands
(alternative residues are listed below each
amino acid position; - indicates residue may be absent).

| CDR region | Sequence Identifier | Consensus Sequence |
|---|---|---|

```
                          W   S T A T P E I H   D P T M Q R
                          S   N S I N   T N K   S     Y R P
                          Y   D         H   S         A
                          R   G             G

CDR-H3   SEQ ID    X1 X2 X3 X4 X5 X6 X7 X8 X9 X10 X11 X12 X13
         NO.: 57   R  G  I  R  S  A  M  D  Y  -   -   -   -
                   N  T  R  V  N  Y  A  M  D  Y   M   D   Y
                   W  R  F  Y  G  L  D  Y  N  A
                      P  Y  F  A  F  L  W
                      H  Q  A  R  M  F

CDR-L1   SEQ ID    X1 X2 X3 X4 X5 X6 X7 X8 X9 X10 X11 X12 X13 X14 X15
         NO.: 58   K  A  S  Q  S  V  S  N  D  V   A   -   -   -   -
                   R        E  N  I  G  T  N  G   I   S   F   M   N
                                     D  K  Y  L   H

CDR-L2   SEQ ID    X1 X2 X3 X4 X5 X6 X7 X8
         NO.: 59   Y  A  S  N  R  Y  T  -
                   S  T  A  H  N  Q  S  S
                               S  S  I  G
                               Q

CDR-L3   SEQ ID    X1 X2 X3 X4 X5 X6 X7 X8 X9
         NO.: 60   Q  Q  D  Y  N  S  P  W  T
                         Y  N  T  Y     F  S
                         S  K  S  V     Y
                            I  E  W     L
                                        P
```

2. Anti IL-12p40 Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail in Example 2.1. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, *Proc. Natl. Acad. Sci USA.* 81:6851-6855; Neuberger et al., 1984, *Nature* 312:604-608; Takeda et al., 1985, *Nature* 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti human IL-12 antibodies described in section 1 with a human IgG1 constant region. In a specific embodiment the chimeric antibody of the invention comprises a heavy chain variable region ($V_H$) comprising the amino acid sequence of SEQ ID NO: 35; SEQ ID NO: 37; SEQ ID NO: 39; SEQ ID NO: 41; SEQ ID NO: 43; SEQ ID NO: 45; SEQ ID NO: 47; SEQ ID NO: 49; SEQ ID NO: 51; or SEQ ID NO: 53 and a light chain variable region ($V_L$) comprising the amino acid sequence of SEQ ID NO: 36; SEQ ID NO: 38; SEQ ID NO: 40; SEQ ID NO: 42; SEQ ID NO: 44; SEQ ID NO: 46; SEQ ID NO: 48; SEQ ID NO: 50; SEQ ID NO: 52; or SEQ ID NO: 54.

3. Anti IL-12p40 CDR Grafted Antibodies

CDR-grafted antibodies of the invention comprise heavy and light chain variable region sequences from a human antibody wherein one or more of the CDR regions of $V_H$ and/or $V_L$ are replaced with CDR sequences of the murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing chimeric antibodies are known in the art and discussed in detail in Example 2.2. (also see EP 0 239 400; PCT publication WO 91/09967; U.S. Pat. Nos. 5,225,539; 5,530,101; and 5,585,089), veneering or resurfacing (EP 0 592 106; EP 0 519 596; Padlan, *Molecular Immunology* 28(4/5):489-498 (1991); Studnicka et al., *Protein Engineering* 7(6):805-814 (1994); Roguska et al., *Proc. Natl. Acad. Sci. USA* 91:969-973 (1994), and chain shuffling (U.S. Pat. No. 5,565,352).

In a specific embodiment the invention provides CDR grafted antibodies with $V_H$ and/or $V_L$ chains as described in Table 7.

TABLE 7

CDR Grafted antibodies

| SEQ ID No. | Protein region | Sequence 12345678901234567890123456789 0 |
|---|---|---|
| 61 | VH 1D4.1 | |
| (6) | (VH2-70/JH6 FR1) | EVTLRESGPALVKPTQTLTLTCTFSGFSLS |
| (7) | (VH2-70/JH6 FR2) | KSVMGVSWIRQPPGKALEWLAHIYWDDDKY |
| (8) | (VH2-70/JH6 FR3) | YNPSLKSRLTISKDTSKNQVVLTMTNMDPV |
| (9) | (VH2-70/JH6 FR4) | DTATYYCARRGIRSAMDYWGQGTTVTVSS |
| 62 | VL 1D4.1 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYNSPWTFGGGTKVEIKR |
| 63 | VH 1D4.2 | |
| (10) | (VH2-26/JH6 FR1) | EVTLKESGPVLVKPTETLTLTCTVSGFSLS |
| (7) | (VH2-70/JH6 FR2) | KSVHGVSWIRQPPGKALEWLAHIYWDDDKY |
| (11) | (VH2-70/JH6 FR3) | YNPSLKSRLTISKDTSKSQVVLTMTNMDPV |
| (9) | (VH2-70/JH6 FR4) | DTATYYCARRGIRSAMDYWGQGTTVTVSS |
| 64 | VL 1D4.2 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGIPA |
| (29) | (L2/JK4 FR3) | RFSGSGSGTEFTLTISSLQSEDFAVYYCQQ |
| (26) | (B3/JK4 FR4) | DYNSPWTFGGGTKVEIKR |
| 65 | VH 1D4.3 | |
| (6) | (VH2-70/JH6 FR1) | EVTLRESGPALVKPTQTLTLTCTFSGFSLS |
| (7) | (VH2-70/JH6 FR2) | KSVMGVSWIRQPPGKALEWLAHIYWDDDKY |
| (8) | (VH2-70/JH6 FR3) | YNPSLKSRLTISKDTSKNQVVLTMTNMDPV |
| (9) | (VH2-70/JH6 FR4) | DTATYYCARRGIRSAMDYWGQGTTVTVSS |
| 66 | VL 1D4.3 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGIPA |
| (29) | (L2/JK4 FR3) | RFSGSGSGTEFTLTISSLQSEDFAVYYCQQ |
| (26) | (B3/JK4 FR4) | DYNSPWTFGGGTKVEIKR |
| 67 | VH 1A6.1 | |
| (6) | (VH2-70/JH6 FR1) | EVTLRESGPALVKPTQTLTLTCTFSGFSLS |
| (7) | (VH2-70/JH6 FR2) | TSGMGVSWIRQPPGKALEWLAHIWWDGDNY |
| (8) | (VH2-70/JH6 FR3) | YNPSLKSRLTISKDTSKNQVVLTMTNMDPV |
| (9) | (VH2-70/JH6 FR4) | DTATYYCARRTRVNYAMDYWGQGTTVTVSS |
| 68 | VL 1A6.1 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYNSPWTFGGGTKVEIKR |
| 69 | VH 1A6.2 | |
| (10) | (VH2-26/JH6 FR1) | EVTLKESGPVLVKPTETLTLTCTVSGFSLS |
| (7) | (VH2-70/JH6 FR2) | TSGMGVSWIRQPPGKALEWLAHIWWDGDNY |
| (11) | (VH2-26/JH6 FR3) | YNPSLKSRLTTSKDTSKSQVVLTMTNMDPV |
| (9) | (VH2-70/JH6 FR4) | DTATYYCARRTRVNYAMDYWGQGTTVTVSS |
| 70 | VL 1A6.2 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGTPA |
| (29) | (L2/JK4 FR3) | RFSGSGSGTEFTLTTSSLQSEDFAVYYCQQ |
| (26) | (B3/JK4 FR4) | DYNSPWTFGGGTKVETKR |
| 71 | VH 8E1.1 | |
| (12) | (VH3-72/JH6 FR1) | EVQLVESGGGLVQPGGSLRLSCAASGFTFS |
| (13) | (VH3-72/JH6 FR2) | DYGKVWVRQAPGKGLEWVGSISSGSSNIYY |
| (14) | (VH3-72/JH6 FR3) | ADTVKGRFTISRDDSKNSLYLQMNSLKTED |
| (9) | (VH2-70/JH6 FR4) | TAVYYCARNPYWGQGTTVTVSS |
| 72 | VL 8E1.1 | |
| (30) | (L15/JK4 FR1) | DIQMTQSPSSLSASVGDRVTITCKASQNVG |
| (31) | (L15/JK4 FR2) | TNVAWYQQKPEKAPKSLIYSASHRYSGVPS |
| (32) | (L15/JK4 FR3) | RFSGSGSGTDFTLTISSLQPEDFATYYCQQ |
| (26) | (B3/JK4 FR4) | YNSYPLTFGGGTKVEIKR |
| 73 | VH 8E1.2 | |
| (15) | (VH3-21/JH6 FR1) | EVQLVESGGGLVKPGGSLRLSCAASGFTFS |
| (16) | (VH3-21/JH6 FR2) | DYGMVWVRQAPGKGLEWVSSISSGSSNIYY |
| (17) | (VH3-21/JH6 FR3) | ADTVKGRFTISRDNAKNSLYLQMNSLRAED |
| (9) | (VH2-70/JH6 FR4) | TAVYYCARNPYWGQGTTVTVSS |
| 74 | VL 8E1.2 | |
| (33) | (L15/JK4 FR1) | DIQMTQSPSSVSASVGDRVTITCKASQNVG |
| (34) | (L15/JK4 FR2) | TNVAWYQQKPGKAPKLLIYSASHRYSGVPS |
| (32) | (L15/JK4 FR3) | RFSGSGSGTDFTLTISSLQPEDFATYYCQQ |
| (26) | (B3/JK4 FR4) | YNSYPLTGGGTKVEIKR |
| 75 | VH 3G7.1 | |
| (18) | (VHZ-69/JH6 FR1) | EVQLVQSGAEVKKPGSSVKVSCKASGGTFS |
| (19) | (VH1-69/JH6 FR2) | DYWIEWVRQAPGQGLEWMGGFSHGSGSTNY |
| (20) | (VH1-69/JH6 FR3) | NEKFKGRVTITADKSTSTAYMELSSLRSED |
| (9) | (VH2-70/JH6 FR4) | TAVYYCARRRFRGMDYWGQGTTVTVSS |
| 76 | VL 3G7.1 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYSSPWSGGGTKVEIKR |
| 77 | VH 3G7.2 | |
| (21) | (VHZ-18/JH6 FR1) | EVQLVQSGAEVKKPGASVKVSCKASGYTFT |
| (19) | (VH1-69/JH6 FR2) | DYWIEWVRQAPGQGLEWMGGFSHGSGSTNY |
| (22) | (VH1-18/JH6 FR3) | NEKFKGRVTMTTDTSTSTAYMELRSLRSDD |
| (9) | (VH2-70/JH6 FR4) | TAVYYCARRRRGMDYWGQGTTVTVSS |
| 78 | VL 3G7.2 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGIPA |
| (29) | (L2/JK4 FR3) | RFSGSGSGTEFTLTISSLQSEDFAVYYCQQ |
| (26) | (B3/JK4 FR4) | DYSSPWSGGGTKVEIKR |
| 67 | VH1A6.5 | |
| (6) | (VH2-70/JH6 FR1) | EVTLRESGPALVKPTQTLTLTCTFSGFSLS |

TABLE 7-continued

CDR Grafted antibodies

| SEQ ID No. | Protein region | Sequence 123456789012345678901234567890 |
|---|---|---|
| (7) | (VH2-70/JH6 FR2) | TSGMGVSWIRQPPGKALEWLAHIWWDGDNY |
| (8) | (VH2-70/JH6 FR3) | YNPSLKSRLTISKDTSKNQVVLTMTNMDPV |
| (9) | (VH2-70/JH6 FR4) | DTATYYCARRTRVNYAMDYWGQGTTVTVSS |
| 70 | VL 1A6.5 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGIPA |
| (29) | (L2/JK4 FR3) | RFSGSGSGTEFTLTISSLQSEDFAVYYCQQ |
| (26) | (B3/JK4 FR4) | DYNSPWTFGGGTKVEIKR |
| 69 | VH 1A6.6 | |
| (10) | (VH2-26/JH6 FR1) | EVTLKESGPVLVKPTETLTLTCTVSGFSLS |
| (7) | (VH2-70/JH6 FR2) | TSGMGVSWIRQPPGKALEWLAHIWWDGDNY |
| (11) | (VH2-26/JH6 FR3) | YNPSLKSRLTISKDTSKSQVVLTMTNMDPV |
| (9) | (VH2-70/JH6 FR4) | DTATYYCARRTRVNYAMDYWGQGTTVTVSS |
| 68 | VL 1A6.6 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYNSPWTFGGGTKVEIKR |

4. Anti IL-12p40 Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., world wide web ncbi.nlm.nih.gov/entrez-/query.fcgi; atcc.org/phage/hdb.html; sciquest.com/; abcam.com/; antibodyresource.com/onlinecomp.html; public.iastate.edu/.about.pedro/research_tools.html; mgen.uni-heidelberg.de/SD/IT/IT.html; whfreeman.com/immunology/CH-05/kuby05.htm; library.thinkquest.org/12429/Immune/Antibody.html; hhmi.org/grants/lectures/1996/vlab/; path.cam.ac.uk/.about.mrc7/m-ikeimages.html; antibodyresource.com/; mcb.harvard.edu/BioLinks/Immuno-logy.html.immunologylink.com; pathbox.wustl.edu/.about.hcenter/index.-html; biotech.ufl.edu/.about.hcl/; www.pebio.com/pa/340913/340913.html-; nal.usda.gov/awic/pubs/antibody/; m.ehime-u.acjp/.about.yasuhito-/Elisa.html; biodesign.com/table.asp; icnet.uk/axp/facs/davies/lin-ks.html; biotech.ufl.edu/.about.fccl/protocol.html; isac-net.org/sites_geo.html; aximtl.imt.uni-marburg.de/.about.rek/AEP-Start.html; baserv.uci.kun.nl/.about.jraats/linksl.html; recab.uni-hd.de/immuno.bme.nwu.edu/; mrc-cpe.cam.ac.uk/imt-doc/public/INTRO.html; ibt.unam.mx/vir/V_mice.html; imgt.cnusc.fr:8104/; biochem.ucl.ac.uk/.about.martin/abs/index.html; antibody.bath.ac.uk/; abgen.cvm.tamu.edu/lab/wwwabgen.html; unizh.ch/.about.honegger/AHOsem-inar/Slide01.html; cryst.bbk.ac.uk/.about.ubcg07s/; nimr.mrc.ac.uk/CC/ccaewg/ccaewg.htm; path.cam.ac.uk/.about.mrc7/h-umanisation/TAHHP.html; ibt.unam.mx/vir/structure/stat_aim.html; biosci.missouri.edu/smithgp/index.html; cryst.bioc.cam.ac.uk/.abo-ut.fmolina/Web-pages/Pept/spottech.html; jerini.de/frroducts.htm; patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323-327 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. USA 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., Proc. Natl. Acad. Sci. USA 91:969-973 (1994); International applications Nos. PCT/US98/16280 (WO 99/06834); PCT/US96/18978 (WO 97/20032); PCT/US91/09630 (WO 92/11272); PCT/US91/05939 (WO 92/03461); PCT/US94/01234 (WO 94/18219); PCT/GB91/01134 (WO 92/01047); PCT/GB92/01755 (WO 93/06213); PCT publication Nos. WO 91/09967; WO 90/14443; WO 90/14424; WO 90/14430; European Pat. Nos. EP 0 592 106; EP 0 519 596, EP 0 239 400; U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, each entirely incorporated herein by reference, included references cited therein.

C. Production of Antibodies and Antibody-Producing Cell Lines

Preferably, anti-IL-12p40 antibodies of the present invention, exhibit a high capacity to reduce or to neutralize IL-12 activity, e.g., as assessed by any one of several in vitro and in vivo assays known in the art (e.g., see Example 1.1.C). For example, these antibodies neutralize IL-12-induced production of interferon gamma by PHA blasts with $IC_{50}$ values in the range of at least about $10^{-8}$ M, about $10^{-9}$ M, or about $10^{-10}$ M. Preferably, anti-IL-12p40 antibodies of the present invention, also exhibit a high capacity to reduce or to neutralize IL-23 activity In preferred embodiments, the isolated antibody, or antigen-binding portion thereof, binds human IL-12p40, wherein the antibody, or antigen-binding portion thereof, dissociates from human IL-12p40 with a $k_{off}$ rate constant of about $0.1 s^{-1}$ or less, as determined by surface plasmon resonance, or which inhibits human IL-12 and/or human IL-23 activity with an $IC_{50}$ of about $1\times10^{-6}$ M or less. Alternatively, the antibody, or an antigen-binding portion thereof, may dissociate from human IL-12p40 with a $k_{off}$ rate constant of about $1\times10^{-2}s^{-1}$ or less, as determined by surface plasmon resonance, or may inhibit human IL-12 and/or human IL-23 activity with an $IC_{50}$ of about $1\times10^{-7}$ M or less. Alternatively, the antibody, or an antigen-binding portion thereof, may dissociate from human IL-12p40 with a $k_{off}$ rate constant of about $1\times10^{-3}s^{-1}$ or less, as determined by surface plasmon resonance, or may inhibit human IL-12 and/or human IL-23 with an $IC_{50}$ of about $1\times10^{-8}$ M or less. Alternatively, the antibody, or an antigen-binding portion thereof, may dissociate from human IL-12p40 with a $k_{off}$ rate constant of about $1\times10^{-4}s^{-1}$ or less, as determined by surface plasmon resonance, or may inhibit IL-12 and/or human IL-23 activity with an $IC_{50}$ of about $1\times10^{-9}$ M or less. Alternatively, the antibody, or an antigen-binding portion thereof, may dissociate from human IL-12p40 with a $k_{off}$ rate constant of about $1\times10^{-5}s^{-1}$ or less, as determined by surface plasmon resonance, or may inhibit IL-12 and/or human IL-23 activity with an $IC_{50}$ of about $1\times10^{-10}$ M or less. Alternatively, the antibody, or an antigen-binding portion thereof, may dissociate from human IL-12p40 with a $k_{off}$ rate constant of about $1\times10^{-5}s^{-1}$ or less, as determined by surface plasmon resonance, or may inhibit IL-12 and/or human IL-23 activity with an $IC_{50}$ of about $1\times10^{-11}$ M or less.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter et al. U.S. Pat. Nos. 5,648,260 and 5,624,821). The Fc portion of an antibody mediates several important effector functions e.g., cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably the invention relates to crystals of whole anti-IL-12p40 antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02/072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *J. Exp. Med.* (1988) 168:1099-1109; Wright, A., et al., *EMBO J.* (1991) 10: 2717-2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO 2003/016466 A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells of the invention in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-180, as well as, European Patent No. EP 1 176 195; PCT Publications WO 03/035835; WO 99/54342, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (published U.S patent applications 2004/0018590 and 2002/0137134 and PCT publication WO 2005/100584 A2).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of Anti-IL-12p40 Antibodies

Given their ability to bind to human IL-12p40, the anti-human IL-12p40 antibodies, or portions thereof, of the invention can be used to detect IL-12 and/or human IL-23 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting IL-12 and/or human IL-23 in a biological sample comprising contacting a biological sample with an antibody, or antibody portion, of the invention and detecting either the antibody (or antibody portion) bound to IL-12 and/or human IL-23 or unbound antibody (or antibody portion), to thereby detect IL-12 and/or human IL-23 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Alternative to labeling the antibody, human IL-12 can be assayed in biological fluids by a competition immunoassay utilizing rhIL-12 standards labeled with a detectable substance and an unlabeled anti-human IL-12p40 antibody. In this assay, the biological sample, the labeled rhIL-12 standards and the anti-human IL-12p40 antibody are combined and the amount of labeled rhIL-12 standard bound to the unlabeled antibody is determined. The amount of human IL-12 in the biological sample is inversely proportional to the amount of labeled rhIL-12 standard bound to the anti-IL-12p40 antibody. Similarly, human IL-23 can also be assayed in biological fluids by a competition immunoassay utilizing rhIL-23 standards labeled with a detectable substance and an unlabeled anti-human IL-12p40 antibody.

The antibodies and antibody portions of the invention preferably are capable of neutralizing human IL-12 and/or human IL-23 activity both in vitro and in vivo. Accordingly, such antibodies and antibody portions of the invention can be used to inhibit hIL-12 and/or hIL-23 activity, e.g., in a cell culture containing hIL-12 and/or hIL-23, in human subjects or in other mammalian subjects having IL-12 and/or hIL-23 with which an antibody of the invention cross-reacts.

In one embodiment, the invention provides a method for inhibiting hIL-12 and/or hIL-23 activity comprising contacting hIL-12 and/or hIL-23 with an antibody or antibody portion of the invention such that hIL-12 and/or hIL-23 activity is inhibited. For example, in a cell culture containing, or suspected of containing hIL-12 and/or hIL-23, an antibody or antibody portion of the invention can be added to the culture medium to inhibit hIL-12 and/or hIL-23 activity in the culture.

In another embodiment, the invention provides a method for reducing hIL-12 and/or hIL-23 activity in a subject, advantageously from a subject suffering from a disease or disorder in which IL-12 or IL-23 activity is detrimental. The invention provides methods for reducing IL-12 and/or IL-23 activity in a subject suffering from such a disease or disorder, which method comprises administering to the subject an antibody or antibody portion of the invention such that IL-12 and/or IL-23 activity in the subject is reduced. Preferably, the IL-12 is human IL-12, the IL-23 is human IL-23, and the subject is a human subject. Alternatively, the subject can be a mammal expressing an IL-12 and/or IL-23 to which an antibody of the invention is capable of binding. Still further the subject can be a mammal into which IL-12 and/or IL-23 has been introduced (e.g., by administration of IL-12 and/or IL-23 or by expression of an IL-12 and/or IL-23 transgene). An antibody of the invention can be administered to a human subject for therapeutic purposes. Moreover, an antibody of the invention can be administered to a non-human mammal expressing an IL-12 and/or IL-23 with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which IL-12 and/or IL-23 activity is detrimental" is intended to include diseases and other disorders in which the presence of IL-12 and/or IL-23 in a subject suffering from the disorder has been shown to be or is suspected of being either responsible for the pathophysiology of the disorder or a factor that contributes to a worsening of the disorder. Accordingly, a disorder in which IL-12 and/or IL-23 activity is detrimental is a disorder in which reduction of IL-12 and/or IL-23 activity is expected to alleviate the symptoms and/or progression of the disorder. Such disorders may be evidenced, for example, by an increase in the concentration of IL-12 and/or IL-23 in a biological fluid of a subject suffering from the disorder (e.g., an increase in the concentration of IL-12 and/or IL-23 in serum, plasma, synovial fluid, etc. of the subject), which can be detected, for example, using an anti-IL12p40 antibody as described above. Non-limiting examples of disorders that can be treated with the antibodies of the invention include those disorders discussed in the section below pertaining to pharmaceutical compositions of the antibodies of the invention.

D. Pharmaceutical Composition

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which IL-12 and/or IL-23 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540 and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, *CRC Crit. Ref Biomed. Eng.* 14: 201-240; Buchwald et al., 1980, *Surgery* 88:507; Saudek et al., 1989, *N. Engl. J. Med.* 321:574-579). In another embodiment, polymeric materials can be used to achieve controlled or sustained release of the therapies of the invention (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Langer and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105-112); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, J. M., Chapter 6, *In Medical Applications of Controlled Release, Vol. II, Applications and Evaluation*, (Langer and Wise, eds.) (CRC Press, Inc., Boca Raton, 1984), pp. 115-138.

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; PCT publication WO 91/05548; PCT publication WO 96/20698; Ning et al., 1996, "Intratumoral Radioimmunotherapy of a Human Colon Cancer Xenograft Using a Sustained-Release Gel," *Radiotherapy & Oncology* 39:179-189; Song et al., 1995, "Antibody Mediated Lung Targeting of Long-Circulating Emulsions," *PDA Journal of Pharmaceutical Science &Technology* 50:372-377; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon®) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540 and 4,880,078; and PCT Publication Nos. WO 92/19244; WO 97/32572; WO 97/44013; WO 98/31346 and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachet indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO 2004/078140, US 2006/0104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-12 activity is detrimental. For example, an anti-hIL-12 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to IL-12 or fragment thereof is linked to a half-life extending vehicle known in the art. Such vehicles include, but are not limited to, the Fc domain, polyethylene glycol, and dextran. Such vehicles are described, e.g., in U.S. Pat. No. 6,660,843 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; and Robinson, C., 1993, *Trends Biotechnol.* 11(5): 155-215. Methods commonly known in the art of recombinant DNA technology which can be used are described in Ausubel et al. (eds.), *Current Protocols in Molecular Biology*, John Wiley &Sons, NY (1993); and Kriegler, *Gene Transfer and Expression, A Laboratory Manual*, Stockton Press, NY (1990). Detailed descriptions of various methods of gene therapy are disclosed in US 2005/0042664 A1 which is incorporated herein by reference.

Interleukin 12 plays a critical role in the pathology associated with a variety of diseases involving immune and inflammatory elements. These diseases include, but are not limited to, rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, *chlamydia, yersinia* and *salmonella* associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, drug-induced hepatitis, non-alcoholic steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3® therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic arteriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkins lymphoma, occlusion of the abdominal aorta and its branches, occlusive arterial disorders, OKT3® therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemaphagocytic syndrome, Wernicke-Korsakoff syndrome, Wilson's disease, xenograft rejection of any organ or tissue. (see Peritt et al. PCT publication No. WO 2002/097048 A2; Leonard et al., PCT publication No. WO 95/24918 A1; and Salfeld et al., PCT publication No. WO 00/56772 A1).

The antibodies, and antibody portions of the invention can be used to treat humans suffering from autoimmune diseases, in particular those associated with inflammation, including, rheumatoid spondylitis, allergy, autoimmune diabetes, autoimmune uveitis. Preferably, the antibodies of the invention or antigen-binding portions thereof, are used to treat rheumatoid arthritis, Crohn's disease, multiple sclerosis, insulin dependent diabetes mellitus and psoriasis.

An antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Binding proteins described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the anti-IL-12 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-12 function; especially preferred are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Nonlimiting additional agents which can also be used in combination with an IL-12 or IL-23 antibody, or antigen-binding portion thereof, to treat rheumatoid arthritis include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, 5295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), 5284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g.,

*Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), 5282) and thalidomide-related drugs (e.g., Celgen); leflunomide (anti-inflammatory and cytokine inhibitor; see e.g., *Arthritis & Rheumatism* (1996) Vol. 39, No. 9 (supplement), 5131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents.

In one embodiment, the IL-12 antibody, or antigen-binding portion thereof, is administered in combination with one of the following agents for the treatment of rheumatoid arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propoxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, an IL-12 or IL-23 antibody, or antigen-binding portion thereof, is administered for the treatment of an IL-12 or IL-23 related disorder in combination with one of the above mentioned agents for the treatment of rheumatoid arthritis.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and antiinflammatory cytokines (e.g., IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) inhibitors and PDE4 inhibitors. Antibodies of the invention, or antigen binding portions thereof, can be combined with corticosteroids, for example, budenoside and dexamethasone. Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. Antibodies of the invention or antigen binding portion thereof may also be used with T cell signaling inhibitors, for example, tyrosine kinase inhibitors 6-mercaptopurines. Antibodies of the invention, or antigen binding portions thereof, can be combined with IL-11. Antibodies of the invention, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD19, CD20, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and antiinflammatory cytokines (e.g., IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The antibodies of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for angina with which an antibody, or antibody portion, of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for ankylosing spondylitis with which an antibody, or antibody portion, of the invention can be combined include the following: ibuprofen, diclofenac and misoprostol, naproxen, meloxicam, indomethacin, diclofenac, celecoxib, rofecoxib, Sulfasalazine, Methotrexate, azathioprine, minocyclin, prednisone, etanercept, infliximab.

Non-limiting examples of therapeutic agents for asthma with which an antibody, or antibody portion, of the invention can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which an antibody, or antibody portion, of the invention can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which an antibody, or antibody portion, of the invention can be combined include the following: Interferon-alpha-2a, Interferon-alpha-2b, Interferon-alpha con1, Interferon-alpha-n1, Pegylated interferon-alpha-2a, Pegylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for idiopathic pulmonary fibrosis with which an antibody, or antibody portion, of the invention can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone hcl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for Myocardial Infarction with which an antibody, or antibody portion, of the invention can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for Psoriasis with which an antibody, or antibody portion, of the invention can be combined include the following: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for Psoriatic Arthritis with which an antibody, or antibody portion, of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Restenosis with which an antibody, or antibody portion, of the invention can be combined include the following: sirolimus, paclitaxel, everolimus, tacrolimus, ABT-578, acetaminophen.

Non-limiting examples of therapeutic agents for Sciatica with which an antibody, or antibody portion, of the invention can be combined include the following: hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, temazepam.

Preferred examples of therapeutic agents for SLE (Lupus) in which an antibody or an antigen binding portion can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. Antibodies of the invention or antigen binding portions thereof, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Antibodies of the invention or antigen binding portion thereof may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Antibodies of the invention, or antigen binding portions thereof, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the invention or antigen binding portion thereof may also be used with LJP 394 (abetimus), agents that deplete or inactivate B-cells, for example, Rituximab (anti- CD20 antibody), lymphostat-B (anti-BlyS antibody), TNF antagonists, for example, anti-TNF antibodies, D2E7 (PCT Publication No. WO 97/29131; HUMIRA), CA2 (REMICADE), CDP 571, TNFR-Ig constructs, (p75TNFRIgG (ENBREL) and p55TNFRIgG (LENERCEPT)).

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Generation and Isolation of Anti Human IL-12 Monoclonal Antibodies

Example 1.1

Assays to Identify Anti Human IL-12 Antibodies

Throughout Example 1 the following assays were used to identify and characterize anti human IL-12 antibodies unless otherwise stated.

Example 1.1.A

ELISA

Enzyme Linked Immunosorbent Assays to screen for antibodies that bind human IL-12 were performed as follows.

Example 1.1.A.1

ELISA to Detect Binding of Anti Human IL-12 Antibodies to IL-12 p70

ELISA plates (Corning Costar, Acton, Mass.) were coated with 50 µL/well of 5 µg/ml goat anti-mouse IgG Fc specific (Pierce #31170, Rockford, Ill.) in Phosphate Buffered Saline (PBS) overnight at 4 degrees Celsius. Plates were washed once with PBS containing 0.05% Tween-20. Plates were blocked by addition of 200 µL/well blocking solution diluted to 2% in PBS (BioRad #170-6404, Hercules, Calif.) for 1 hour at room temperature. Plates were washed once after blocking with PBS containing 0.05% Tween-20.

Fifty microliters per well of mouse sera or hybridoma supernatants diluted in PBS containing 0.1% Bovine Serum Albumin (BSA) (Sigma, St. Louis, Mo.) was added to the ELISA plate prepared as described above and incubated for 1 hour at room temperature. Wells were washed three times with PBS containing 0.05% Tween-20. Fifty microliters of biotinylated recombinant purified human IL-12 p70 diluted to 100 ng/mL in PBS containing 0.1% BSA was added to each well and incubated for 1 hour at room temperature. Plates were washed 3 times with PBS containing 0.05% Tween-20. Streptavidin HRP (Pierce #21126, Rockland, Ill.) was diluted 1:20000 in PBS containing 0.1% BSA; 50 µL/well was added and the plates incubated for 1 hour at room temperature. Plates were washed 3 times with PBS containing 0.05% Tween-20. Fifty microliters of TMB solution (Sigma #T0440, St. Louis, Mo.) was added to each well and incubated for 10 minutes at room temperature. The reaction was stopped by addition of 1N sulphuric acid. Plates were read spectrophotmetrically at a wavelength of 450 nm.

Example 1.1.A.2

ELISA to Assess Ability of IL-12 p70 or IL-12 p40 to Compete with Binding of Anti Human IL-12 Antibodies to IL-12 p70

ELISA plates (Corning Costar, Acton, Mass.) were coated with 50 µL/well of 5 µg/ml goat anti-mouse IgG Fc specific (Pierce #31170, Rockford, Ill.) in PBS overnight at 4 degrees Celsius. Plates were washed once with PBS+0.05% Tween-20. Plates were blocked by addition of PBS+10% powdered milk for 1 hour at room temperature. Plates were washed three times after blocking with PBS+0.05% Tween-20.

Example 1.1.A 2(a)

IL-12 p70 Competition ELISA Protocol

Mouse sera or hybridoma supernatants were diluted in PBS containing 0.1% BSA (Sigma, St. Louis, Mo.) depending on anticipated antibody titer. Biotinylated recombinant purified human IL-12 p70 was prepared as a three times concentrated (3×) stock at 0.1 µg/ml in PBS containing 0.1% BSA. Recombinant purified human IL-12 p70 was prepared at various concentrations ranging from 0.1 to 10 µg/ml in PBS containing 0.1% BSA. Equal volumes (75 µL) of each of the following solutions were mixed: diluted mouse sera or hybridoma supernatant, biotinylated recombinant purified human IL-12 p70, and recombinant purified human IL-12 p70. Fifty microliters of this mixture was added to the coated ELISA plates described above and were incubated for 1 hour at room temperature. Wells were washed three times with PBS containing 0.05% Tween-20. Streptavidin HRP (Pierce #21126, Rockland, Ill.) was diluted 1:20000 in PBS containing 0.1% BSA; 50 µL/well was added and the plates incubated for 1 hour at room temperature. Plates were washed 3 times with PBS containing 0.05% Tween-20. Fifty microliters of TMB solution (Sigma #T0440, St. Louis, Mo.) was added to each well and incubated for 10 minutes at room temperature. The reaction was stopped by addition of 1N sulphuric acid. Plates were read spectrophotmetrically at a wavelength of 450 nm.

Example 1.1.A 2(b)

IL-12 p40 Competition ELISA Protocol

Mouse sera or hybridoma supernatants were diluted in PBS containing 0.1% BSA (Sigma, St. Louis, Mo.) depending on anticipated antibody titer. Biotinylated recombinant purified human IL-12 p70 was prepared as a three times concentrated (3×) stock at 0.1 µg/ml in PBS containing 0.1% BSA. Recombinant purified human IL-12 p40 was prepared at various concentrations ranging from 0.1 to 10 µg/ml in PBS containing 0.1% BSA. Equal volumes (75 µL) of each of the following solutions were mixed: diluted mouse sera or hybridoma supernatant, biotinylated recombinant purified human IL-12 p70, and recombinant purified human IL-12 p40. Fifty microliters of this mixture was added to the coated ELISA plates and incubated for 1 hour at room temperature. Wells were washed three times with PBS containing 0.05% Tween-20. Streptavidin HRP (Pierce #21126, Rockland, Ill.) was diluted 1:20000 in PBS containing 0.1% BSA; 50 µL/well was added and the plates incubated for 1 hour at room temperature. Plates were washed 3 times with PBS containing 0.05% Tween-20. Fifty microliters of TMB solution (Sigma #T0440, St. Louis, Mo.) was added to each well and incubated for 10 minutes at room temperature. The reaction was stopped by addition of 1N sulphuric acid. Plates were read spectrophotmetrically at a wavelength of 450 nm.

Example 1.1.B

Affinity Determinations Using Biacore Technology

The BIACORE assay (Biacore, Inc, Piscataway, N.J.) determines the affinity of antibodies with kinetic measurements of on-, off-rate constants. Binding of antibodies to recombinant purified human IL-12 p70 or recombinant purified human IL-12 p40 were determined by surface plasmon resonance-based measurements with a Biacore® 3000 instrument (Biacore® AB, Uppsala, Sweden) using running HBS-EP (10 mM HEPES [pH 7.4], 150 mM NaCl, 3 mM EDTA, and 0.005% surfactant P20) at 25° C. All chemicals were obtained from Biacore® AB (Uppsala, Sweden) or otherwise from a different source as described in the text. Approximately 5000 RU of goat anti-mouse IgG, (Fcγ), fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 µg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-mouse IgG in flow cell 1 and 3 was used as the reference surface. For kinetic analysis, rate equations derived from the 1:1 Langmuir binding model were fitted simultaneously to association and dissociation phases of all eight injections (using global fit analysis) with the use of Biaevaluation 4.0.1 software. Purified antibodies were diluted in HEPES-buffered saline for capture across goat anti-mouse IgG specific reaction surfaces. Mouse antibodies to be captured as a ligand (25 µg/ml) were injected over reaction matrices at a flow rate of 5 µl/min. The association and dissociation rate constants, $k_{on}$ (unit $M^{-1}s^{-1}$) and $k_{off}$ (unit $s^{-1}$) were determined under a continuous flow rate of 25 µl/min. Rate constants were derived by making kinetic binding measurements at ten different antigen concentrations ranging from 10-200 nM. The equilibrium dissociation constant (unit M) of the reaction between mouse antibodies and recombinant purified human IL-12 p70 or recombinant purified human IL-12 p40 was then calculated from the kinetic rate constants by the following formula: $K_D = k_{off}/k_{on}$. Binding is recorded as a function of time and kinetic rate constants are calculated. In this assay, on-rates as fast as $10^6 M^{-1} s^{-1}$ and off-rates as slow as $10^{-6} s^{-1}$ can be measured.

Example 1.1.C

Functional Activity of Anti Human IL-12 Antibodies

To examine the functional activity of the anti-human IL-12 antibodies of the invention, the antibodies were used in the following assays that measure the ability of an antibody to inhibit IL-12 activity.

Example 1.1.C 1

Preparation of Human PHA-Activated Lymphoblasts

Human peripheral blood mononuclear cells (PBMCs) were isolated from a leukopac collected from a healthy donor by Ficoll-Hypaque gradient centrifugation for 45 minutes at 1500 rpm as described in Current Protocols in Immunology, Unit 7.1. PBMC at the interface of the aqueous blood solution and the lymphocyte separation medium were collected and washed three times with phosphate-buffered saline (PBS) by centrifugation for 15 minutes at 1500 rpm to remove Ficoll-Paque particles.

The PBMC were then activated to form lymphoblasts as described in Current Protocols in Immunology, Unit 6.16. The washed PBMC were resuspended at 0.5-1×10⁶ cells/mL in RPMI complete medium (RPMI 1640 medium, 10% fetal bovine serum (FBS), 100 U/ml penicillin, 100 tg/ml streptomycin), supplemented with 0.01 mg/mL PHA-P (Sigma

L8754, St. Louis, Mo.) and cultured for 4 days at 37° C. in a 5% $CO_2$ atmosphere. After four days, cell cultures were then re-seeded at $1\times10^6$ cells/mL in culture media with 0.01 mg/mL PHA-P and 50 U/mL recombinant human IL-2 (R&D Systems #202-IL, Minneapolis, Minn.). Cells were incubated at 37° C. for 24 hours, washed with RPMI complete medium, then frozen in 95% FBS, 5% DMSO at $1\times10^7$ cells/ml.

Example 1.1.C 2

PHA Blast IFN-γ Induction Assay: Inhibition of Human IL-12 Activity

The ability of anti-human IL-12 antibodies to inhibit the human IL-12 induced production of IFN-γ by PHA blasts was analyzed as follows. Various concentrations of immunized mouse serum, murine hybridoma supernatant or purified anti-human IL-12 antibodies were preincubated for one hour at 37 degrees C. with 400 pg/ml recombinant purified human IL-12 p70 in 100 µL RPMI complete medium in a microtiter plate (U-bottom, 96-well, Costar). PHA blasts isolated as described above, were washed once and resuspended in RPMI complete medium to a cell density of $1\times10^7$ cells/ml. PHA blasts (100 µL of $1\times10^6$ cells/ml) were added to the antibody plus recombinant purified human IL-12 p70 mixture (final IL-12 p70 concentration was 200 pg/ml) and incubated for 18 hours at 37 deg C. After incubation, 150 µL of cell-free supernatant was withdrawn from each well and the level of human IFN-γ produced was measured using a human IFN-γ ELISA (R&D Systems Cat#DIF50).

Example 1.1.C3

PHA Blast IFN-γ Induction Assay: Inhibition of Cynomolgus Monkey (Cyno) IL-12 Activity The ability of anti-human IL-12 antibodies to inhibit the cynomolgus monkey IL-12 induced production of IFN-γ by PHA blasts was analyzed as follows. Various concentrations of immunized mouse serum, murine hybridoma supernatant or purified anti-human IL-12 antibodies were preincubated for one hour at 37 degrees C. with 150 pg/mL recombinant purified cyno IL-12 p70 in 100 µL RPMI complete medium in a microtiter plate (U-bottom, 96-well, Costar). PHA blasts isolated as described above, were washed once and resuspended in RPMI complete medium to a cell density of $1\times10^7$ cells/ml. PHA blasts (100 µL of $1\times10^7$ cells/mL) were added to the antibody plus recombinant purified cyno IL-12 p70 mixture (final cyno IL-12 p70 concentration was 75 µg/ml) and incubated for 18 hours at 37 deg C. After incubation, 150 µL of cell-free supernatant was withdrawn from each well and the level of human IFN-γ produced was measured using a human IFN-γ ELISA (R&D Systems Cat#DIF50).

Example 1.2

Generation of Anti Human IL-12 Monoclonal Antibodies

Anti human IL-12 mouse monoclonal antibodies were obtained as follows:

Example 1.2.A

Immunization of Mice with Human IL-12 Antigen

Twenty micrograms of recombinant purified human IL-12 p70 mixed with complete Freund's adjuvant (Rockland Immunochemicals, Gilbertsville, Pa.) was injected subcutaneously into five 6-8 week-old Balb/C and 5 AJ mice on Day 1. On days 24, 38, and 49, twenty micrograms of recombinant purified human IL-12 p70 mixed with Immunoeasy adjuvant (Qiagen, Valencia, Calif.) was injected subcutaneously into the same 5 Balb/C and 5 AJ mice. On day 84 or day 112 or day 144, mice were injected intravenously with 10 ug recombinant purified human IL-12 p70 or 2 ug recombinant purified human IL-12 p40 (R & D Systems, Minneapolis, Minn.).

Example 1.2.B

Generation of Hybridoma

Splenocytes obtained from the immunized mice described in Example 1.2.A were fused with SP2/O—Ag-14 cells at a ratio of 5:1 according to the established method described in Kohler, G. and Milstein 1975, Nature, 256:495 to generate hybridomas. Fusion products were plated in selection media containing azaserine and hypoxanthine in 96-well plates at a density of $2.5\times10^6$ spleen cells per well. Seven to ten days post fusion, macroscopic hybridoma colonies were observed. Supernatant from each well containing hybridoma colonies was tested by ELISA for the presence of antibody to IL-12 p70 (as described in Example 1.1.A.1). Supernatants testing positive for binding to IL-12 p70 were then tested to determine whether they were p40-specific by the IL-12 p70 or IL-12 p40 competition ELISA (as described in Example 1.1.A.2). Supernatants displaying IL-12 p40-specific activity were then tested for the ability to neutralize IL-12 in the PHA blast assay for IFN-γ (as described in Example 1.1.C).

TABLE 8

Fusion and screening data following immunizations of mice with human IL-12

| Mouse strain used in fusion | Number of wells plated | Number of wells with growth | Number of anti-IL-12 clones | Number of clones p40-specific | Number of p40 neutralizing clones | Number of clones subcloned |
| --- | --- | --- | --- | --- | --- | --- |
| A/J-2 | 750 | 450 | 50 | 14 | 6 | 4 |
| A/J-5 | 650 | 300 | 20 | | | |
| Balb/C-3 | 480 | 457 | 50 | 13 | 6 | 5 |
| Balb/C-4 | 768 | 649 | 25 | 17 | 13 | 4 |
| Total | 2648 | 1856 | 145 | 44 | 25 | 13 |

Example 1.2.C

Identification and Characterization of Anti Human IL-12p40 Monoclonal Antibodies Hybridomas producing antibodies that bound IL-12, generated according to Examples 1.2.B and 1.2.C, and capable of binding IL-12 p40 specifically and particularly those with $IC_{50}$ values in the PHA blast assay of 12 nM or less than 12 nM were scaled up and cloned by limiting dilution.

Hybridoma cells were expanded into media containing 10% low IgG fetal bovine serum (Hyclone #SH30151, Logan, Utah.). On average, 250 mL of each hybridoma supernatant (derived from a clonal population) was harvested, concentrated and purified by protein A affinity chromatography, as described in Harlow, E. and Lane, D. 1988 "Antibodies: A Laboratory Manual". The ability of purified mAbs to inhibit IL-12 activity was determined using the PHA blast assay as described in Examples 1.1.C2 and 1.1.C3. Table 9 shows $IC_{50}$ values from the PHA blast assays for ten monoclonal antibodies.

TABLE 9

Neutralization of IL-12 by anti IL-12p40 Murine Monoclonal Antibodies

| Murine Monoclonal Antibody | Average $IC_{50}$ (nM) Human IL-12 | Average $IC_{50}$ (nM) Cyno IL-12 |
|---|---|---|
| 1D4 | 0.031 | 0.078 |
| 1A6 | 0.052 | 0.044 |
| 1D8 | 0.31 | 1.4 |
| 3G7 | 0.15 | 0.35 |
| 5E8 | 12 | N/D |
| 8E1 | 0.19 | 0.18 |
| 1H6 | 0.69 | 1.6 |
| 3A11 | 3.4 | N/D |
| 4B4 | 0.039 | 0.028 |
| 7G3 | 0.047 | >20 |

The binding affinities of the monoclonal antibodies to recombinant purified human IL-12 p70 were determined using surface plasmon resonance (Biacore®) measurement as described in Example 1.1.B. Table 10 shows the affinity of the ten monoclonal antibodies described above for human IL-12 p70.

TABLE 10

Affinity of anti IL-12p40 Murine Monoclonal Antibodies for IL-12 p70

| Name | $k_{on}$ (1/M·s) | $k_{off}$ (1/s) | $K_D$ (nM) |
|---|---|---|---|
| 1D4 | $2.5 \times 10^5$ | $2.9 \times 10^{-5}$ | 0.12 |
| 1A6 | $1.5 \times 10^5$ | $3.5 \times 10^{-5}$ | 0.23 |
| 1D8 | $5.1 \times 10^5$ | $2.3 \times 10^{-5}$ | 0.044 |
| 3G7 | $8.2 \times 10^5$ | $3.8 \times 10^{-5}$ | 0.047 |
| 5E8 | $5.7 \times 10^5$ | $2.3 \times 10^{-3}$ | 4 |
| 8E1 | $6.9 \times 10^5$ | $5.1 \times 10^{-5}$ | 0.074 |
| 1H6 | $4.3 \times 10^5$ | $9.9 \times 10^{-5}$ | 0.25 |
| 3A11 | $1.5 \times 10^5$ | $1.9 \times 10^{-4}$ | 1.2 |
| 4B4 | $1.3 \times 10^5$ | $1.4 \times 10^{-5}$ | 0.1 |
| 7G3 | $1.1 \times 10^6$ | $2.8 \times 10^{-4}$ | 0.27 |

Example 1.2.C.1

Species Specificity of Murine Monoclonal Anti-Human IL-12p40 Antibodies

To determine whether the ten monoclonal antibodies described above recognize murine IL-12, two ELISAs were set up. First, a direct ELISA was set up by directly coating ELISA plates with 5 ug/ml of recombinant purified mouse IL-12 (Peprotech). Murine-anti-human IL-12 p40 mAbs were prepared at various concentrations ranging from 3 to 200 ng/ml in PBS containing 0.1% BSA (Sigma, St. Louis, Mo.). 50 μl of each antibody dilution was added to the coated ELISA plate and incubated for 1 hour at room temperature. Wells were washed 3 times with PBS containing 0.05% Tween-20. Anti-mouse IgG-HRP antibody (R&D #HAF007, Minneapolis, Minn.) was diluted 1:2000 in PBS containing 0.1% BSA; 50 ul/well was added and the plates incubated for 1 hour at room temperature. Fifty microliters of TMB solution (Sigma #T0440, St. Louis, Mo.) was added to each well and incubated for 10 minutes at room temperature. The reaction was stopped by addition of 2N sulphuric acid. Plates were read spectrophotmetrically at a wavelength of 450 nm.

Second, an indirect ELISA was set up by coating ELISA plates with 5 ug/ml of goat anti-mouse IgG, Fc fragment specific antibody (Pierce #31170, Rockland, Ill.). Murine anti-human IL-12 p40 mAbs were prepared at various concentrations ranging from 0.1 to 100 ng/ml in PBS containing 0.1% BSA; 50 ul of each antibody dilution was added to the coated ELISA plate and incubated for 1 hour at room temperature. Wells were washed 3 times with PBS containing 0.05% Tween-20. Recombinant purified mouse IL-12 (Preprotech) was diluted at 0.2 ug/ml in PBS containing 0.1% BSA; 50 ul/well was added and the plates incubated for 1 hour at room temperature. Wells were washed 3 times with PBS containing 0.05% Tween-20. Biotinylated anti-mouse IL-12 antibody (R&D #BAF419) was diluted at 0.2 ug/ml in PBS containing 0.1% BSA; 50 ul/well was added and the plates incubated for 1 hour at room temperature. Wells were washed 3 times with PBS containing 0.05% Tween-20. Streptavidin HRP (Pierce #21126, Rockland, Ill.) was diluted 1:20000 in PBS containing 0.1% BSA; 50 μL/well was added and the plates incubated for 1 hour at room temperature. Plates were washed 3 times with PBS containing 0.05% Tween-20. Fifty microliters of TMB solution was added to each well and incubated for 10 minutes at room temperature. The reaction was stopped by addition of 2N sulphuric acid. Plates were read spectrophotmetrically at a wavelength of 450 nm. Results from the direct and indirect ELISAs performed with the ten monoclonal antibodies are shown in Table 11.

TABLE 11

Binding of anti IL-12 Murine Monoclonal Antibodies to mouse IL-12 p40

| Name | Direct ELISA Binding of mAb to mu IL-12 | Indirect ELISA Binding of mAb to mu IL-12 |
|---|---|---|
| 1D4 | No | N/D |
| 1A6 | No | N/D |
| 1D8 | No | No |
| 3G7 | No | No |
| 5E8 | No | No |
| 8E1 | No | No |
| 1H6 | No | No |
| 3A11 | No | No |
| 4B4 | No | N/D |
| 7G3 | No | N/D |

Example 1.2.D

Determination of the Amino Acid Sequence of the Variable Region for Each Murine Anti-Human IL-12 p40 mAb For each amino acid sequence determination, approximately $10 \times 10^6$ hybridoma cells were isolated by centrifugation and processed to isolate total RNA with Trizol (Gibco BRL/Invitrogen, Carlsbad, Calif.) following manufacturer's instructions. Total RNA was subjected to first strand DNA synthesis using the SuperScript First-Strand Synthesis System (Invitrogen, Carlsbad, Calif.) per the manufacturers instructions. Oligo(dT) was used to prime first-strand synthesis to select for poly(A)+ RNA. The first-strand cDNA product was then amplified by PCR with primers designed for amplification of murine immunoglobulin variable regions (Ig-Primer Sets, Novagen, Madison, Wis.). PCR products were resolved on an agarose gel, excised, purified, and then subcloned with the TOPO Cloning kit into pCR2.1-TOPO vector (Invitrogen, Carlsbad, Calif.) and transformed into TOP10 chemically competent E. coli (Invitrogen, Carlsbad, Calif.). Colony PCR was performed on the transformants to identify clones containing insert. Plasmid DNA was isolated from clones containing insert using a QIAprep Miniprep kit (Qiagen, Valencia, Calif.). Inserts in the plasmids were sequenced on both strands to determine the variable heavy or variable light chain DNA sequences using M13 forward and M13 reverse primers (Fermentas Life Sciences, Hanover Md.). Variable heavy and variable light chain sequences of the ten monoclonal antibodies described in Example 1.2.0 are described in Table 1.

Example 2

Recombinant Anti Human IL-12p40 Antibodies

Example 2.1

Construction and Expression of Recombinant Chimeric Anti Human IL-12p40 Antibodies The DNA encoding the heavy chain constant region of murine anti-human IL-12p40 monoclonal antibodies 3G7, 8E1, 1A6, and 1D4 was replaced by a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al., 1991, *J. Immunol.*, 147:2657). The light chain constant region of each of these antibodies was replaced by a human kappa constant region. Full-length chimeric antibodies were transiently expressed in COS cells by co-transfection of chimeric heavy and light chain cDNAs ligated into the pBOS expression plasmid (Mizushima and Nagata, *Nucleic Acids Research* 1990, Vol 18, pg 5322) comprising a heavy chain signal sequence MEFGLSWLFLVAILKGVQC (SEQ ID NO. 110), and a light chain signal sequence MDMRVPAQLLGLLLLWFPGSRC ((SEQ ID NO. 111).

Cell supernatants containing recombinant chimeric antibody were purified by Protein A Sepharose chromatography and bound antibody was eluted by addition of acid buffer. Antibodies were neutralized and dialyzed into PBS.

The heavy chain cDNA encoding chimeric 3G7 (described above) was co-transfected with the 1D4 chimeric light chain cDNA (both ligated in the pBOS vector) into COS cells. Cell supernatant containing recombinant chimeric antibody was purified by Protein A Sepharose chromatography and bound antibody was eluted by addition of acid buffer. Antibodies were neutralized and dialyzed into PBS.

The purified chimeric anti-human IL-12 monoclonal antibodies were then tested for their ability to inhibit the IL-12 induced production of IFN-γ by PHA blasts as described in Examples 1.1.C2 and 1.1.C3. Table 12 shows $IC_{50}$ values from the PHA blast assays for five chimeric antibodies.

TABLE 12

| Neutralization of IL-12 by anti IL-12 Chimeric Antibodies | | |
|---|---|---|
| Name Of Chimeric | Average $IC_{50}$ (nM) Human IL-12 | Average $IC_{50}$ (nM) Cyno IL-12 |
| 1D4-Chim | 0.021 | 0.07 |
| 1A6-Chim | 0.021 | 0.02 |
| 3G7-Chim | 0.12 | 0.32 |
| 8E1-Chim | 0.17 | 0.15 |
| 3G7/1D4-Chim | 0.11 | 0.29 |

Example 2.2

Construction and Expression of CDR Grafted Anti Human IL-12p40 Antibodies

CDR-grafted anti-human IL-12 antibodies were generated as follows.

Example 2.2.1

Selection of Human Antibody Frameworks

Each murine variable heavy and variable light chain gene sequence (as described in Table 3) was separately aligned against 44 human immunoglobulin germline variable heavy chain or 46 germline variable light chain sequences (derived from NCBI Ig Blast website at http://www.ncbi.nlm.nih.gov/igblast/retrieveig.html.) using Vector NTI software. Human variable domain sequences having the highest overall homology to the original murine sequences (as well as the highest homology at positions known to be important for antigen binding) (Welschof, M. and Krauss, *J. Methods In Molecular Biology*, Vol 207) were selected for each heavy chain and light chain sequence to provide the framework (FW) 1, 2 and 3 sequences for CDR-grafting purposes. Identification of a suitable human variable heavy and light chain FW4 region (also known as the "joining" region) was accomplished by separately aligning each murine heavy chain and light chain FW4 region with 6 human immunoglobulin germline joining heavy chain and 5 germline joining light chain sequences in the NCBI database. In silico construction of complete CDR grafted antibodies was accomplished by substitution of human variable domain CDR sequences (derived from the NCBI website) with murine CDR sequences (derived from the hybridomas) with addition of a FW4 region (derived from the NCBI website) to each 3' end.

Example 2.2.2

Construction of CDR-Grafted Antibodies

In silico constructed CDR grafted antibodies described above were constructed de novo using oligonucleotides. For each variable region cDNA, 6 oligonucleotides of 60-80 nucleotides each were designed to overlap each other by 20 nucleotides at the 5' and/or 3' end of each oligonucleotide. In an annealing reaction, all 6 oligos were combined, boiled, and annealed in the presence of dNTPs. Then DNA polymerase I, Large (Klenow) fragment (New England Biolabs #M0210, Beverley, Mass.) was added to fill-in the approximately 40 bp gaps between the overlapping oligonucleotides. PCR was then performed to amplify the entire variable region gene using two outermost primers containing overhanging sequences complementary to the multiple cloning site in a modified pBOS vector (Mizushima, S. and Nagata, S., (1990) *Nucleic Acids Research* 18(17):5322).

The PCR products derived from each cDNA assembly were separated on an agarose gel and the band corresponding to the predicted variable region cDNA size was excised and purified. The variable heavy region was inserted in-frame onto a cDNA fragment encoding the human IgG1 constant region containing 2 hinge-region amino acid mutations (SEQ ID NO. 3) by homologous recombination in bacteria. These mutations are a leucine to alanine change at position 234 (EU numbering) and a leucine to alanine change at position 235 (Lund et al., 1991, *J. Immunol.*, 147:2657). The variable light chain region was inserted in-frame with the human kappa constant region (SEQ ID NO. 4) by homologous recombination. Bacterial colonies were isolated and plasmid DNA extracted; cDNA inserts were sequenced in their entirety. Correct CDR-grafted heavy and light chains corresponding to each antibody were co-transfected into COS cells to transiently produce full-length CDR-grafted anti-human IL-12 antibodies. For 1A6, pBOS vectors containing the 1A6 heavy chain grafted cDNA and the 1D4 light chain grafted cDNA were co-transfected into COS cells (the 1A6 light chain sequence, when grafted, was identical to the 1D4 light chain sequence). Cell supernatants containing recombinant chimeric antibody were purified by Protein A Sepharose chromatography and bound antibody was eluted by addition of acid buffer. Antibodies were neutralized and dialyzed into PBS. Nine CDR grafted antibodies are described in Table 5.

The ability of purified CDR grafted antibodies to inhibit IL-12 activity was determined using the PHA blast assay as described in Examples 1.1.C2 and 1.1.C3. The binding affinities of the purified CDR grafted antibodies to recombinant purified human IL-12p70 were determined using surface plasmon resonance (Biacore®) measurement as described in Example 1.1.B. Table 13 shows $IC_{50}$ values from the PHA blast assays and the affinity of the nine CDR grafted antibodies described in Table 7 for human IL-12p70 and cynomolgous IL-12p70.

TABLE 13

Neutralization of IL-12 by anti IL-12p40 CDR grafted Antibodies and Affinity of anti IL-12p40 CDR grafted Antibodies for human and cynomolgous IL-12p70 and

| | Anti IL-12p40 CDR grafted Antibody | | | | |
|---|---|---|---|---|---|
| | 1D4.1 | 1D4.2 | 1D4.3 | 1A6.1 | 1A6.2 |
| On-rate (1/M·s) | $2.6 \times 10^5$ | $1.6 \times 10^5$ | $2.1 \times 10^5$ | $1.1 \times 10^5$ | $1 \times 10^5$ |
| Off-rate (1/s) | $2.9 \times 10^{-5}$ | $2.6 10^{-4}$ | $5.3 \times 10^{-5}$ | $2.9 \times 10^{-5}$ | $5.4 \times 10^{-5}$ |
| $K_D$ (nM) | 0.12 | 1.7 | 0.25 | 0.27 | 0.54 |
| Av·$IC_{50}$ (nM) Hu IL-12 | 0.47 | 3 | 0.83 | 0.48 | 1.1 |
| Av·$IC_{50}$ (nM) Cyno IL-12 | 1.5 | 3 | 1.6 | 0.57 | 0.84 |

| | Anti IL-12p40 CDR grafted Antibody | | | | | |
|---|---|---|---|---|---|---|
| | 8E1.1 | 8E1.2 | 3G7.1 | 3G7.2 | 1A6.5 | 1A6.6 |
| On-rate (1/M·s) | $5.2 \times 10^5$ | 0 | $4.2 \times 10^5$ | $6.1 \times 10^5$ | $1.3 \times 10^5$ | $1.3 \times 10^5$ |
| Off-rate (1/s) | $8.7 \times 10^{-4}$ | 0 | $9.1 \times 10^{-5}$ | $1.4 \times 10^{-4}$ | $5.6 \times 10^{-5}$ | $1.0 \times 10^{-4}$ |
| $K_D$ (nM) | 1.7 | 0 | 0.22 | 0.23 | 0.43 | 0.078 |
| Av·$IC_{50}$ (nM) Hu IL-12 | 2.8 | 0 | 0.56 | 0.24 | 1.9 | 0.59 |
| Av·$IC_{50}$ (nM) Cyno IL-12 | 4.6 | 0 | 1.2 | 0.7 | 1.1 | 0.14 |

Example 2.3

Construction of Humanized Anti Human IL-12 Antibodies

Humanization of the anti human IL-12 antibodies was carried out as follows.

Example 2.3.1

Homology Modeling with CDR-Grafted Antibodies

Homology modeling was used was to identify residues unique to the murine antibody sequences that are predicted to be critical to the structure of the antibody combining site (the CDRs).

Homology modeling is a computational method whereby approximate three dimensional coordinates are generated for a protein. The source of initial coordinates and guidance for their further refinement is a second protein, the reference protein, for which the three dimensional coordinates are known and the sequence of which is related to the sequence of the first protein. The relationship among the sequences of the two proteins is used to generate a correspondence between the reference protein and the protein for which coordinates are desired, the target protein. The primary sequences of the reference and target proteins are aligned with coordinates of identical portions of the two proteins transferred directly from the reference protein to the target protein. Coordinates for mismatched portions of the two proteins, e.g., from residue mutations, insertions, or deletions, are constructed from generic structural templates and energy refined to insure consistency with the already transferred model coordinates. This computational protein structure may be further refined or employed directly in modeling studies. It should be clear from this description that the quality of the model structure is determined by the accuracy of the contention that the reference and target proteins are related and the precision with which the sequence alignment is constructed.

For the murine sequences 1A6, 8E1 and 1D4, a combination of BLAST searching and visual inspection was used to identify suitable reference structures. The reference structures chosen for 1A6 and 1D4 was the PDB entry 1JRH. For 8E1, the heavy chain reference structure was PDB entry 1FL3 and the light chain reference was 1MEX. Sequence identity of 25% between the reference and target amino acid sequences is considered the minimum necessary to attempt a homology modeling exercise. Sequence alignments were constructed manually and model coordinates were generated with the program Jackal (see Petrey et al. 2003, "Using multiple structure alignments, fast model building, and energetic analysis in fold recognition and homology modeling", *Proteins* 53 (Suppl. 6): 430-435).

The primary sequences of the murine and human framework regions of the selected antibodies share significant identity. Residue positions that differ are candidates for inclusion of the murine residue in the humanized sequence in order to retain the observed binding potency of the murine antibody. A list of framework residues that differ between the human and murine sequences was constructed manually.

The likelihood that a given framework residue would impact the binding properties of the antibody depends on its proximity to the CDR residues. Therefore, using the model structures, the residues that differ between the murine and human sequences were ranked according to their distance from any atom in the CDRs. Those residues that fell within 4.5 Å of any CDR atom were identified as most important and were recommended to be candidates for retention of the murine residue in the humanized antibody (i.e. back mutation).

Examination of the computer model suggested that in antibody 1A6.1, residues L1, L2, L36, and L67 of the light chain (1D4.1 VKB3) are in significant contact with the CDRs and therefore suggests that murine residues should be retained at these positions. In the case of 1D4.1, residues H1 and H98 of the heavy chain (1D4.1 VH2-70), as well as L2 and L67 of the light chain (1D4.1 VKB3) were identified as positions for back mutation.

Example 2.3.2

Generation of Hybrid Antibodies

To determine which CDR-grafted chain (VH, VL or both) may benefit from framework back-mutations, "hybrid" antibodies were constructed by pairing a CDR-grafted H or L chain with an appropriate chimeric murine H or L chain followed by co-transfection into COS cells. Table 14 shows the VH and VL amino acid sequences of the hybrid antibodies 1A6.3, 1A6.4, 1A6.7, 1A6.8, 1D4.4, and 1D4.5.

TABLE 14

Amino acid sequences of hybrid antibodies

| SEQ ID No. | Protein region | Sequence 12345678901234567890123456789 0 |
|---|---|---|
| 69 | VH 1A6.3 | |
| (10) | (VH2-26/JH6 FR1) | EVTLKESGPVLVKPTETLTLTCTVSGFSLS |
| (7) | (VH2-70/JH6 FR2) | TSGMGVSWIRQPPGKALEWLAHIWWDGDNY |
| (11) | (VH2-26/JH6 FR3) | YNPSLKSRLTISKDTSKSQVVLTMTNMDPV |
| (9) | (VH2-70/JH6 FR4) | DTATYYCARRTRVNYAMDYWGQGTTVTVSS |
| 38 | VL 1A6.3 | SVVMTQTPKFLLVSAGDRVTITCKASQSVS NDVAWFQQKPGQSPKLLIYYASNRYTGVPD RFTGSGYGTDFTFTISTVQAEDLAVYFCQQ DYNSPWTFGGGTKLEIKR |
| 37 | VH 1A6.4 | QVTLKESGPGILKPSQTLSLTCSFSGFSLS TSGMGVSWIRQPSGKGLEWLAHIWWDGDNY YNPSLKSQLTISKDTSRNQVFLRIATVDTA DTATYYCARRTRVNYAMDYWGQGTSVTVSS |
| 70 | VL 1A6.4 | |
| (27) | (L2/JK4 FR1) | EIVMTQSPATLSVSPGERATLSCKASQSVS |
| (28) | (L2/JK4 FR2) | NDVAWYQQKPGQAPRLLIYYASNRYTGIPA |
| (29) | (L2/JK4 FR3) | RFSGSGSGTEFTLTISSLQSEDFAVYYCQQ |
| (26) | (B3/JK4 FR4) | DYNSPWTFGGGTKVEIKR |
| 37 | VH 1A6.7 | QVTLKESGPGILKPSQTLSLTCSFSGFSLS TSGMGVSWIRQPSGKGLEWLAHIWWDGDNY YNPSLKSQLTISKDTSRNQVFLRIATVDTA DTATYYCARRTRVNYAMDYWGQGTSVTVSS |
| 68 | VL 1A6.7 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYNSPWTFGGGTKVEIKR |
| 67 | VH 1A6.8 | |
| (6) | (VH2-70/JH6 FR1) | EVTLRESGPALVKPTQTLTLTCTFSGFSLS |
| (7) | (VH2-70/JH6 FR2) | TSGMGVSWIRQPPGKALEWLAHIWWDGDNY |
| (8) | (VH2-70/JH6 FR3) | YNPSLKSRLTISKDTSKNQVVLTMTNMDPV |
| (9) | (VH2-70/JH6 FR4) | DTATYYCARRTRVNYAMDYWGQGTTVTVSS |
| 38 | VL 1A6.8 | SVVMTQTPKFLLVSAGDRVTITCKASQSVS NDVAWFQQKPGQSPKLLIYYASNRYTGVPD RFTGSGYGTDFTFTISTVQAEDLAVYFCQQ DYNSPWTFGGGTKLEIKR |
| 65 | VH 1D4.4 | |
| (6) | (VH2-70/JH6 FR1) | EVTLRESGPALVKPTQTLTLTCTFSGFSLS |
| (7) | (VH2-70/JH6 FR2) | KSVMGVSWIRQPPGKALEWLAHIYWDDDKY |
| (8) | (VH2-70/JH6 FR3) | YNPSLKSRLTISKDTSKNQVVLTMTNMDPV |
| (9) | (VH2-70/JH6 FR4) | DTATYYCARRGIRSAMDYWGQGTTVTVSS |
| 36 | VL 1D4.4 | SVVMTQTPKFLLVSAGDRVTITCKASQSVS NDVAWYQQKPGQSPKLLIYYASNRYTGVPD RFTGSGYGTDFTFIISTVRAEDLAVYFCQQ DYNSPWTFGGGTKLEIKR |
| 35 | VH 1D4.5 | QVTLKESGPGILQPSQTLSLTCSFSGFSLR KSVMGVSWIRQPSGKGLEWLAHIYWDDDKY YNPSLKSRLTISKDPSRNQVFLKITSVDTA DAATYYCTRRGIRSAMDYWGQGTSVTVSS |
| 62 | VL 1D4.5 | |
| (23) | (B3/JK4 FR1) | DIVMTQSPDSLAVSLGERATINCKASQSVS |
| (24) | (B3/JK4 FR2) | NDVAWYQQKPGQPPKLLIYYASNRYTGVPD |
| (25) | (B3/JK4 FR3) | RFSGSGSGTDFTLTISSLQAEDVAVYYCQQ |
| (26) | (B3/JK4 FR4) | DYNSPWTFGGGTKVEIKR |

Hybrid antibodies were purified by protein A affinity chromatography (Example 1.2.C) and tested for potency in the PHA blast assay as in Examples 1.1.C2 and 1.1.C3. Kinetic measurements were determined using BIAcore as in Example 1.1.B. Table 15 shows the $K_D$ and $IC_{50}$ values of the hybrid antibodies. The potency and affinity data derived with the hybrid mAbs was compared to data generated with the appropriate CDR-grafted mAbs (Example 2.3.1) to identify changes in potency and affinity attributed to a particular VH or VL chain. Whether or not, a humanized VH or VL chain was the optimum chain, was assessed using the methods described in Example 2.3.1. In some cases residues that did not fall within 4.5 A° of any CDR atom were additionally targeted for back mutations.

TABLE 15

Neutralization of IL-12 by anti-IL-12p40 hybrid antibodies and affinity of anti-IL-12p40 hybrid antibodies

| Antibody | 1D4.4 | 1D4.5 | 1A6.3 | 1A6.4 | 1A6.7 | 1A6.8 |
|---|---|---|---|---|---|---|
| On-rate (1/M·s) | $2.8 \times 10^5$ | $3 \times 10^5$ | $1.9 \times 10^5$ | $1.1 \times 10^5$ | ND | ND |
| Off-rate (1/s) | $2.1 \times 10^{-5}$ | $3.1 \times 10^{-5}$ | $2.6 \times 10^{-5}$ | $1.1 \times 10^{-4}$ | ND | ND |
| KD (nM) | 0.074 | 0.11 | 0.14 | 1.0 | ND | ND |
| Av·$IC_{50}$(nM) huIL-12 | 0.64 | 0.053 | 0.068 | 2.1 | 0.29 | 0.08 |
| Av·$IC_{50}$(nM) cyno IL-12 | 1.1 | 0.11 | 0.049 | 1.2 | 0.35 | 0.06 |

Example 2.3.3

Construction of Framework Back Mutations in CDR-Grafted Antibodies

To generate humanized antibodies framework back mutations were introduced into the CDR-grafted antibodies using mutagenic primers and the QuikChange Multi Site-Directed Mutagenesis kit (Stratagene #200513, La Jolla, Calif.) following manufacturers instructions. Different combinations of back mutations were constructed for each of the CDR-grafts to identify the relative importance of each residue. 1A6.1 light chain VKB3 variant 1 (L1-D→S, L2-I→V, L36-Y→F, L67-S→Y), 1D4.1 VKB3 variant 2 (L1-D→S, L36-Y→F, L67-S→Y), 1D4.1 VKB3 variant 3 (L1-D→S, L67-S→Y), 1D4.1 VKB3 variant 4 (L2-I→V, L67-S→Y), and 1D4.1 VKB3 variant 5 (L67-S→Y). 1D4.1 heavy chain VH2-70 variant 1 (H1-E→Q, H93-A→T), and 1D4.1 VH2-70 variant 2 (H93-A→T). Mutated single stranded DNA was then transformed into XL10-Gold ultracompetent cells. Colony sequencing was performed on the transformants to identify clones bearing the desired mutations. Plasmid DNA was isolated from positive clones using a Qiagen Maxiprep kit (Qiagen, Valencia, Calif.) and the variable and constant regions were sequenced in their entirety.

As described above several additional combinations of back mutations were constructed for each of the CDR grafted antibodies. Characterization of the humanized antibodies generated, as disclosed above, was carried out as disclosed below in Example 2.3.4.

Example 2.3.4

Expression and Characterization of Humanized Antibodies

PBOS expression vectors (see Example 2.1 and 2.2.2) harboring heavy and light chains containing framework back mutations were co-transfected into COS cells to transiently produce full-length humanized antibodies. The amino acid sequences of the VH and VL regions of the humanized antibodies are disclosed in Table 16.

TABLE 16

Sequences of Humanized Antibodies

| SEQ ID No. | Protein region | Sequence 12345678901234567890123456 7890 |
|---|---|---|
| 67 | VH 1A6.9 | |
| (6) | (VH2-70/JH6 FR1) | EVTLRESGPALVKPTQTLTLTCTFSGFSLS |
| (7) | (VH2-70/JH6 FR2) | TSGMGVSWIRQPPGKALEWLAHIWWDGDNY |
| (8) | (VH2-70/JH6 FR3) | YNPSLKSRLTISKDTSKNQVVLTMTNMDPV |
| (9) | (VH2-70/JH6 FR4) | DTATYYCARRTRVNYAMDYWGQGTTVTVSS |
| 79 | VL 1A6.9 | SVVMTQSPDSLAVSLGERATTNCKASQSVS NDVAWFQQKPGQPPKLLIYYASNRYTGVPD RFSGSGYGTDFTLTISSLQAEDVAVYYCQQ DYNSPWTFGGGTKVEIKR |
| 80 | VH 1D4.6 | EVTLRESGPALVKPTQTLTLTCTFSGFSLS KSVMGVSWIRQPPGKALEWLAHIYWDDDKY YNPSLKSRLTISKDTSKNQVVLTMTNMDPV DTATYYCTRRGIRSAMDYWGQGTTVTVSS |
| 81 | VL 1D4.6 | DVVMTQSPDSLAVSLGERATINCKASQSVS NDVAWYQQKPGQPPKLLIYYASNRYTGVPD RFSGSGYGTDFTLTISSLQAEDVAVYYCQQ DYNSPWTFGGGTKVEIKR |
| 82 | VH 1D4.7 | EVTLRESGPALVKPTQTLTLTCTFSGFSLR KSVMGVSWIRQPPGKALEWLAHIYWDDDKY YNPSLKSRLTISKDTSKNQVVLTMTNMDPV DTATYYCTRRGIRSAMDYWGQGTTVTVSS |

TABLE 16-continued

Sequences of Humanized Antibodies

| SEQ ID No. | Protein region | Sequence 123456789012345678901234567890 |
|---|---|---|
| 83 | VL 1D4.7 | DVVMTQSPDSLAVSLGERATINCKASQSVS NDVAWYQQKPGQPPKLLIYYASNRYTGVPD RFSGSGYGTDFTLTISSLQAEDVAVYYCQQ DYNSPWTFGGGTKVEIKR |
| 84 | VH 1D4.8 | EVTLRESGPALVKPTQTLTLTCTFSGFSLR KSVMGVSWIRQPPGKALEWLAHIYWDDDKY YNPSLKSRLTISKDTSKNQVVLTMTNMDPV DTATYYCTRRGIRSAMDYWGQGTTVTSS |
| 85 | VL 1D4.8 | DIVMTQSPDSLAVSLGERATINCKASQSVS NDVAWYQQKPGQPPKLLIYYASNRYTGVPD RFSGSGSGTDFTLTISSLQAEDVAVYYCQQ DYNSPWTFGGGTKVEIKR |
| 86 | VH 1D4.9 | EVTLRESGPALVKPTQTLTLTCTFSGFSLR KSVMGVSWIRQPPGKALEWLAHIYWDDDKY YNPSLKSRLTISKDTSKNQVVLTMTNMDPV DTATYYCTRRGIRSAMDYWGQGTTVTSS |
| 87 | VL 1D4.9 | DIVMTQSPDSLAVSLGERATINCKASQSVS NDVAWYQQKPGQPPKLLIYYASNRYTGVPD RFSGSGYGTDFTLTISSLQAEDVAVYYCQQ DYNSPWTFGGGTKVEIKR |
| 88 | VH 8E1.3 | EVKLVESGGGLVQPGGSLRLSCAASGFTFS DYGMVWVRQAPGKGLEWVASISSGSSNIYY ADTVKGRFTISRDDSKNTLYLQMNSLKTED TAVYYCARNPYWGQGTTVTSS |
| 89 | VL 8E1.3 | DIVMTQSPSSLSASVGDRVTITCKASQNVG TNVAWYQQKPEKAPKSLIYSASHRYSGVPS RFSGSGSGTDFTLTISSLQPEDFATYYCQQ YNSYPLTFGGGTKVEIKR |
| 90 | VH 3G7.3 | EVQLVQSGAEVKKPGASVKVSCKATGYTFN DYWIEWVRQAPGQGLEWMGGFSHGSGSTNY NEKFKGRVTMTADSSTNTAYMELRSLRSDD TAVYYCARRRFRGMDYWGQGTTVTSS |
| 91 | VL 3G7.3 | EIVMTQSPATLSVSPGERATLSCKASQSVS NDVAWYQQKPGQAPRLLIYYASNRYTGVPD RFSGSGSGTEFTLTISSLQSEDFAVYYCQQ DYSSPWSFGGGTKVEIKR |

The amino acid positions back mutated in the VH and VL of the CDR-grafted antibodies are listed in Table 17.

TABLE 17

Back mutated amino acids present in humanized antibodies

| Antibody Name | Mutations in VH | Mutations in VK |
|---|---|---|
| 1A6.9 | None | L1 D -> S<br>L2 I -> V<br>L36 Y -> F<br>L67 S -> Y |
| 1D4.6 | H93 A -> T | L2 I -> V<br>L67 S -> Y |
| 1D4.7 | H30 S -> R<br>H93 A -> T | L2 I -> V<br>L67 S -> Y |
| 1D4.8 | H30 S -> R<br>H93 A -> T | None |
| 1D4.9 | H30 S -> R<br>H93 A -> T | L67 S -> Y |
| 8E1.3 | H3 Q -> K<br>H49 G -> A<br>H77 S -> T | L3 Q -> V |
| 3G7.3 | H25 S -> T<br>H30 T -> N<br>H71 T -> A<br>H73 T -> S<br>H76 S -> N | L58 I -> V<br>L60 A -> D |

Cell supernatants containing humanized antibodies were purified as described in Example 1.2.C. The ability of the purified humanized antibodies to neutralize IL-12 in vitro was determined using the PHA blast assay as described in Examples 1.1.C2 and 1.1.C3. The binding affinities of the purified antibodies to recombinant purified human IL-12p70 were determined using BIAcore as described in Example 1.1.B. Table 18 shows the $IC_{50}$ values from the PHA blast assay and the $K_D$s from BIAcore.

TABLE 18

Neutralization of IL-12 by anti-IL-12p40 humanized antibodies and affinity of anti-IL-12p40 humanized antibodies

| Antibody | 1D4.6 | 1D4.7 | 1D4.8 | 1D4.9 | 1A6.9 | 8E1.3 | 3G7.3 |
|---|---|---|---|---|---|---|---|
| On-rate (1/M·s) | $4.8 \times 10^5$ | $>1 \times 10^5$ | $1.2 \times 10^5$ | $5.3 \times 10^5$ | $3.5 \times 10^5$ | $1.3 \times 10^6$ | $7.8 \times 10^5$ |
| Off-rate (1/s) | $<1 \times 10^{-5}$ | $<1 \times 10^{-5}$ | $<1 \times 10^{-5}$ | $1 \times 10^{-6}$ | $<1 \times 10^{-5}$ | $1.0 \times 10^{-3}$ | $1.5 \times 10^{-4}$ |
| KD (nM) | <0.01 | <0.01 | <0.01 | <0.01 | <0.01 | 0.76 | 0.2 |
| Av · $IC_{50}$ (nM) huIL-12 | 0.15 | 0.014 | 0.095 | 0.035 | 0.15 | 10 | 0.42 |
| Av · $IC_{50}$ (nM) cyno IL-12 | ND | 0.031 | ND | ND | ND | ND | ND |

Example 2.4

Generation of Additional Humanized Anti Human IL-12 Antibodies

Humanization of the variable regions of the murine monoclonal antibodies 8E1 and 1A6 were carried out essentially according to the procedure of Queen, C., et al., *Proc. Natl. Acad. Sci. USA* 86: 10029-10033 (1989). First, human V segments with high homology to the murine monoclonal antibody VH or VL amino acid sequences were identified. Next, the complementarity-determining region (CDR) sequences together with framework amino acids important for maintaining the structures of the CDRs were grafted into the selected human framework sequences. In addition, human framework amino acids that were found to be rare in the corresponding V region subgroup were substituted with consensus amino acids to reduce potential immunogenicity. The resulting humanized monoclonal antibodies were expressed in cells, purified and characterized as described below.

Humanized monoclonal antibodies 8E1.4, 8E1.5, 8E1.6, 1A6.10, 1A6.11, and 1A6.12 were generated as follows.

Example 2.4.1

Generation of Humanized Monoclonal Antibodies 8E1.4, 8E1.5, 8E1.6

For humanization of the 8E1 variable regions, human V region frameworks used as acceptors for the CDRs of 8E1 were chosen based on sequence homology. First, a molecular model of the 8E1 variable regions was constructed with the aid of the computer programs ABMOD and ENCAD (Levitt, M., *J. Mol. Biol.* 168: 595-620 (1983)). Next, based on a homology search against human V and J segment sequences, the VH segment HA3D1 (Olee, T., et al., *J. Exp. Med.* 175: 831-842 (1992)) and the J segment JH4 (Ravetch, J. V., et al., *Cell* 27: 583-591 (1981)) were selected to provide the frameworks for the 8E1.4, 8E1.5, and 8E1.6 heavy chain variable regions. For the 8E1.4, 8E1.5 and 8E1.6 light chain variable regions, the VL segment HK137 (Bentley, D. L., and Rabbitts, T. H., *Cell* 32: 181-189 (1983)) and the J segment JK2 (Hieter, P. A., et al., *J. Biol. Chem.* 257: 1516-1522 (1982)) were used. The identity of the framework amino acids between 8E1 VH and the acceptor human HA3D1 and JH4 segments was 84%, while the identity between 8E1 VL and the acceptor human HK137 and JK4 segments was 67%. Human antibody heavy chain and light chain acceptor sequences used to generate additional humanized anti-human IL-12 antibodies are listed in Table 19 and 20.

TABLE 19

Heavy Chain Acceptor Sequences used for Additional Humanized Antibodies

| SEQ ID No. | Protein region | Sequence 123456789012345678901234567890 |
|---|---|---|
| 92 | M60/JH4 FR1 | QVTLRESGPALVKPTQTLTLTCTLYGFSLS |
| 7 | M60/JH4 FR2 | WIRQPPGKALEWLA |
| 8 | M60/JH4 FR3 | RLTISKDTSKNQVVLTMTNMDPVDTATYYCAR |
| 93 | M60/JH4 FR4 | WGQGTLVTVSS |

TABLE 19-continued

Heavy Chain Acceptor Sequences used for Additional Humanized Antibodies

| SEQ ID No. | Protein region | Sequence 123456789012345678901234567890 |
|---|---|---|
| 94 | HA3D1/JH4 FR1 | EVQLVESGGGLVQPGGSLRLSCAASGFTFS |
| 16 | HA3D1/JH4 FR2 | WVRQAPGKGLEWVS |
| 17 | HA3D1/JH4 FR3 | RFTISRDNAKNSLYLQMNSLRAEDTAVYYCAR |
| 95 | HA3D1/JH4 FR4 | WGQGTLVTVSS |

TABLE 20

Light Chain Acceptor used for Additional Humanized Antibodies

| SEQ ID No. | Protein region | Sequence 123456789012345678901234567890 |
|---|---|---|
| 30 | III-3R/JK4 FR1 | DIQMTQSPSSLSASVGDRVTITC |
| 34 | III-3R/JK4 FR2 | WYQQKPGKAPKLLIY |
| 96 | III-3R/JK4 FR3 | GVPSRISGSGSGTDFTFTISSLQPEDIATYYC |
| 26 | III-3R/JK4 FR4 | FGGGTKVEIKR |
| 30 | HK137/JK4 FR1 | DIQMTQSPSSLSASVGDRVTITC |
| 97 | HK137/JK4 FR2 | WFQQKPGKAPKSLIY |
| 32 | HK137/JK4 FR3 | GVPSRFSGSGSGTDFTLTISSLQPEDFATYYC |
| 26 | HK137/JK4 FR4 | FGGGTKVEIKR |

Example 2.4.2

Construction of 8E1.4, 8E1.5 and 8E1.6 Antibodies

The heavy and light chain variable region genes were constructed and amplified using approximately 30 overlapping synthetic oligonucleotides ranging in length from approximately 20 to 40 bases following a published method (Rouillard, J.-M., et al., *Nucleic Acids Res.* 32: W176-W180 (2004)). The oligonucleotides were annealed and assembled with the Expand High Fidelity PCR System (Roche Diagnostics Corporation, Indianapolis, Ind.), yielding a full-length product. The resulting product was amplified by the polymerase chain reaction (PCR) using the Expand High Fidelity PCR System. The PCR-amplified fragments were gel-purified, digested with MluI and XbaI, gel-purified, and subcloned, respectively, into a modified form of pVg1.D.Tt (Cole, M. S., et al., *J. Immunol.* 159: 3613-3621 (1997); and see below) and pVk (Co, M. S., et al., *J. Immunol.* 148: 1149-1154 (1992)).

At framework positions in which the computer model suggested significant contact with the CDRs, the amino acids from the mouse V regions were substituted for the original human framework amino acids. This was done at residue 49 for 8E1.4 and 8E1.5 heavy chains, and additionally at residue 74 for the heavy chain of 8E1.6. For the light chains of 8E1.5 and 8E1.6, replacements were made at residue 46, and additionally at residue 60 for 8E1.5. Framework residues that occurred only rarely at their respective positions in the corresponding human V region subgroups were replaced with human consensus amino acids at those positions. This was done at residue 78 for both 8E1.5 and 8E1.6 heavy chains, and at residue 36 for the 8E1.5 and 8E1.6 light chains.

Site-directed mutagenesis of the synthetic V-genes was done using the QuikChange II Site-Directed Mutagenesis Kit (Stratagene, La Jolla, Calif.), following the manufacturer's recommendations. Specific mutations in the 8E1.6 VH gene were created using mutagenesis oligos and PCR methods well known in the art. The PCR step was done using PfuUltra HF DNA Polymerase (Stratagene), following the manufacturer's recommendations, by incubating at 95° C. for 30 sec, followed by 18 cycles of 95° C. for 30 sec, 55° C. for 1 min and 68° C. for 1 min, followed by incubating at 68° C. for 7 min. Following digestion with DpnI, E. coli strain TOP10 Chemically Competent Cells (Invitrogen Corporation, Carlsbad, Calif.) were transformed with a small portion of the PCR product. Sequence verified miniprep DNA was digested with MluI and XbaI, and the resulting restriction fragment containing the mutated 8E1.6 VH gene was subcloned into the modified pVg1.D.Tt expression vector described below.

Similarly, specific mutations in the 8E1.5 VL gene were created using mutagenesis oligos and PCR methods well known in the art. The PCR step was done as described above, and following digestion with MluI and XbaI, the resulting restriction fragment was subcloned into the pVk expression vector. Mutations were verified by nucleotide sequencing.

Genes encoding humanized VH or VL were designed as mini-exons including signal peptides, splice donor signals, and appropriate restriction enzyme sites for subsequent cloning into a mammalian expression vector. The splice donor signals in the VH and VL mini-exons were derived from the corresponding human germline JH and JK sequences, respectively. The signal peptide sequences in the humanized VH mini exon was MEFGLSWLFLVAILKGVQC (SEQ ID NO. 110), and in the humanized VL mini-exons was MDMRV-PAQLLGLLLLWFPGSRC(SEQ ID NO. 111). The 8E1.4, 8E1.5 and 8E1.6 VH and VL genes were constructed by assembly of overlapping synthetic oligonucleotides and PCR methods well known in the art.

Example 2.4.3

Generation of Humanized Monoclonal Antibodies 1A6.10, 1A6.11 and 1A6.12

For humanization of the 1A6.10, 1A6.11 and 1A6.12 variable regions, the general approach provided in the present invention was followed. First, a molecular model of the 1A6 variable regions was constructed with the aid of the computer programs ABMOD and ENCAD (Levitt, M., J. Mol. Biol. 168: 595-620 (1983)). Next, based on a homology search against human V and J segment sequences, the VH segment M60 (Schroeder, Jr., H. W. and Wang, J. Y., Proc. Natl. Acad. Sci. USA 87: 6146-6150 (1990)) and the J segment JH4 (Ravetch, J. V., et al., Cell 27: 583-591 (1981)) were selected to provide the frameworks for the 1A6.10 and 1A6.12 heavy chain variable regions. For the 1A6.10, 1A6.11 and 1A6.12 light chain variable regions, the VL segment III-3R (Manheimer-Lory, A., et al., J. Exp. Med. 174: 1639-1652 (1991)) and the J segment JK4 (Hieter, P. A., et al., J. Biol. Chem. 257: 1516-1522 (1982)) were used. The identity of the framework amino acids between 1A6 VH and the acceptor human M60 and JH4 segments was 74%, while the identity between 1A6 VL and the acceptor human III-3R and JK4 segments was 71%. The antibody sequences were generated as disclosed in Example 2.3.3.

At framework positions in which the computer model suggested significant contact with the CDRs, the amino acids from the mouse V regions were substituted for the original human framework amino acids. This was done at residue 68 for the 1A6.10, 1A6.11 and 1A6.12 heavy chains. For the light chains, replacements were made at residues 36 and 67 for 1A6.11 and 1A6.12, and additionally at residue 60 for 1A6.12. Framework residues that occurred only rarely at their respective positions in the corresponding human V region subgroups were replaced with human consensus amino acids at those positions. This was done at residues 10, 46, 83, 84, 86 and 87 of the heavy chain, and at residue 62 of the light chains of 1A6.10, 1A6.11 and 1A6.12. Site directed mutagenesis was performed using mutagenic oligos and PCR method as described above.

The amino acid sequences of the resulting VH and VL regions of the additional humanized anti-IL-12 antibodies generated are listed in Table 21.

TABLE 21

Sequences of Additional Humanized Antibodies

| SEQ ID No. | Protein region | Sequence 12345678901234567890123456789 0 |
|---|---|---|
| 98 | VH 1A6.10 | EVTLRESGPGLVKPTQTLTLTCTLYGFSLS TSGMGVSWIRQPPGKGLEWLAHIWWDGDNY YNPSLKSQLTISKDTSKNQVVLKLTSVDPV DTATYYCARRTRVNYAMDYWGQGTLVTVSS |
| 99 | VL 1A6.10 | DIQMTQSPSSLSASVGDRVTITCKASQSVS NDVAWYQQKPGKAPKLLIYYASNRYTGVPD RFSGSGYGTDFTFTISSLQPEDIATYYCQQ DYNSPWTFGGGTKVEIKR |
| 100 | VH 1A6.11 | EVTLRESGPGLVKPTQTLTLTCTLYGFSLS TSGMGVSWIRQPPGKGLEWLAHIWWDGDNY YNPSLKSQLTISKDTSKNQVVLKLTSVDPV DTATYYCARRTRVNYAMDYWGQGTLVTVSS |
| 101 | VL 1A6.11 | DIQMTQSPSSLSASVGDRVTITCKASQSVS NDVAWYQQKPGKAPKLLIYYASNRYTGVPS RFSGSGYGTDFTFTISSLQPEDIATYYCQQ DYNSPWTFGGGTKVEIKR |
| 102 | VH 1A6.12 | EVTLRESGPGLVKPTQTLTLTCTLYGFSLS TSGMGVSWIRQPPGKGLEWLAHIWWDGDNY YNPSLKSQLTISKDTSKNQVVLKLTSVDPV DTATYYCARRTRVNYAMDYWGQGTLVTVSS |
| 103 | VL 1A6.12 | DIQMTQSPSSLSASVGDRVTITCKASQSVS NDVAWFQQKPGKAPKLLIYYASNRYTGVPD RFSGSGYGTDFTFTISSLQPEDIATYYCQQ DYNSPWTFGGGTKVEIKR |
| 104 | VH 8E1.4 | EVQLVESGGGLVQPGGSLRLSCAASGFTFS DYGMV WVRQAPGKGLEWVASISSGSSNIYY ADTVKGRFTISRDNAKNTLYLQMNSLRAED TAVYYCARNPYWGQGTLVTVSS |
| 105 | VL 8E1.4 | DIQMTQSPSSLSASVGDRVTITCKASQNVG TNVAWYQQKPGKAPKGLIYSASHRYSGVPS RFSGSGSGTDFTLTISSLQPEDFATYYCQQ YNSYPLTFGGGTKVEIKR |
| 106 | VH 8E1.5 | EVQLVESGGGLVQPGGSLRLSCAASGFTFS DYGMV WVRQAPGKGLEWVASISSGSSNIYY ADTVKGRFTISRDNAKNTLYLQMNSLRAED TAVYYCARNPYWGQGTLVTVSS |
| 107 | VL 8E1.5 | DIQMTQSPSSLSASVGDRVTITCKASQNVG TNVAWYQQKPGKAPKGLIYSASHRYSGVPD |

| | |
|---|---|
| | RFSGSGSGTDFTLTISSLQPEDFATYYCQQ<br>YNSYPLTFGGGTKVEIKR |
| 108VH 8E1.6 | EVQLVESGGGLVQPGGSLRLSCAASGFTFS<br>DYGMVWVRQAPGKGLEWVASISSGSSNIYY<br>ADTVKGRFTISRDDAKNTLYLQMNSLRAED<br>TAVYYCARNPYWGQGTLVTVSS |
| 109VL 8E1.6 | DIQMTQSPSSLSASVGDRVTITCKASQNVG<br>TNVAWYQQKPGKAPKGLIYSASHRYSGVPS<br>RFSGSGSGTDFTLTISSLQPEDFATYYCQQ<br>YNSYPLTFGGGTKVEIKR |

The amino acid positions in the framework that were mutated are listed in Table 22.

TABLE 22

Positions of Framework Mutations in Additional Humanized Antibodies

| Antibody Name | Mutations in VH | Mutations in VK |
|---|---|---|
| 1A6.10 | H10 A -> G<br>H46 A -> G<br>H68 R -> Q<br>H83 T -> K<br>H84 M -> L<br>H86 N -> S<br>H87 M -> V | L62 I -> F<br>L67 S -> Y |
| 1A6.11 | H10 A -> G<br>H46 A -> G<br>H68 R -> Q<br>H83 T -> K<br>H84 M -> L<br>H86 N -> S<br>H87 M -> V | L36 Y -> F<br>L62 I -> F<br>L67 S -> Y |
| 1A6.12 | H10 A -> G<br>H46 A -> G<br>H68 R -> Q<br>H83 T -> K<br>H84 M -> L<br>H86 N -> S<br>H87 M -> V | L36 Y -> F<br>L60 S -> D<br>L62 I -> F<br>L67 S -> Y |
| 8E1.4 | H49 S -> A<br>H78 S -> T | L36 F -> Y<br>L46 S -> G |
| 8E1.5 | H49 S -> A<br>H78 S -> T | L36 F -> Y<br>L46 S -> G<br>L60 S -> D |
| 8E1.6 | H49 S -> A<br>H74 N -> D<br>H78 S -> T | L36 F -> Y<br>L46 S -> G |

Example 2.4.4

Expression of Additional Humanized Antibodies

The allotype of the human gamma-1 constant region gene in the expression plasmid pVg1.D.Tt was modified from G1m (z,a) to the z, non-a allotype. The overlap-extension PCR method (Higuchi, R., in "PCR Technology: Principles and Applications for DNA Amplification", Stockton Press, New York (1989), pp. 61-70) was used to generate the amino acid substitutions D356E and L358M (numbered according to the EU index of Kabat, E. A., et al., "Sequences of Proteins of Immunological Interest", 5th ed., National Institutes of Health, Bethesda, Md. (1991)), using mutagenesis primers. The PCR step was done using the QuikChange II Site-Directed Mutagenesis Kit (Stratagene). Following digestion or PCR generated product with SfiI and EagI, the resulting restriction fragment was subcloned into a modified form of the pVg1.D.Tt expression vector containing an NheI restriction site in the intron between the hinge and CH2 exons.

Mutations to the lower hinge region of the gamma-1 constant region gene were also generated by site-directed mutagenesis. Specifically amino acid substitutions L234A and L235A (numbered according to the EU index of Kabat, E. A., et al.) were generated using mutagenesis oligos. The PCR step was done using the QuikChange II Site-Directed Mutagenesis Kit (Stratagene) as described above. Following digestion of PCR generated product with NheI and EagI, the resulting restriction fragment was subcloned into the modified pVg1.D.Tt expression vector described above containing the D356E and L358M mutations and an NheI site in the intron between the hinge and CH2 exons. Mutations were verified by nucleotide sequencing.

The amino acid sequences of the humanized VH and VL mini-exons are shown in Table 21. The resulting V gene fragments were cloned, respectively, into a modified form of pVg1.D.Tt and pVk.

Human kidney cell line 293T/17 (American Type Culture Collection, Manassus, Va.) was maintained in DMEM (Bio-Whittaker, Walkersville, Md.) containing 10% Fetal Bovine Serum (FBS) (HyClone, Logan, Utah), 0.1 mM MEM non-essential amino acids (Invitrogen Corporation) and 2 mM L-glutamine (Invitrogen Corporation), hereinafter referred to as 293 medium, at 37° C. in a 7.5% $CO_2$ incubator. For expression and purification of monoclonal antibodies after transient transfection, 293T/17 cells were incubated in DMEM containing 10% low-IgG FBS (HyClone), 0.1 mM MEM non-essential amino acids and 2 mM L-glutamine, hereinafter referred to as low-IgG 293 medium.

Transient transfection of 293T/17 cells was carried out using Lipofectamine 2000 (Invitrogen Corporation) following the manufacturer's recommendations. Approximately $2 \times 10^7$ cells per transfection were plated in a T-175 flask in 50 ml of 293 medium and grown overnight to confluence. The next day, 35 µg of light chain plasmid and 35 µg of heavy chain plasmid were combined with 3.75 ml of Hybridoma-SFM (HSFM) (Life Technologies, Rockville, Md.). In a separate tube, 175 µl of Lipofectamine 2000 reagent and 3.75 ml of HSFM were combined and incubated for 5 min at room temperature. The 3.75 ml Lipofectamine 2000-HSFM mixture was mixed gently with the 3.75 ml DNA-HSFM mixture and incubated at room temperature for 20 min. The medium covering the 293T/17 cells was aspirated and replaced with low-IgG 293 medium, then the lipofectamine-DNA complexes were added dropwise to the cells, mixed gently by swirling, and the cells were incubated for 7 days at 37° C. in a 7.5% $CO_2$ incubator before harvesting the supernatants. Transient transfectants producing 8E1.4, 8E1.5 and 8E1.6 were generated as described above.

Expression of humanized 8E1.4, 8E1.5 and 8E1.6 antibodies was measured by sandwich ELISA. MaxiSorp ELISA plates (Nunc Nalge International, Rochester, N.Y.) were coated overnight at 4° C. with 100 µl/well of a 1:1000 dilution of AffiniPure goat anti-human IgG Fcγ-chain specific polyclonal antibodies (Jackson ImmunoResearch Laboratories, Inc., West Grove, Pa.) in 0.2 M sodium carbonate-bicarbonate buffer, pH 9.4, washed with Wash Buffer (PBS containing 0.1% Tween 20), and blocked for 1 hr at room temperature with 300 µl/well of SuperBlock Blocking Buffer in TBS (Pierce Chemical Company, Rockford, Ill.). After washing with Wash Buffer, samples containing 8E1.4, 8E1.5 or 8E1.6 were appropriately diluted in ELISA Buffer (PBS containing 1% BSA and 0.1% Tween 20) and 100 µl/well was applied to the ELISA plates. As a standard, humanized IgG1/K antibody daclizumab (PDL BioPharma, Inc.) was used. After incubating the plates for 1 hr at room temperature, and washing with Wash Buffer, bound antibodies were detected using 100 µl/well of a 1:1000 dilution of HRP-conjugated goat anti-human kappa light chain specific polyclonal antibodies (Southern Biotechnology Associates, Inc., Birmingham, Ala.). After incubating for 1 hr at room temperature, and washing with Wash Buffer, color development was performed by adding 100 μl/well of ABTS Peroxidase Substrate/Peroxidase Solution B (KPL, Inc., Gaithersburg, Md.). After incubating for 7 min at room temperature, color development was stopped by adding 50 μl/well of 2% oxalic acid. Absorbance was read at 415 nm using a VersaMax microplate reader (Molecular Devices Corporation, Sunnyvale, Calif.). Culture supernatants obtained from transiently transfected 293T/17 cells were analyzed by ELISA for production of 8E1.4, 8E1.5 and 8E1.6. Expression levels of approximately 30-50 μg/ml were typically observed. Samples that were positive were subjected purification as described below.

Example 2.4.5

Purification of Additional Humanized Antibodies

8E1.4, 8E1.5 and 8E1.6 IgG1/K monoclonal antibodies were purified from exhausted culture supernatant with a protein A Sepharose column as follows. Culture supernatants from transient transfections were harvested by centrifugation, and sterile filtered. The pH of the filtered supernatants was adjusted by addition of 1/50 volume of 1 M sodium citrate, pH 7.0. Supernatants were run over a 1 ml HiTrap Protein A HP column (GE Healthcare Bio-Sciences Corporation, Piscataway, N.J.) that was pre-equilibrated with 20 mM sodium citrate, 150 mM NaCl, pH 7.0. The column was washed with the same buffer, and bound antibody was eluted with 20 mM sodium citrate, pH 3.5. After neutralization by addition of 1/50 volume of 1.5 M sodium citrate, pH 6.5, the pooled antibody fractions were concentrated to ~0.5-1.0 mg/ml using a 15 ml Amicon Ultra-15 centrifugal filter device (30,000 dalton MWCO) (Millipore Corporation, Bedford, Mass.). Samples were then filter sterilized using a 0.2 μm Acrodisc syringe filter with HT Tuffryn membrane (Pall Corporation, East Hills, N.Y.). The concentrations of the purified antibodies were determined by UV spectroscopy by measuring the absorbance at 280 nm (1 mg/ml=1.4 $A_{280}$).

SDS-PAGE analysis under non-reducing conditions indicated that the antibodies had a molecular weight of about 150-160 kD. Analysis under reducing conditions indicated that the antibodies were comprised of a heavy chain with a molecular weight of about 50 kD and a light chain with a molecular weight of about 25 kD. The purity of the antibodies appeared to be more than 95%.

Example 2.4.6

Characterization of Additional Humanized Antibodies Using Competition ELISA

MaxiSorp ELISA plates (Nalge Nunc International) were coated overnight at 4° C. with 100 μl/well of 1.0 μg/ml human IL-12 in 0.2 M sodium carbonate-bicarbonate buffer, pH 9.4, washed with Wash Buffer (PBS containing 0.1% Tween 20), and blocked for 1 hr at room temperature with 300 μl/well of SuperBlock Blocking Buffer in TBS (Pierce Chemical Company). After washing with Wash Buffer, a mixture of biotinylated 8E1 (0.8 μg/ml final concentration) and competitor antibody (8E1 or 8E1.4 or 8E1.5 or 8E1.6) starting at 100 μg/ml final concentration and serially diluted 3-fold) in 100 μl/well of ELISA buffer was added in duplicate. As isotype controls, 100 μl/well of 100 μg/ml mouse IgG1/K (MuFd79) or humanized IgG1/K (HuFd79) monoclonal antibodies in ELISA buffer was used. As a no-competitor control, 100 μl/well of ELISA Buffer was used. After incubating the plates for 1 hr at room temperature, and washing with Wash Buffer, bound antibodies were detected using 100 μl/well of 1 μg/ml HRP-conjugated streptavidin (Pierce Chemical Company) in ELISA buffer. After incubating for 1 hr at room temperature, and washing with Wash Buffer, color development was performed by adding 100 μl/well of ABTS Peroxidase Substrate/Peroxidase Solution B (KPL, Inc.). After incubating for 5 min at room temperature, color development was stopped by adding 50 μl/well of 2% oxalic acid. Absorbance was read at 415 nm.

The affinity of 8E1.4, 8E1.5 and 8E1.6 to human IL-12 was analyzed by competition ELISA as described above. Both 8E1 and the three humanized versions competed with biotinylated 8E1 in a concentration-dependent manner Table 23 shows the $IC_{50}$ values of 8E1, 8E1.4, 8E1.5 and 8E1.6 obtained using the computer software GraphPad Prism (GraphPad Software Inc., San Diego, Calif.).

TABLE 23

Binding properties of 8E1.4, 8E1.5 and 8E1.6 antibodies

| Antibody | Expt. 1 | Expt. 2 | Expt. 3 | Average | S.D. |
|---|---|---|---|---|---|
| 8E1 | 2.63 | 2.78 | 2.28 | 2.56 | 0.26 |
| 8E1.4 | N.D. | N.D. | 8.33 | N/A | N/A |
| 8E1.5 | N.D. | N.D. | 13.4 | N/A | N/A |
| 8E1.6 | 2.25 | 2.43 | 1.61 | 2.10 | 0.43 |

The values represent IC50 (μg/ml) required to compete 0.8 (μg/ml) biotinylated 8E1 antibody.

Antibodies 1A6.10, 1A6.11, 1A6.12, 8E1.4 and 8E1.5 were also generated using methods described in Example 2.3. Antibodies were expressed in COS cells and purified by Protein A affinity chromatography as described in examples 2.2.2 and 1.2.C, respectively. These purified mAbs were characterized for $IC_{50}$ and $K_D$ according to example 1.1.B and 1.1.C2. Table 24 shows the binding properties of 1A6.10, 1A6.11, 1A6.12, 8E1.4 and 8E1.5.

TABLE 24

Kinetic and potency parameters of additional humanized antibodies

| Antibody | 1A6.10 | 1A6.11 | 1A6.12 | 8E1.4 | 8E1.5 | 8E1.6 |
|---|---|---|---|---|---|---|
| On-rate (1/M · s) | $3.2 \times 10^5$ | ND | $7.4 \times 10^5$ | $8 \times 10^5$ | $1.6 \times 10^6$ | $1.7 \times 10^6$ |
| Off-rate (1/s) | $7.6 \times 10^{-6}$ | ND | $3 \times 10^{-4}$ | $1 \times 10^{-3}$ | $1.24 \times 10^{-3}$ | $8 \times 10^{-5}$ |
| KD (nM) | 0.024 | ND | 0.4 | 1.3 | 0.75 | 0.046 |
| Av · $IC_{50}$(nM) huIL-12 | 0.15 | ND | 0.088 | 12 | 8 | ND |

TABLE 24-continued

Kinetic and potency parameters of additional humanized antibodies

| Antibody | 1A6.10 | 1A6.11 | 1A6.12 | 8E1.4 | 8E1.5 | 8E1.6 |
|---|---|---|---|---|---|---|
| Av · $IC_{50}$(nM) cyno IL-12 | ND | ND | ND | ND | ND | ND |

The present invention incorporates by reference in their entirety techniques well known in the field of molecular biology. These techniques include, but are not limited to, techniques described in the following publications:

Ausubel, F. M. et al. eds., *Short Protocols In Molecular Biology* (4th Ed. 1999) John Wiley & Sons, NY. (ISBN 0-471-32938-X).

Lu and Weiner eds., *Cloning and Expression Vectors for Gene Function Analysis* (2001) BioTechniques Press. Westborough, Mass. 298 pp. (ISBN 1-881299-21-X).

Kontermann and Dubel eds., *Antibody Engineering* (2001) Springer-Verlag. New York. 790 pp. (ISBN 3-540-41354-5).

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, NY. Vols. 1-3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-614-4).

REFERENCES

U.S. Pat. Nos.
4,816,397,
4,816,567,
4,880,078;
5,985,309,
5,223,409;
5,225,539;
5,258,498;
5,290,540,
5,403,484;
5,427,908;
5,516,637;
5,530,101;
5,571,698;
5,580,717;
5,585,089,
5,658,727;
5,693,762,
5,714,352,
5,723,323,
5,733,743
5,750,753;
5,766,886,
5,780,225;
5,817,483,
5,821,047;
5,824,514,
5,855,913,
5,874,064,
5,934,272,
5,939,598,
5,969,108;
5,976,862,
5,985,320,
5,985,309,
5,985,615,
5,998,209,
5,624,821
5,723,323,
5,763,192,
5,814,476,
6,075,181,
6,091,001,
6,114,598
6,130,364
6,180,370,
6,204,023,
6,350,861,
5,585,089,
6,914,128
4,526,938,
4,980,286,
5,912,015;
4,946,778,
5,916,597;
5,128,326;
5,565,352
5,679,377;
5,989,463;
5,225,539;
5,565,332,
5,698,426;
5,714,350,
5,807,715,
6,019,968,
5,627,052,
5,916,771,
5,648,260,
6,660,843 (U.S. application Ser. No. 09/428,082)
6,699,658,
U.S patent publications
2002/0137134
2004/0018590
2003/0186374
2005/0042664 A1
2006/0104968

FOREIGN PATENTS

WO 97/15327,
WO 00/56772 A1
WO 91/17271,
WO 92/09690,
WO 99/37682 A2,
WO 92/15679,
WO 92/01047,
WO 2002/097048 A2,
WO 95/24918 A1,
WO 99/25044,
WO 97/29131,

WO 98/31700
WO 99/15154;
WO 99/20253,
WO 92/19244,
WO 00/37504,
WO 00/56772.
WO 91/05548,
WO 91/09967,
WO 92/02551
WO 92/22324
WO 93/01288
WO 96/20698,
WO 97/29131
WO 01/83525.
WO 2003/016466 A2,
WO 2005/100584 A2
WO 03/035835;
WO 90/02809,
WO 99/06834
WO 97/20032
WO 92/11272
WO 92/03461
WO 94/18219
WO 93/06213
WO 92/20791,
WO 90/05144 A1
WO 00 09560,
WO 00/037504
WO 02/072636,
WO 91/10737,
WO 91/10741
WO 92/18619,
WO 93/11236,
WO 94/02602,
WO 95/15982,
WO 95/20401,
WO 96/33735
WO 96/34096
WO 97/32572,
WO 97/32572,
WO 97/44013,
WO 98/16654
WO 98/24893,
WO 98/31346,
WO 98/50433,
WO 99/45031,
WO 99/53049,
WO 99/54342
WO 99/66903,
WO 90/14424,
WO 90/14430,
WO 90/14443
WO 2004/078140
European Patent No:
EP 0 239 400
EP 0 519 596
EP 0 592 106
EP 1 176 195

NON-PATENT LITERATURE DOCUMENTS

Ames et al., J. Immunol. Methods 184:177-186 (1995),
Azzazy H., and Highsmith W. E., (2002) Clin. Biochem. 35:425-445;
Babcook, J. S. et al. (1996) Proc. Natl. Acad. Sci. USA 93:7843-7848,
Barbas et al. (1991)Proc. Natl. Acad. Sci. USA 88:7978-7982,
Bentley, D. L., and Rabbitts, T. H., Cell 32: 181-189 (1983),
Berrebi et al. (1998) Am. J Path 152:667-672,
Better et al., Science 240:1041-1043 (1988),
Bird et al. (1988) Science 242:423-426,
Brinkman et al., J. Immunol. Methods 182:41-50 (1995),
Broberg, et al. (2002) J. Interferon Cytokine Res. 22:641-651,
Brown et al. (1991) Proc. Natl. Acad. Sci. USA 88:2663-2667,
Bucht et al., (1996) Clin. Exp. Immunol. 103:347-367,
Buchwald et al., 1980, Surgery 88:507-516
Burton et al., Advances in Immunology 57:191-280 (1994),
Carter et al., Proc. Natl. Acad. Sci. USA 89:4285 (1992);
Chothia & Lesk, J. Mol. Biol. 196:901-917 (1987),
Chothia et al., J. Mol. Biol. 227: 799-817 (1992),
Chothia et al., Nature 342:877-883 (1989),
Clackson et al. (1991) Nature 352:624-628,
Cleek et al., 1997, "Biodegradable Polymeric Carriers for a bFGF Antibody for Cardiovascular Application," Pro. Int'l. Symp. Control. Rel. Bioact. Mater. 24:853-854,
Co, M. S., et al., J. Immunol. 148: 1149-1154 (1992)
Co, M. S., et al., Mol. Immunol. (1993) 30:1361-1367,
Cole, M. S., et al., J. Immunol. 159: 3613-3621 (1997), Controlled Drug Bioavailability, Drug Product Design and Performance, Smolen and Ball, eds. (Wiley, New York 1984)
Cooper, et al. (2002) J. Immunol. 168:1322-1327,
Cua et al. (2003) Nature 421:744-748,
Duchmann et al., J Immunol. 26:934-938 (1996),
During et al., 1989, Ann. Neurol. 25:351-356
Durocher et al., Nucleic Acids Research 2002, Vol 30, No. 2, e9
Elkins, et al. (2002) Infection Immunity 70:1936-1948,
Fais et al. (1994) J. Interferon Res. 14:235-238;
Foote and Winter (1992), J. Mol. Biol. 224:487-499,
Fuchs et al. (1991) Bio/Technology 9: 1369-1372,
Fuss, et al., (1996) J. Immunol. 157:1261-1270,
Garrard et al. (1991) Bio/Technology 9:1373-1377,
Gavilondo J. V., and Larrick J. W. (2002) BioTechniques 29:128-145;
Giegé et al., Chapter 1, In Crystallization of Nucleic Acids and Proteins, a Practical Approach, 2nd ed., (Ducruix and Giegé, eds.) (Oxford University Press, New York, 1999) pp. 1-16
Gillies et al., (1989) J. Immunol. Methods 125:191-202,
Goldspiel et al., 1993, Clinical Pharmacy 12:488-505;
Goodson, J. M., Chapter 6, In Medical Applications of Controlled Release, Vol. II, Applications and Evaluation, (Langer and Wise, eds.) (CRC Press, Inc., Boca Raton, 1984), pp. 115-138
Gram et al. (1992) Proc. Natl. Acad. Sci. USA 89:3576-3580,
Green and Jakobovits J. Exp. Med. 188:483-495 (1998),
Green et al. Nature Genetics 7:13-21 (1994)
Griffiths et al. (1993) EMBO J 12:725-734,
Hammerling, et al., Monoclonal Antibodies and T-Cell Hybridomas 563-681 (Elsevier, N.Y., 1981),
Harlow et al., Antibodies: A Laboratory Manual, (Cold Spring Harbor Laboratory Press, 2nd ed. 1988),
Hawkins et al. (1992) J. Mol Biol 226: 889-896
Hay et al. (1992) Hum Antibod Hybridomas 3:81-85,
Hieter, P. A., et al., J. Biol. Chem. 257: 1516-1522 (1982),
Higuchi, R., in "PCR Technology: Principles and Applications for DNA Amplification", Stockton Press, New York (1989), pp. 61-70,
Holliger, P., et al. (1993) Proc. Natl. Acad. Sci. USA 90: 6444-6448,
Hoogenboom et al. (1991) Nucl. Acid Res. 19: 4133-4137,
Hoogenboom H. R., (1997) Trends Biotechnol. 15:62-70;

Hoogenboom H., and Chames P. (2000) *Immunology Today* 21:371-378,
Howard et al., 1989, *J. Neurosurg.* 7 1:105-112
Huse et al. (1989) *Science* 246:1275-1281,
Huston et al. (1988) *Proc. Natl. Acad. Sci. USA* 85:5879-5883,
Huston et al., Methods in Enzymology 203:46-88 (1991);
Jefferis, R., *Biotechnol. Prog.* 21 (2005), pp. 11-16,
Johnnson, B., et al. (1991) *Anal. Biochem.* 198:268-277.
Johnsson, B., et al. (1995) *J. Mol. Recognit.* 8:125-131,
Joliot et al., 1991, *Proc. Natl. Acad. Sci. USA* 88:1864-1868,
Jones et al., *Nature* 321: 522-525 (1986);
Jönsson, U., et al. (1993) *Ann. Biol. Clin.* 51:19-26;
Jönsson, U., et al. (1991) *BioTechniques* 11:620-627,
Junghans, et al. (1990) *Cancer Res.* 50:1495-1502,
Kabat et al. (1971) *Ann. NY Acad, Sci.* 190:382-391,
Kabat, E. A., et al. (1991) *Sequences of Proteins of Immunological Interest, Fifth Edition*, U.S. Department of Health and Human Services, NIH Publication No. 91-3242,
Kaufman, R. J. and Sharp, P. A. (1982) *J. Mol. Biol.* 159:601-621,
Kellermann S-A., and Green L. L. (2002) *Current Opinion in Biotechnology* 13:593-597,
Kettleborough et al. (1991) *Prot. Engineer.* 4: 773-783,
Kettleborough et al., *Eur. J. Immunol.* 24: 952-958 (1994)
Kipriyanov, S. M., et al. (1994) *Mol. Immunol.* 31: 1047-1058
Kipriyanov, S. M., et al. (1995) *Human Antibodies and Hybridomas* 6: 93-101
Kobayashi, et al. (1989) *J. Exp. Med.* 170: 827-845;
Kohler, G. and Milstein 1975, Nature, 256:495,
Kontermann and Dubel eds., *Antibody Engineering* (2001) Springer-Verlag. New York. 790 pp. (ISBN 3-540-41354-5),
Lam et al., 1997, "Microencapsulation of Recombinant Humanized Monoclonal Antibody for Local Delivery," Proc. Int'l. Symp. Control Rel. Bioact. Mater. 24:759-760,
Langer (1990) *Science* 249:1527-1533,
Langer and Peppas, 1983, *J. Macromol. Sci. Rev. Macromol. Chem.* 23:61;
Langrish et. al. (2004) *Immunological Reviews* 202: 96-105,
Levitt, M., *J. Mol. Biol.* 168: 595-620 (1983),
Levy et al., 1985, *Science* 228: 190-192
Ling, et al. (1995) *J. Immunol.* 154: 116-127;
Little M. et al (2000) *Immunology Today* 21: 364-370,
Lund et al., 1991, *J. Immunol.,* 147:2657-2662
MacCallum, *J. Mol. Biol.* 262(5):732-745 (1996)
Manheimer-Lory, A., et al., *J. Exp. Med.* 174: 1639-1652 (1991)
Marchalonis et al., *Adv. Exp. Med. Biol.* 484:13-30 (2001)
McCafferty et al., *Nature* (1990) 348:552-554
Mendez et al., *Nature Genetics* 15:146-156 (1997)
Mizushima and Nagata, *Nucleic Acids Research*, Vol 18, No. 17, pg 5322 (1990)
Monteleone et al., (1997) *Gastroent.* 112: 1169-1178
Morgan and Anderson, 1993, *Ann. Rev. Biochem.* 62:191-217
Morita et al., (1998) *Arth. and Rheumat.* 41: 306-314
Morrison et al., 1984, *Proc. Natl. Acad. Sci. USA* 81: 6851-6855
Morrison, *Science* 229: 1202-1207 (1985),
Mulligan, *Science* 260:926-932 (1993);
Mullinax et al., *BioTechniques* 12(6):864-869 (1992),
Murphy et al., *J. Exp. Med.* 198:1951-1957 (2003)
Neuberger et al., 1984, *Nature* 312:604-608,
Neurath et al., *J. Exp. Med.* 182:1281-1290 (1995),
Ning et al., 1996, "Intratumoral Radioimmunotherapy of a Human Colon Cancer Xenograft Using a Sustained-Release Gel," *Radiotherapy & Oncology* 39:179-189,
Oi et al., *BioTechniques* 4: 214-221 (1986);
Olee, T., et al., *J. Exp. Med.* 175: 831-842 (1992),
Oppmann et al. (2000) *Immunity* 13:715-725,
Padlan et al., *FASEB J.* 9:133-139 (1995),
Padlan, *Molecular Immunology* 28(4/5):489-498 (1991),
Parham, et al. (2002) *J. Immunol.* 168:5699-5708,
Parronchi et al (1997) *Am. J. Path.* 150:823-832,
Persic et al., *Gene* 187 9-18 (1997),
Petrey et al. (2003) "Using multiple structure alignments, fast model building, and energetic analysis in fold recognition and homology modeling'" *Proteins* 53 (Suppl. 6): 430-435
Pirhonen, et al. (2002) *J. Immunol.* 169:5673-5678,
Podlaski, et al. (1992) *Arch. Biochem. Biophys.* 294:230-237,
Poljak, R. J. (1994) *Structure* 2:1121-1123,
Presta et al., *J. Immunol.* 151:2623 (1993),
Queen, C., et al., *Proc. Natl. Acad. Sci. USA* 86: 10029-10033 (1989),
Ravetch, J. V., et al., *Cell* 27: 583-591 (1981),
Remington's Pharmaceutical Sciences and Introduction to Pharmaceutical Dosage Forms, 19$^{th}$ ed., Mack Pub. Co., Easton, Pa. (1995),
Riechmann et al., *Nature* 332: 323-327 (1988),
Roberts, R. W. and Szostak, J. W. (1997) *Proc. Natl. Acad. Sci. USA* 94:12297-12302,
Robinson, C., 1993, *Trends Biotechnol.* 11(5): 155-215
Roguska. et al., *Proc. Natl. Acad. Sci. USA* 91:969-973 (1994);
Rouillard, J.-M., et al., *Nucleic Acids Res.* 32: W176-W180 (2004),
Saudek et al., 1989, *N. Engl. J. Med.* 321:574-579
Sawai et al., *Am. J. Reprod. Immunol.* 34:26-34 (1995),
Schroeder and Wang, *Proc. Natl. Acad. Sci. USA* 87: 6146-6150 (1990),
Seder, et al. (1993) *Proc. Natl. Acad. Sci. USA* 90:10188-10192,
Sefton, 1987, *CRC Crit. Rev. Biomed. Eng.* 14: 201-240
Shapiro et al., *Crit. Rev. Immunol.* 22(3): 183-200 (2002),
Shields, R. L. et al. (2002) J. Biol. Chem. 277:26733-26740,
Shu et al., *Proc. Natl. Acad. Sci. USA* 90:7995-7999 (1993);
Sims et al., *J. Immunol.* 151: 2296-2308 (1993);
Skerra et al., *Science* 240:1038-1041 (1988).
Song et al., 1995, "Antibody Mediated Lung Targeting of Long-Circulating Emulsions," PDA Journal of Pharmaceutical Science &Technology 50:372-377
Studnicka et al., *Protein Engineering* 7(6):805-814 (1994); *Sustained and Controlled Release Drug Delivery Systems*, J. R. Robinson, ed. (Marcel Dekker, Inc., New York 1978).
Takeda et al., 1985, *Nature* 314:452-454
Taylor, L. D., et al. (1992) *Nucl. Acids Res.* 20:6287-6295,
Tolstoshev, 1993, *Ann. Rev. Pharmacol. Toxicol.* 32:573-596;
Trinchieri et al. (2003) *Immunity* 19:641-644,
Trinchieri, G. (2003) *Nat. Rev. Immun.* 3:133-146,
Umana et al. (1999) *Nat. Biotech.* 17: 176-180,
Urlaub and Chasin, (1980) *Proc. Natl. Acad. Sci. USA* 77:4216-4220,
Verhoeyen et al., *Science* 239: 1534-1536 (1988)
Wallick, S. C., et al., *J. Exp. Med.* (1988) 168:1099-1109,
Ward et al., (1989) *Nature* 341:544-546,
Welschof, M. and Krauss, *J. Methods In Molecular Biology, Vol* 207,
Windhagen et al., (1995) J Exp. Med. 182:1985-1996,
Winnacker, E. L., From Genes To Clones: Introduction To Gene Technology (1987) VCH Publishers, NY (translated by Horst Ibelgaufts). 634 pp. (ISBN 0-89573-614-4).

Wright, A., et al., *EMBO J.* (1991) 10: 2717-2723
Wu and Wu, 1991, *Biotherapy* 3:87-95;
Wu and Wu, *J. Biol. Chem.* 262:4429-4432 (1987)

Although a number of embodiments and features have been described above, it will be understood by those skilled in the art that modifications and variations of the described embodiments and features may be made without departing from the present disclosure or the invention as defined in the appended claims. Each of the publications mentioned herein is incorporated by reference.

We claim:

1. An isolated nucleic acid encoding an amino acid sequence of at least one variable domain of a binding protein, wherein said at least one variable domain comprises CDR-H1, CDR-H2, and CDR-H3 amino acid sequences independently selected from the group consisting of:

| CDR-H1 | CDR-H2 |
|---|---|
| residues 31-37 of SEQ ID NO: 35 | residues 52-67 of SEQ ID NO: 35 |
| residues 31-37 of SEQ ID NO: 37 | residues 52-67 of SEQ ID NO: 37 |
| residues 31-35 of SEQ ID NO: 39 | residues 50-66 of SEQ ID NO: 39 |
| residues 31-35 of SEQ ID NO: 41 | residues 50-66 of SEQ ID NO: 41 |
| residues 31-35 of SEQ ID NO: 43 | residues 50-66 of SEQ ID NO: 43 |
| residues 31-35 of SEQ ID NO: 45 | residues 50-66 of SEQ ID NO: 45 |
| residues 31-35 of SEQ ID NO: 47 | residues 50-66 of SEQ ID NO: 47 |
| residues 31-35 of SEQ ID NO: 49 | residues 50-66 of SEQ ID NO: 49 |
| residues 31-37 of SEQ ID NO: 51 | residues 52-67 of SEQ ID NO: 51 |
| residues 31-35 of SEQ ID NO: 53 | residues 47-66 of SEQ ID NO: 53 |

| CDR-H3 |
|---|
| residues 100-108 of SEQ ID NO: 35 |
| residues.100-109 of SEQ ID NO: 37 |
| residues 99-106 of SEQ ID NO: 39 |
| residues 99-106 of SEQ ID NO: 41 |
| residues 99-106 of SEQ ID NO: 43 |
| residues 99-101 of SEQ ID NO: 45 |
| residues 99-106 of SEQ ID NO: 47 |
| residues 99-111 of SEQ ID NO: 49 |
| residues 100-109 of SEQ ID NO: 51 |
| residues 99-107 of SEQ ID NO: 53. |

2. An isolated nucleic acid encoding an amino acid sequence of at least one variable domain of a binding protein, wherein said at least one variable domain comprises CDR-L1, CDR-L2, and CDR-L3 amino acid sequences independently selected from the group consisting of:

| CDR-L1 | CDR-L2 | CDR-L3 |
|---|---|---|
| residues 24-34 of SEQ ID NO: 36 | residues 50-56 of SEQ ID NO: 36 | residues 89-97 of SEQ ID NO: 36 |
| residues 24-34 of SEQ ID NO: 38 | residues 50-56 of SEQ ID NO: 38 | residues 89-97 of SEQ ID NO: 38 |
| residues 24-34 of SEQ ID NO: 40 | residues 50-56 of SEQ ID NO: 40 | residues 89-97 of SEQ ID NO: 40 |
| residues 24-34 of SEQ ID NO: 42 | residues 50-56 of SEQ ID NO: 42 | residues 89-97 of SEQ ID NO: 42 |
| residues 24-34 of SEQ ID NO: 44 | residues 50-56 of SEQ ID NO: 44 | residues 89-97 of SEQ ID NO: 44 |
| residues 24-34 of SEQ ID NO: 46 | residues 50-56 of SEQ ID NO: 46 | residues 89-97 of SEQ ID NO: 46 |
| residues 24-34 of SEQ ID NO: 48 | residues 50-56 of SEQ ID NO: 48 | residues 89-97 of SEQ ID NO: 48 |
| residues 24-38 of SEQ ID NO: 50 | residues 53-60 of SEQ ID NO: 50 | residues 93-101 of SEQ ID NO: 50 |
| residues 24-34 of SEQ ID NO: 52 | residues 50-56 of SEQ ID NO: 52 | residues 89-97 of SEQ ID NO: 52 |
| residues 24-34 of SEQ ID NO: 54 | residues 50-56 of SEQ ID NO: 54 | residues 89-97 of SEQ ID NO: 54. |

3. The isolated nucleic acid according to either claim 1 or claim 2, encoding an antibody construct amino acid sequence, wherein said antibody construct comprises said binding protein and further comprises a linker polypeptide or an immunoglobulin constant domain.

4. The isolated nucleic acid according to either claim 1 or claim 2 encoding an antibody conjugate amino acid sequence, wherein said antibody conjugate comprises said binding protein linked to another moiety.

5. A vector comprising an isolated nucleic acid according to either claim 1 or claim 2.

6. The vector of claim 5 wherein said vector is selected from the group consisting of pcDNA, pTT, pTT3, pEFBOS, pBV, pJV, and pBJ.

7. A host cell comprising a vector according to claim 5.

8. The host cell according to claim 7, wherein said host cell is a prokaryotic cell.

9. The host cell according to claim 8, wherein said host cell is *E. coli*.

10. The host cell according to claim 7, wherein said host cell is a eukaryotic cell.

11. The host cell according to claim 10, wherein said eukaryotic cell is selected from the group consisting of protist cell, animal cell, plant cell and fungal cell.

12. The host cell according to claim 10, wherein said eukaryotic cell is an animal cell selected from the group consisting of: a mammalian cell, an avian cell, and an insect cell.

13. The host cell according to claim 10, wherein said host cell is a CHO cell.

14. The host cell according to claim 10, wherein said host cell is a COS cell.

15. The host cell according to claim 10, wherein said host cell is a yeast cell.

16. The host cell according to claim 15, wherein said yeast cell is *Saccharomyces cerevisiae*.

17. The host cell according to claim 12, wherein said host cell is an insect Sf9 cell.

18. A host cell comprising at least one nucleic acid according to either claim 1 or claim 2.

19. A host cell comprising one or more nucleic acids encoding a polypeptide chain including CDR-H1, CDR-H2, and CDR-H3 amino acid sequences independently selected from the group consisting of:

| CDR-H1 | CDR-H2 | CDR-H3 |
|---|---|---|
| residues 31-37 of SEQ ID NO: 35 | residues 52-67 of SEQ ID NO: 35 | residues 100-108 of SEQ ID NO: 35 |
| residues 31-37 of SEQ ID NO: 37 | residues 52-67 of SEQ ID NO: 37 | residues.100-109 of SEQ ID NO: 37 |
| residues 31-35 of SEQ ID NO: 39 | residues 50-66 of SEQ ID NO: 39 | residues 99-106 of SEQ ID NO: 39 |
| residues 31-35 of SEQ ID NO: 41 | residues 50-66 of SEQ ID NO: 41 | residues 99-106 of SEQ ID NO: 41 |
| residues 31-35 of SEQ ID NO: 43 | residues 50-66 of SEQ ID NO: 43 | residues 99-106 of SEQ ID NO: 43 |
| residues 31-35 of SEQ ID NO: 45 | residues 50-66 of SEQ ID NO: 45 | residues 99-101 of SEQ ID NO: 45 |
| residues 31-35 of SEQ ID NO: 47 | residues 50-66 of SEQ ID NO: 47 | residues 99-106 of SEQ ID NO: 47 |
| residues 31-35 of SEQ ID NO: 49 | residues 50-66 of SEQ ID NO: 49 | residues 99-111 of SEQ ID NO: 49 |
| residues 31-37 of SEQ ID NO: 51 | residues 52-67 of SEQ ID NO: 51 | residues 100-109 of SEQ ID NO: 51 |
| residues 31-35 of SEQ ID NO: 53 | residues 47-66 of SEQ ID NO: 53 | residues 99-107 of SEQ ID NO: 53 | and nucleic acids encoding a polypeptide chain including CDR-L1, CDR-L2, and CDR-L3 amino acid sequences independently selected from the group consisting of:

| CDR-L1 | CDR-L2 | CDR-L3 |
|---|---|---|
| residues 24-34 of SEQ ID NO: 36 | residues 50-56 of SEQ ID NO: 36 | residues 89-97 of SEQ ID NO: 36 |
| residues 24-34 of SEQ ID NO: 38 | residues 50-56 of SEQ ID NO: 38 | residues 89-97 of SEQ ID NO: 38 |
| residues 24-34 of SEQ ID NO: 40 | residues 50-56 of SEQ ID NO: 40 | residues 89-97 of SEQ ID NO: 40 |
| residues 24-34 of SEQ ID NO: 42 | residues 50-56 of SEQ ID NO: 42 | residues 89-97 of SEQ ID NO: 42 |
| residues 24-34 of SEQ ID NO: 44 | residues 50-56 of SEQ ID NO: 44 | residues 89-97 of SEQ ID NO: 44 |
| residues 24-34 of SEQ ID NO: 46 | residues 50-56 of SEQ ID NO: 46 | residues 89-97 of SEQ ID NO: 46 |
| residues 24-34 of SEQ ID NO: 48 | residues 50-56 of SEQ ID NO: 48 | residues 89-97 of SEQ ID NO: 48 |
| residues 24-38 of SEQ ID NO: 50 | residues 53-60 of SEQ ID NO: 50 | residues 93-101 of SEQ ID NO: 50 |
| residues 24-34 of SEQ ID NO: 52 | residues 50-56 of SEQ ID NO: 52 | residues 89-97 of SEQ ID NO: 52 |
| residues 24-34 of SEQ ID NO: 54 | residues 50-56 of SEQ ID NO: 54 | residues 89-97 of SEQ ID NO: 54. |

20. A method of producing a protein capable of binding the p40 subunit of IL-12, comprising culturing a host cell of claim 19 in culture medium under conditions sufficient to produce a binding protein capable of binding the p40 subunit of IL-12.

21. A host cell comprising a first nucleic acid encoding a variable heavy chain (VH) set of 3 CDRs and a second nucleic acid encoding a variable light chain (VL) set of 3 CDRs, wherein said VH set of 3 CDRs is selected from any one of the VH sets in the group below and said VL set of 3 CDRs is selected from any one of the VL sets in the group below:

| CDR amino acid sequences | |
|---|---|
| VH 1D4 CDR Set | |
| VH 1D4 CDR-H1 | residues 31-37 of SEQ ID NO: 35 |
| VH 1D4 CDR-H2 | residues 52-67 of SEQ ID NO: 35 |
| VH 1D4 CDR-H3 | residues 100-108 of SEQ ID NO: 35 |
| VL 1D4 CDR Set | |
| VL 1D4 CDR-L1 | residues 24-34 of SEQ ID NO: 36 |
| VL 1D4 CDR-L2 | residues 50-56 of SEQ ID NO: 36 |
| VL 1D4 CDR-L3 | residues 89-97 of SEQ ID NO: 36 |
| VH 1A6 CDR Set | |
| VH 1A6 CDR-H1 | residues 31-37 of SEQ ID NO: 37 |
| VH 1A6 CDR-H2 | residues 52-67 of SEQ ID NO: 37 |
| VH 1A6 CDR-H3 | residues 100-109 of SEQ ID NO: 37 |
| VL 1A6 CDR Set | |
| VL 1A6 CDR-L1 | residues 24-34 of SEQ ID NO: 38 |
| VL 1A6 CDR-L2 | residues 50-56 of SEQ ID NO: 38 |
| VL 1A6 CDR-L3 | residues 89-97 of SEQ ID NO: 38 |
| VH 1D8 CDR Set | |
| VH 1D8 CDR-H1 | residues 31-35 of SEQ ID NO: 39 |
| VH 1D8 CDR-H2 | residues 50-66 of SEQ ID NO: 39 |
| VH 1D8 CDR-H3 | residues 99-106 of SEQ ID NO: 39 |
| VL 1D8 CDR Set | |
| VL 1D8 CDR-L1 | residues 24-34 of SEQ ID NO: 40 |
| VL 1D8 CDR-L2 | residues 50-56 of SEQ ID NO: 40 |
| VL 1D8 CDR-L3 | residues 89-97 of SEQ ID NO: 40 |
| VH 3G7 CDR Set | |
| VH 3G7 CDR-H1 | residues 31-35 of SEQ ID NO: 41 |
| VH 3G7 CDR-H2 | residues 50-66 of SEQ ID NO: 41 |
| VH 3G7 CDR-H3 | residues 99-106 of SEQ ID NO: 41 |
| VL 3G7 CDR Set | |
| VL 3G7 CDR-L1 | residues 24-34 of SEQ ID NO: 42 |
| VL 3G7 CDR-L2 | residues 50-56 of SEQ ID NO: 42 |
| VL 3G7 CDR-L3 | residues 89-97 of SEQ ID NO: 42 |

-continued

| CDR amino acid sequences | |
|---|---|
| VH 5E8 CDR Set | |
| VH 5E8 CDR-H1 | residues 31-35 of SEQ ID NO: 43 |
| VH 5E8 CDR-H2 | residues 50-66 of SEQ ID NO: 43 |
| VH 5E8 CDR-H3 | residues 99-106 of SEQ ID NO: 43 |
| VL 5E8 CDR Set | |
| VL 5E8 CDR-L1 | residues 24-34 of SEQ ID NO: 44 |
| VL 5E8 CDR-L2 | residues 50-56 of SEQ ID NO: 44 |
| VL 5E8 CDR-L3 | residues 89-97 of SEQ ID NO: 44 |
| VH 8E1 CDR Set | |
| VH 8E1 CDR-H1 | residues 31-35 of SEQ ID NO: 45 |
| VH 8E1 CDR-H2 | residues 50-66 of SEQ ID NO: 45 |
| VH 8E1 CDR-H3 | residues 99-101 of SEQ ID NO: 45 |
| VL 8E1 CDR Set | |
| VL 8E1 CDR-L1 | residues 24-34 of SEQ ID NO: 46 |
| VL 8E1 CDR-L2 | residues 50-56 of SEQ ID NO: 46 |
| VL 8E1 CDR-L3 | residues 89-97 of SEQ ID NO: 46 |
| VH 1H6 CDR Set | |
| VH 1H6 CDR-H1 | residues 31-35 of SEQ ID NO: 47 |
| VH 1H6 CDR-H2 | residues 50-66 of SEQ ID NO: 47 |
| VH 1H6 CDR-H3 | residues 99-106 of SEQ ID NO: 47 |
| VL 1H6 CDR Set | |
| VL 1H6 CDR-L1 | residues 24-34 of SEQ ID NO: 48 |
| VL 1H6 CDR-L2 | residues 50-56 of SEQ ID NO: 48 |
| VL 1H6 CDR-L3 | residues 89-97 of SEQ ID NO: 48 |
| VH 3A11 CDR Set | |
| VH 3A11 CDR-H1 | residues 31-35 of SEQ ID NO: 49 |
| VH 3A11 CDR-H2 | residues 50-66 of SEQ ID NO: 49 |
| VH 3A11 CDR-H3 | residues 99-111 of SEQ ID NO: 49 |
| VL 3A11 CDR Set | |
| VL 3A11 CDR-L1 | residues 24-38 of SEQ ID NO: 50 |
| VL 3A11 CDR-L2 | residues 53-60 of SEQ ID NO: 50 |
| VL 3A11 CDR-L3 | residues 93-101 of SEQ ID NO: 50 |
| VH 4B4 CDR Set | |
| VH 4B4 CDR-H1 | residues 31-37 of SEQ ID NO: 51 |
| VH 4B4 CDR-H2 | residues 52-67 of SEQ ID NO: 51 |
| VH 4B4 CDR-H3 | residues 100-109 of SEQ ID NO: 51 |
| VL 4B4 CDR Set | |
| VL 4B4 CDR-L1 | residues 24-34 of SEQ ID NO: 52 |
| VL 4B4 CDR-L2 | residues 50-56 of SEQ ID NO: 52 |
| VL 4B4 CDR-L3 | residues 89-97 of SEQ ID NO: 52 |

-continued

| CDR amino acid sequences | |
|---|---|
| VH 7G3 CDR Set | |
| VH 7G3 CDR-H1 | residues 31-35 of SEQ ID NO: 53 |
| VH 7G3 CDR-H2 | residues 47-66 of SEQ ID NO: 53 |
| VH 7G3 CDR-H3 | residues 99-107 of SEQ ID NO: 53 and |
| VL 7G3 CDR Set | |
| VL 7G3 CDR-L1 | residues 24-34 of SEQ ID NO: 54 |
| VL 7G3 CDR-L2 | residues 50-56 of SEQ ID NO: 54 |
| VL 7G3 CDR-L3 | residues 89-97 of SEQ ID NO: 54. |

22. The host cell according to claim 18, wherein said binding protein comprises at least two variable domain CDR sets.

23. The host cell according to claim 21, which produces at least two variable domain CDR sets selected from a group consisting of:
VH 1D4 CDR set & VL 1D4 CDR set;
VH 1A6 CDR set & VL 1A6 CDR set;
VH 1D8 CDR set & VL 1D8 CDR set;
VH 3G7 CDR set & VL 3G7 CDR set;
VH 5E8 CDR set & VL 5E8 CDR set;
VH 8E1 CDR set & VL 8E1 CDR set;
VH 1H6 CDR set & VL 1H6 CDR set;
VH 3A11 CDR set & VL 3A11 CDR set;
VH 4B4 CDR set & VL 4B4 CDR set; and
VH 7G3 CDR set & VL 7G3 CDR set.

24. The isolated nucleic acid according to either claim 1 or claim 2, further encoding a human acceptor framework.

25. The isolated nucleic acid according to claim 24, wherein said human acceptor framework comprises an amino acid sequence selected from the group consisting of:
SEQ ID NO:6
SEQ ID NO:7
SEQ ID NO:8
SEQ ID NO:9
SEQ ID NO:10
SEQ ID NO:11
SEQ ID NO:12
SEQ ID NO:13
SEQ ID NO:14
SEQ ID NO:15
SEQ ID NO:16
SEQ ID NO:17
SEQ ID NO:18
SEQ ID NO:19
SEQ ID NO:20
SEQ ID NO:21
SEQ ID NO:22
SEQ ID NO:23
SEQ ID NO:24
SEQ ID NO:25
SEQ ID NO:26
SEQ ID NO:27
SEQ ID NO:28
SEQ ID NO:29
SEQ ID NO:30
SEQ ID NO:31
SEQ ID NO:32
SEQ ID NO:33
SEQ ID NO:34
SEQ ID NO:92
SEQ ID NO:93
SEQ ID NO:94
SEQ ID NO:95
SEQ ID NO:96
and
SEQ ID NO:97.

26. The isolated nucleic acid according to claim 24, wherein said human acceptor framework comprises at least one Framework Region amino acid substitution at a key residue, said key residue selected from the group consisting of:
a residue adjacent to a CDR;
a glycosylation site residue;
a rare residue;
a residue capable of interacting with a p40 subunit of human IL-12;
a residue capable of interacting with a CDR;
a canonical residue;
a contact residue between heavy chain variable region and light chain variable region;
a residue within a Vernier zone; and
a residue in a region that overlaps between a Chothia-defined variable heavy chain CDR1 and a Kabat-defined first heavy chain framework.

27. The isolated nucleic acid according to claim 26, wherein the key residue is selected from the group consisting of: 3H, 5H, 10H, 11H, 12H, 13H, 15H, 16H, 18H, 19H, 23H, 24H, 25H, 30H, 41H, 44H, 46H, 49H, 66H, 68H, 71H, 73H, 74H, 75H, 76H, 77H, 78H, 79H, 81H, 82H, 82AH, 82BH, 82CH, 83H, 84H, 85H, 86H, 87H, 89H, 93H, 98H, 108H, 109H, 1L, 2L, 3L, 7L, 8L, 9L, 10L, 11L, 12L, 13L, 15L, 17L, 19L, 20L, 21L, 22L, 36L, 41L, 42L, 43L, 45L, 46L, 58L, 60L, 62L, 63L, 67L, 70L, 73L, 74L, 77L, 78L, 79L, 80L, 83L, 85L, 87L, 104L, and 106L.

28. An isolated nucleic acid encoding an amino acid sequence of at least one variable domain of a binding protein, wherein said at least one variable domain comprises an amino acid sequence selected from the group consisting of:
SEQ ID NO:61
SEQ ID NO:62
SEQ ID NO:63
SEQ ID NO:64
SEQ ID NO:65
SEQ ID NO:66
SEQ ID NO:67
SEQ ID NO:68
SEQ ID NO:69
SEQ ID NO:70
SEQ ID NO:71
SEQ ID NO:72
SEQ ID NO:73
SEQ ID NO:74
SEQ ID NO:75
SEQ ID NO:76
SEQ ID NO:77
and
SEQ ID NO:78.

29. The host cell according to claim 18, producing a binding protein comprising two variable domains, wherein said two variable domains comprise amino acid sequences selected from the group consisting of:
SEQ ID NO:61 & SEQ ID NO:62,
SEQ ID NO:63 & SEQ ID NO:64,
SEQ ID NO:65 & SEQ ID NO:66,
SEQ ID NO:67 & SEQ ID NO:68,
SEQ ID NO:69 & SEQ ID NO:70,
SEQ ID NO:71 & SEQ ID NO:72,
SEQ ID NO:73 & SEQ ID NO:74, SEQ ID NO:75 & SEQ ID NO:76,
SEQ ID NO:77 & SEQ ID NO:78
SEQ ID NO:67 & SEQ ID NO:70, and
SEQ ID NO:69 & SEQ ID NO:68.

30. The host cell according to claim 18, producing a binding protein comprising two variable domains, wherein said two variable domains comprise amino acid sequences selected from the group consisting of:
SEQ ID NO:67 & SEQ ID NO:79,
SEQ ID NO:80 & SEQ ID NO:81,
SEQ ID NO:82 & SEQ ID NO:83,
SEQ ID NO:84 & SEQ ID NO:85,
SEQ ID NO:86 & SEQ ID NO:87,
SEQ ID NO:88 & SEQ ID NO:89,
SEQ ID NO:90 & SEQ ID NO:91,
SEQ ID NO:98 & SEQ ID NO:99,
SEQ ID NO:100 & SEQ ID NO:101,
SEQ ID NO:102 & SEQ ID NO:103,
SEQ ID NO:104 & SEQ ID NO:105,
SEQ ID NO:106 & SEQ ID NO:107, and
SEQ ID NO:108 & SEQ ID NO:109.

31. The host cell according to claim 29, wherein said binding protein is capable of binding a target selected from the group consisting of IL-12, IL-23, or both.

32. The host cell according to claim 30, wherein said binding protein is capable of binding a target selected from the group consisting of IL-12, IL-23, or both.

33. The host cell according to claim 32, wherein said two variable domains comprise: SEQ ID NO:82 & SEQ ID NO:83.

* * * * *